US006171788B1

(12) United States Patent
Nguyen et al.

(10) Patent No.: US 6,171,788 B1
(45) Date of Patent: *Jan. 9, 2001

(54) METHODS FOR THE DIAGNOSIS, PROGNOSIS AND TREATMENT OF GLAUCOMA AND RELATED DISORDERS

(75) Inventors: Thai D. Nguyen; Jon R. Polansky, both of Mill Valley; Pu Chen, Rohnert Park; Hua Chen, San Francisco, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/938,669

(22) Filed: Sep. 26, 1997

Related U.S. Application Data

(63) Continuation-in-part of application No. 08/791,154, filed on Jan. 28, 1997, now abandoned.

(51) Int. Cl.$^{7}$ .............................. C12Q 1/70; C12N 15/11; C07H 21/04

(52) U.S. Cl. ........................... 435/6; 435/91.1; 536/23.1; 536/24.1; 536/24.3; 536/24.31; 536/24.33

(58) Field of Search .......................... 435/6, 91.1, 172.1, 435/320.1, 366, 375, 440; 536/23.1, 24.3, 24.5, 24.1, 24.31, 24.33; 514/44

(56) References Cited

U.S. PATENT DOCUMENTS

| | | | |
|---|---|---|---|
| 3,773,919 | 11/1973 | Boswell et al. | 424/486 |
| 3,887,699 | 6/1975 | Yolles | 424/477 |
| 4,582,788 | 4/1986 | Erlich | 435/6 |
| 4,617,299 | 10/1986 | Knepper | 514/178 |
| 4,683,194 | 7/1987 | Saiki et al. | 435/6 |
| 4,683,202 | 7/1987 | Mullis et al. | 435/91.2 |
| 4,757,089 | 7/1988 | Epstein | 514/571 |
| 4,829,088 | 5/1989 | Doulakas | 514/567 |
| 5,075,217 | 12/1991 | Weber | 435/6 |
| 5,124,154 | 6/1992 | Babcock et al. | 424/427 |
| 5,130,238 | 7/1992 | Malek et al. | 435/91.21 |
| 5,169,766 | 12/1992 | Schuster et al. | 435/91.2 |
| 5,175,082 | 12/1992 | Jeffreys | 435/6 |
| 5,190,762 | 3/1993 | Yarosh | 424/450 |
| 5,192,535 | 3/1993 | Davis et al. | 424/78.04 |
| 5,270,052 | 12/1993 | Callahan et al. | 424/450 |
| 5,420,120 | 5/1995 | Boltralik | 514/172 |
| 5,474,985 | 12/1995 | Polansky et al. | 514/26 |
| 5,599,535 | 2/1997 | Polansky et al. . | |
| 5,606,043 | 2/1997 | Nguyen et al. | 536/23.5 |
| 5,674,888 | 10/1997 | Polansky et al. . | |
| 5,789,169 * | 8/1998 | Nguyen et al. | 435/6 |
| 5,854,415 | 12/1998 | Nguyen et al. . | |
| 5,861,497 | 1/1999 | Nguyen et al. . | |
| 5,885,776 | 3/1999 | Stone et al. . | |
| 5,916,778 | 6/1999 | Stone et al. | 435/91.2 |
| 5,925,748 | 7/1999 | Stone . | |

FOREIGN PATENT DOCUMENTS

| | | |
|---|---|---|
| 1176565 | 10/1984 | (CA) . |
| 2216997 | 3/1999 | (CA) . |
| 50424 | 4/1982 | (EP) . |
| 58481A | 8/1982 | (EP) . |
| 84796 | 8/1983 | (EP) . |
| 158277 A2 | 10/1985 | (EP) . |
| 201184 | 12/1986 | (EP) . |
| 237362 | 9/1987 | (EP) . |
| 258017 | 3/1988 | (EP) . |
| 0 329 822 A2 | 8/1989 | (EP) . |
| 370719 A2 | 5/1990 | (EP) . |
| 2135774A | 9/1984 | (GB) . |
| WO 88/10315 | 12/1988 | (WO) . |
| WO 89/06700 | 7/1989 | (WO) . |
| WO 89/06964 | 8/1989 | (WO) . |
| WO 90/01069 | 2/1990 | (WO) . |
| WO 90/11369 | 10/1990 | (WO) . |
| WO 90/13668 | 11/1990 | (WO) . |
| WO 91/05771 | 5/1991 | (WO) . |
| WO 93/12234 | 6/1993 | (WO) . |
| WO 94/04557 | 3/1994 | (WO) . |
| WO 96/14411 | 5/1996 | (WO) . |
| WO 96/33287 | 10/1996 | (WO) . |
| WO 98/20131 | 5/1998 | (WO) . |
| WO98/32850 | 7/1998 | (WO) . |
| WO98/44107 | 10/1998 | (WO) . |
| WO 99/16898 | 4/1999 | (WO) . |

OTHER PUBLICATIONS

Sarfarazi, Recent Advances in Molecular Genetics of Glaucomas, 6 Human Molecular Genetics 1667–1677, 1997.*

Gewirtz et al., Facilitating Oligonucleotide Delivery: Helping Antisense Deliver on Its Promise, PNAS 93, 3161–3163 (Apr. 1996), May 1996.*

Rojanasakul, Antisense oligonucleotide therapeutics: drug delivery and targeting, Advanced Drug Delivery Reviews v. 18, 115–131 (1996).*

Richard et al., American Journal of Human Genetics 52.5: 915–921 (1993).*

Frazer et al., Genomics 14.3: 574–578 (1992).*

(List continued on next page.)

*Primary Examiner*—Robert A. Schwartzman
*Assistant Examiner*—Mark L. Shibuya
(74) *Attorney, Agent, or Firm*—Howrey, Simon, Arnold & White, LLP

(57) ABSTRACT

The nucleic acid upstream of the TIGR protein encoding sequence can be used to diagnose glaucoma. Polymorphisms, base substitutions, base additions located with the upstream and within TIGR exons can also be used to diagnose glaucoma. In addition, polymorphisms, base substitutions, base additions located with the upstream and within TIGR exons can also be used to prognose glaucoma.

49 Claims, 23 Drawing Sheets

OTHER PUBLICATIONS

Gutman and Wasylyk, The collagenase gene promoter contains a TPA and oncogene–responsive unit encompassing the PEA3 and AP–1 binding sites, EMBO J. 9(7), 2241–2246 (1990).*

Richards et al., Mapping of a Gene for Autosomal Dominant Juvenile–Onset Open–Angle Glaucoma to Chromosome 1q, Am. J. Hum. Genet. 51(1) 62–70, (Jan. 6, 1994).*

Anfossi, G., et al., "An Oligomer Complementary to c–myb–encoded mRNA Inhibits Proliferation of Human Myeloid Leukemia Cell Lines," *Proc. Natl. Acad. Sci.* (*U.S.A.*) 86:3379 (1989).*

Armour, J.A.L. et al., "Recent Advances in Minisatellite Biology," *FEBS Lett.* 307:113–115 (1992).*

Baldino, Frank, Jr., et al., "High–Resolution in Situ Hybridization Histochemistry," *Methods in Enzymology,* 168:761–777 (1989).*

Barany, Francis, "Genetic Disease Detection And DNA Amplification Using Cloned Thermostble Ligase," *Proc. Natl. Acad. Sci.* (U.S.A.) 88:189–193 (1991).*

Becker, D., et al., "Proliferation of Human Malignant Melanomas is Inhibited by Antisense Oligodeoxynucleotides Targeted Against Basibroblast Growth Factor," *EMBO J.* 8:3679 (1989).*

Bengtsson, B., "Incidence of Manifest Glaucoma," *Br. J. Ophthamol.* 73:483–487 (1989).*

Botstein, D. et al., "Construction of a Genetic Linkage Man Using Restriction Fragment Length Polymorphisms," *Amn. J. Hum. Genet.* 32:314–331 (1980).*

Brent et al., "Mutations of the Rat Growth Hormone Promoter Which Increase and Decrease Response to Thyroid Hormone Define a Consensus Thyroid Hormone Response Element," *Molecular endocrinology* 89:1996–2000 (1989).*

Breslauer, Kenneth J. et al., "Predicting DNA Duplex Stability From The Base Sequence," *Proc. Natl. Acad. Sci. USA* 83:3746–3750 (1986).*

Chen, P., "Expression of Trabecular Meshwork Inducible Glucocorticoid Response (TIGR) Peptide In SF9 Cells," *Invest. Opthal. Vis. Sci.* 34(4) 1385 Abstract (1993).*

Clark, A.F., *Exper. Eye Res.* 55:265 (1992).*

Claverie and Makalowski, "Alu Alert," *Nature* 371:751–752 (1994).*

Escribano, J. et al., "Isolation and Characterization of Cell–Specific cDNA Clones from a Substractive Library of the Ocular Ciliary Body of a Single Normal Human Donor: Transcription and Synthesis of Plasma Proteins," *J. Biochem.* 118:921–931 (1995).*

Fauss, D., *Invest. Ophthamol. Vis. Science* 31(4) 432 (1990).*

Freier, Susan M. et al., "Improved Free–Energy Parameters for Predictions of RNA Duplex Stability," *Proc. Natl. Acad. Sci.* (*U.S.A.*) 83:9373–9377 (1986).*

Frohman, M.A. et al., "Rapid Production of Full–length cDNAs From Rare Transcripts: Amplification Using a Single Gene–Specific Oligonucleotide Primer," *Proc. Natl. Acad. Sci.* (*U.S.A.*) 85:8998–9002 (1988).*

Gerwirtz, A.M. et al., "A c–myb Antisense Oligodeoxynucleotide Inhibits Normal Human Hematopoiesis in Vitro," *Science* 242:1303 (1988).*

Goodchild et al., "Inhibition of Human Immunodeficiency Virus Replication By Antisense Oligodeoxynucleotides," *Proc. Natl. Acad. Sci.* (*U.S.A.*) 85:5507 (1988).*

Gounari et al., "Amino–terminal Domain of NF1 Binds as a Dimer and Activates Adenovirus DNA Replication," *EMBO J.* 10:559–566 (1990).*

Gray, I.C. et al., "Evolutionary Transience of Hypervariable Minisatellites In Man and the Primates," *Proc. R. Acad. Soc. Lond.* 243:241–253 (1991).*

Greve, M. et al., "Comparison of the Oculokinetic Perimetry Glaucoma Screener With Two Types of Visual Field Analyser," *Can. J. Ophthamol.* 28:201–206 (1993).*

Gusella, J.F., "DNA Polymorphism and Human Disease," *Ann. Rev. Biochem.* 55:831–854 (1986).*

Hecht et al., "A Progesterone Responsive Element Maps to the Far Upstream Steroid Dependent DNase Hypersensitive Site of Chicken Iysozyme Chromatin," *EMBO J.* 7:2063–2073 (1988).*

Hillel, J. et al., "DNA Fingerprints of Poultry," *Anim. Genet.* 20:145–155 (1989).*

Hillel, J. et al., "DNA fingerprints Applied to Gene Introgression Breeding Progrmas," *Genet.* 124:783–789 (1990).*

Hitchings, R.A., "Glaucoma Screening," *Br. J. Ophthamol.* 77:326 (1993).*

Holt, J.T. et al., "An Oligomer Complementary to c–myc mRNA Inhibits Proliferation of HL–60 Promyelocytic Cells and Induces Differentiation," *Molec. Cell. Biol.* 8:963 (1988).*

Ioannou et al., "A New Bacteriophage P1–derived Vector for the Propagation of Large Human DNA Fragments," *Nature Genetics,* 6:84–89 (1994).*

Jeffreys, A.J. et al., "DNA Fingerprints of Dogs and Cats," *Anim. Genet.* 18:1–15 (1987).*

Jeffreys, A.J. et al., DNA "Fingerprints" and Segregation Analysis of Multiple Markers in Human Pedigrees, *Amer. J. Hum. Genet.* 39:11–24 (1986).*

Jeffreys, A.J. et al., "Individual–Specific 'fingerprints' of Human DNA," *Nature* 316:76–79 (1985).*

Jones, L. et al., "Identical Twin Marrow Transplantation For 5 Patients With Chronic Myeloid Leukaemia: Role of DNA Finger–printing to Confirm Monozygosity in 3 Cases," *Eur. J. Haematol.* 39:144–147 (1987).*

Jurka and Mikahanljaia, "Reconstruction and Analysis of Human Alu Genes," *J. Mol. Evolution* 32:105–121 (1991).*

Kern et al., "Identification of p53 as a Sequence–Specific DNA–Binding Protein," *Science* 252:1708–1711 (1991).*

Klemetti, A., "The Dexamethason Provocative Test: A Predictive Tool For Glaucoma?," *Acta Ophthamol.* 68:29–33 (1990).*

Komher, J.S. et al., "Mutation Detection Using Nucleotide Analogs That Alter Electrophoretic Mobility," *Nucl. Acids. Res.* 17:7779–7784 (1989).*

Kuppuswamy, M.N. et al., "Single Nucleotide Primer Extension to Detect Genetic Diseases: Experimental Application to Hemophilia B (Factor IX) and Cystic Fibrosis Genes," *Proc. Natl. Acad. Sci.* (*U.S.A.*) 88:1143–1147 (1991).*

Kwoh, D.Y., et al., "Transcription–Based Amplificaiton System and Detection of Amplified Human Immunodefiency Virus Type 1 With A Bead–Based Sandwhich Hybridization Format," *Proc. Natl. Acad. Sci.* U.S.A., 86:1173–1177 (1989).*

Landergren, Ulf, et al., "A Ligase–Mediated Gene Detection Technique," *Science* 241:1017–1080 (1988).*

Langer, R. et al., "Controlled Release of Macromolecules," *Chem. Tech.* 12:98 (1982).*

Lathe R., "Synthetic Oligonucleotide Probes Deduced From Amino Acid Sequence Data—Theoretical and Practical Considerations," *Journal of Molecular Biology,* 183:1–12 (1985).*

Lenardo et al., "NF–$_K$B: A Pleiotropic Mediator of Inducible and Tissue–Specific Gene Control," *Cell* 58:227–229 (1989).*

Lenardo et al., "Protein–Binding Sites in Ig Gene Enhancers Determine Transcriptional Activity and Inducibility," *Science* 236:1573–1577 (1987).*

Linderson et al., "NFE, A New Transcriptional Activator That Facilitates P50 and c–Rel–dependent IgH 3' Enhancer Activity," *European J. Immunology* 27:468–475 (1997).*

Moore, S.S. et al., "The Conservation of Dinucleotide Microsatellites Among Mammalian Genomes Allows the Use of Heterologous PCR Primer Pairs in Closely Related Species," *Genomics* 10:654–660 (1991).*

Mullis, K. et al., "Specific Enzymatic Amplification of DNA In Vitro: The Polymerase Chain Reaction," *Cold Spring Harbor Symp. Quant. Biol.* 51:263–273 (1986).*

Murnane et al., "Use of a Mammalian Interspersed Repetitive (MIR) Element in the Coding and Processing Sequences of Mammalian Genes," *Nucleic Acids Research* 15:2837–2839 (1995).*

Muscat et al., "A Common Factor Regulates Skeletal and Cardiac α–Actin Gene Transcription in Muscle," *Molecular and Cellular Biology* 10: 4120–4133 (1988).*

Nguyen, T.D. et al., "Cloning of glucocorticoid–induced proteins in HTM cells: verification of progressive, high dose dependent, cDNAs to correlate with effects on IOP," *Invest. Opthalmol. Vis Sci.* 32:789 (1990).*

Nguyen, T. D. et al., "Molecular Biology Studies of Steroid–Induced Glaucoma Model Using Cultured Human Trabecular Meshwork," *Invest Ophthalmol* Vis. Sci. 32789 (1991).*

Nguyen, T.D. et al., (In: "*Basic Aspects of Glaucoma Research III",* Schattauer, New York, 331–343 (1993).*

Nickerson, Deborah A., et al., "Automated DNA Diagnostics Using An ELISA–Based Oligonucleotide Ligation Assay," *Proc. Natl. Acad. Sci.* U.S.A., 87:8923–8927 (1990).*

Nyrén, P. et al., "Solid Phase DNA Minisequencing by an Enzymatic Luminometric Inorganic Pyrophosphate Detection Assay," *Anal. Biochem.* 208:171–175 (1993).*

Ohara, O. et al., "One–sided Polymerase Chain Reaction: The Amplification of cDNA," *Proc. Natl. Acad. Sci.* (*U.S.A.*) 86:5673–5677 (1989).*

Ortego, Javier, Cloning and Characterization of Subtracted cDNAs from a Human Ciliary Body Libray Encoding TIGR, a Protein Involved in Juvenile Open Angle Glaucoma With Homology to Ayosin and Olfactomedin, *FEBS Letters* 413:349–353 (1997).*

Partridge et al., "Dexamethasone Induces Specific Proteins in Human Trabecular Meshwork Cells," *Invest. Opthamol. Visual Sci.* 30(8):1843–1847 (1989).*

Polansky, J.R. et al., "Glucocorticoid Receptors and Steroid Glaucoma Mechanisms," *Encounters in Glaucoma Research 1:Receptor Biology and Glaucoma,* Fogliazza Editore, Milan pp. 273–299 (1994).*

Polansky, J.R. et al., "Growth Factor Effects and Modulation of Glucocorticoid (GC) and Other Stress Responses in Human Tradecular Meshwork (HTM) Cells," *Exp. Eye Research* 55:Ab 265 (1992).*

Polansky, J.R., et al., "In Vitro Correlates of Glucocorticoid Effects on Intraocular Pressure," In: *Glaucoma Update* IV, Springer–Verlag, Berlin, pp. 20–29 (1991).*

Polansky, J.R., In: "*Basic Aspects of Glaucoma Research III",* Schattauer, New York 307–318 (1993).*

Polansky, J.R., et al., Human Trabecular Meshwork Inducible Glucocorticoid Response Protein mRNA, Abstract (1997).*

Polansky, J.R. et al, "Cellular Mechanisms Influencing the Aqueous Outflow Pathway," In: Principles and Practice of Ophthalmology, Albert, D.M et al., Eds., .B. Saunders & Co. Philadelphia, pp. 226–251 (1994).*

Polansky, J.R. et al, "Eicosanoid Production and Glucocorticoid Regulatory Mechanisms in Cultured Human Trabecular Meshwork Cells," *Prog Clin Biol Res* 312:113–138 (1989).*

Polansky, J.R. et al., "Studies on Human Trabecular Cells Propagated In Vitro," *Vision Research* 21155–160 (1981).*

Polansky, J.R. "Side Effects of Topical Ophthalmic Therapy With Anti Inflammatory Steroids and β–Blockers," *Current Opinion In Ophthalmology* 3:259–272 (1992).*

Polansky, J.R. et al., "Cellular Pharmacology and Molecular Biology of the Trabecular Meshwork Inducible Glucocorticoid Response Gene Product," *Ophthalmologica* 211:126–139 (1997).*

Resnick et al., "Platelet–derived Growth Factor B Chain Promotor Contains a Cis–Acting Fluid Shear–Stress–Responsive Element," *Proc. Natl. Acad. Sci.* (*USA*) 80: 4591–4595 (1993).*

Rychlik, Wojciech et al., "A Computer Program For Choosing Optimal Oligonucleotides For Filter Hybridization, Sequencing and In Vitro Amplification of DNA," *Nucleic Acids Research,* 17:8543–8551 (1989).*

Schildkraut, Carl et al., "Dependence of the Melting Temperature of DNA on Salt Concentration," *Biopolymers,* 3:195–208 (1965).*

Sidman, U. et al., "Controlled Release of Macromolecules and Pharmaceuticals from Synthetic Polypeptides Based on Glutamic Acid," *Biopolymers* 22:547 (1983).*

Snyder et al., "Olfactomedin: Purification, Characterization, and Localization of a Novel Olfactory Glycoprotein," *Biochemistry* 30:9143–9153 (1991).*

Stone, E.M. et al. "Identification of a Gene That Causes Primary Open Angle Glaucoma," *Science* 275:668–670 (1997).*

Syvänen, A.C., et al., "A Primer–Guided Nucleotide Incorporation Assay in the Genotyping of Apolipoprotein E," *Genomics* 8:684–692 (1990).*

Tuck, M.W. et al., "Relative Effectiveness of Different Modes of Glaucoma Screening In Optometric Practice," *Ophthal. Physiol. Opt.* 13:227–232 (1993).*

Ugozzoli, L. et al., "Detection of Specific Alleles By Using Allele–Specific Primer Extension Followed By Capture On Solid Support," *GATA* 9:107–112 (1992).*

Vaughan, D. et al., In: *General Ophthalmology,* Appleton & Lange, Norwalk, CT, pp. 213–230 (1992).*

Vernon, S.A., "Intra–Eye Pressure Range and Pulse Profiles In Normals With The Pulsair Non–Contact Tonometer," *Eye* 7:134–137 (1993).*

Von der Ahe et al., "Glucocorticoid and Progesterone Receptors Bind to the Same Sites in Two Hormonally Regulated Promoters," *Nature* 313:706–709 (1985).*

Vriz et al., "The Sry Protein, Like HMG 1, Recognizes (CA)n Sequences, An Abundant Repeat Sequence In Vertebrates," *Biochemistry and Molecular Biology International* 37: 1137–1146 (1995).*

Walker, G.T. et al., *Proc. Natl. Acad. Sci.* (*U.S.A.*) 89:392–396 (1992).*

Weinreb, R.N. et al., Detection of Glucocorticoid Receptors in Cultured Human Trabecular Cells, *Invest Ophthalmol. Vis. Sci.* 21:403–407 (1981).*

Wickstrom et al., "Human Promyelocytic Leukemia HL–60 Cell Proliferation and c–myc Protein Expression Are Inhibited by An Antisense Pentadecadeoxynucleotide Targeted Against c–myc mRNA," *Proc. Natl. Acad. Sci.* (*U.S.A.*) 85:1028.*

Wu, D.Y. et al., *Genomics* 4:560 (1989).*

Yokoe and Anholt, "Molecular Cloning Of Olfactomedin, An Extracellular Matrix Protein Specific To Olfactory Neuroepithelium," *Proc. Natl. Acad. Sci.* 90:4655–4659 (1993).*

Yun, A.J., et al., "Proteins Secreted By Human Trabecular Cells," *Invest. Ophthalmol. Vis. Sci.* 30:2012–2022 (1989).*

Zhan, G.L. et al., *Exper. Eye Res.* 54:211–218 (1992).*

Escribano, J. et al., "Isolation and Characterization of Cell–Specific cDNA Clones from a Subtractive Library of the Ocular Cileary Body of a Single Normal Human Donor: Transcription and Synthesis of Plasma Proteins." J. Biochem. 118(5):921–931 (1995).*

Sunden, S.L.F. et al., Fine Mapping of the Autosomal Dominant Juvenile Open Angel Glaucoma (GLC1A) Region and Evaluation of Candidate Genes.: Genome Res. 6(9):862–869 (1996).*

Stone, E.M. et al., "Identification of a Gene that Caused Primary Open Angle Glaucoma." Science 275(31):668–670 (1997).*

Baumhueter et al., "A variant nuclear protein in dedifferentiated haptoma cells binds to the same functional sequences in the b fibrinogen gene bromoter as HNF–1," EMBO J., 7(8):2485–93(1988).*

Beato, "Gene regulation by steroid hormones," Cell, 56:335–44 (1989).*

Becker et al., "In Vivo protein—DNA interacitons in a glucocorticoid response element require the presence of the hormone," Nature, 324:686–88 (1986).*

Chen et al., "Identification of a TIGR Promoter Sequence Variant, TIGR.mt1, in a POAG Pedigree and Estimation of its Frequencey in Adult POAG," Abstract #3156, Association for Research in Vision and Ophthalmology Meeting (1998).*

Chen et al., "Identification of a TIGR Promoter Sequence Variantin Steroid Responders and Evidence for a Glucocorticoid–induced DNA Binding Protein of the TIGR Gene in TM Cells" Abstract #2666, Association for Research in Vision and Ophthalmology Meeting (1999).*

Chodosh et al., "Human CCAAT–Binding Proteins have heterologous subunits," Cell, 53:11–24 (1988).*

Coles et al., "An H1 histone gene–specific 5' element and evolution of H1 and H5 genes," Nucleic Acids Research, 13:585–94 (1985).*

Comb et al., "CpG methylation inhibits proenkephalin gene expression and binding of the transcription factor AP–2," Nucleic Acids Research, 18:3975–82 (1990).*

Courtois et al., "Nuclear factor–1 and activator protein–2 bind in a mutually exclusive way to overlapping promoter sequences and trans–activate the human growth hormone gene," Nucleic Acids Research, 18:57–64 (1990).* deVerneuil et al., "The lack of transcriptional activation of the v–erb A oncogene is in part due to a mutation present in the DNA binding domain of the protein," Nucleic Acids Research, 18:4489–97 (1990).* deWet et al., "Firefly luciferase gene: structure and expression in mammalian cells," Molecular and Cellular Biology, 7:725–37 (1987).*

Evans, "The steroid and thyroid hormone receptor superfamily," Science, 240:889–895 (1988).*

Faisst et al., "Compilation of vertebrate–encoded transcription factors," Nucleic Acids Research, 20:3–26 (1992).*

Forman et al., "Interactions among a subfamily of nuclear hormone receptors: the regulatory zipper model," Molecular Endocrinology, 4:1293–1301 (1990).*

Gaub et al., "Activation of the ovalbumin gene by the estrogen receptor involves the fos–jun complex," Cell, 63:1267–76 (1990).*

Glass et al., "The thyroid hormone receptor binds with opposite transcriptional effects to a common sequence motif in thyroid hormone and estrogen response elements," Cell, 54:313–23 (1988)*

Goyal et al., "Analysis of multiple forms of nuclear factor I in human and murine cell lines," Molecular and cellular biology, 10:1041–48 (1990).*

Gronostajski et al., "Site–specific DNA binding of nuclear factor I: Analyses of cellular binding sites," Molecular and Cellular Biology, 5:964–71 (1985).*

Harada et al., "Absence of the Type 1 IFN system in EC cells: transcriptional activator (IRF–1) and repressor (IRF–2) genes are developmentally regulated," Cell 63:303–12 (1990).*

Henninghausen et al., "Nuclaer factor 1 interacts with five DNA elements in the promoter region of the human cytomegalovirus major immediate early gene," EMBO J., 5:167–71 (1986).*

Imam et al., "Transcription factors induced by interferons a and g," Nucleic Acids Research, 18:6573–80 (1990).*

Jefferson et al., "GUS fusions: b–glucuronidase as a sensitive and versatile gene fusion marker in higher plants," EMBO J. 6:3901–07 (1987).*

Jones et al., "Trans–acting protein factors and the regulation of eukaryotic transcription: lessons from studies on DNA tumor viruses," Genes and Development, 2:267–81 (1988).*

Kim et al., "Autoinduction of transforming growth factor b1 is mediated by the AP–1 complex," Molecular and Cellular Biology, 10:1492–92 (1990).*

Kitazawa et al., "The prognosis of corticosteroid–responsive individuals" Arch. Ophthalmol. 99:819–23 (1981).*

Lee et al., "Mutational analysis by a combined application of the multiple restriction fragment–sibngle strand conformation polymorphism and the direct linear amplification DNA sequencing protocols," Analytical Biochemistry, 205:289–93 (1992).*

Lewis et al., "Intraocular pressure response to topical dexamethasone as a predictor for the development of primary open angle glaucoma" Am. J. Ophthalmol. 106:607–12 (1988).*

Liberman et al., "Involvement of a second lymphoid–spcific enhancer element in the regulation of immunoglobulin heavy–chain gene expression," Molecular and Cellular Biology, 10:3155–62 (1990).*

Lo et al., "Analysis of complex genetic systems by ARMS–SSCP: application to HLA genotyping," Nucleic Acids Research, 20:1005–09 (1992).*

Martin et al., "Activation of the polyomavirus enhancer by a murine activator protein 1 (AP1) homolog and two contiguous proteins," Proc. Natl. Acad. Sci. (USA), 85:5839–43 (1988).*

Mermod et al., "Enhancer binding factors AP–4 and AP–1 act in concert to activate SV40 late transcription in vitro," Nature, 332:557–61 (1988).*

Mitchell, et al., "Transcription factor AP–2 is expressed in neural crest cell lineages during mounse embryogenesis," Genes and Development, 5:105–19 (1991).*

Nguyen et al., "A TIGR (or MYOC, GLC1A) Gene Promoter Polymorphism Associates with Steroid–Glaucoma and Evidence for its Tissue Specific Expression in the Human Trabecular Meshwork Cells" Abstract #422, American Society of Human Genetics Meeting (1999).*

Nguyen et al., "Gene structure and properties of TIGR, an olfactomedin–related glycoprotein cloned from glucocorticoid–induced trabecular meshwork cells" J. Biol. Chem. 273:6341–50 (1998).*

Nguyen et al., "Mutation Anayses of the TIGR (Trabecular Meshwork Inducible Glucocorticoid Response) Promoter in a POAG Pedigree" Abstract #1999, American Society of Human Genetics Meeting (1997).*

Orita et al., "Rapid and sensitive detection of point mutations and DNA polymorphisms using the polymerase chain reaction," Genomics, 5:874–79 (1989).*

Pine et al., "Purification and coling of inteferon–stimulated gene factor 2 (ISGF2): ISGF2 (IRF–1) can bind to the promoters of both beta interferon– and interferon–stimulated genes but is not a primary transcriptional activator of either," Molecular and Cellualr Biology, 10:23448–2457 (19990).*

Prezant et al., "Trapped Oligonucleotide Nulceotide Incorporation (TONI) assay, a simple method for screening point mutations," Hum. Mutat. 1:159–64 (1992).*

Rajnarayan et al., "Reconstitution of Protein Kinase a regulation of the rat prolactin promoter in HeLa nonpituitary cells: identification of both GHF–1/Pit–1–dependent and –independent mechanisms," Molecular Endochronology 4:502–12 (1995).*

Redondo et al., "A T cell–specific transcriptional enhancer within the human T cell receptor & locus," Science, 247:1225–28 (1990).*

Regec et al., "The cloning and characterization of the human transcobalamin II gene," Blook 85:2711–2719 (1995).*

Rossi et al., "A nuclear factor 1 binding site mediates the transcriptional activation of a type 1 collagen promoter by transforming growth factor–b," Cell, 52:405–14 (1988).*

Sakai et al., "Hormone–mediated repression: a negative glucocorticoid response element from the bovine prolactin gene," Genes & Development, 2:1144–54 (1988).*

Sambrook et al., In: "Molecular cloning, laboratory manual, 2nd edition" Cold Spring Harbor Press, Cold Spring Harbor, NY (1989).*

Sarkar, et al., "Dideoxy fingerprinting (ddF): A rapid and efficient screen for the presence of mutations," Genomics, 13:441–43 (1992).*

Shirayoshi et al., "Interferon–induced transcription of a major histocompatibility class I gene accompanies binding of inducible nuclear factors to the interferon consensus sequence," Proc. Natl. Acad. Sci. (USA) 85:5884–88 (1988).*

Shore et al., "Identification of silencer binding proteins from yeast: possible roles in SIR control and DNA replication," EMBO J., 6:461–67 (1987).*

Stanojevic et al., "Regulation of a segmentation struipe by overlapping activators and repressors in the drosophila embryo," Science, 254:1385–87 (1991).*

Suzuki et al., "Allele–specific polymerase chain reaction: a method for amplification and sequence determination of a single component among a mixture of sequence variants," Analytical Biochemistry, 192:82–84 (1991).*

Taniguchi et al., "Interaction site of *Escherichia coli* cycli AMP receptor protein on DNA of galactose operon promoters," Poc. Natl. Acad. Sci. (USA) 76:5090–94 (1979).*

West et al., "Interaction of a tissue–specific factor with an essential rat growth hormone gene promoter element," Molecular and Celluar Biology, 7:1193–97 (1987).*

Williams et al., "Analysis of the DNA–binding and activation properties of the human transcription factor AP–2," Genes and Development, 5:670–82 (1991).*

Winning et al., "Developmental regulation of transcription factor AP–2 during *xenopus laevis* embryogenesis," Nucleic Acids Research, 19:3709–14 (1991).*

Yu–Lee et al., "Interferon–regulatory factor 1 is an immediate–early gene under transcriptional regulation by prolactin in Nb2 T cells," Molecular and Cellular Biology, 10:3087–94 (1990).*

Nguyen et. al., "Molecular Biology and Genetic Studies of the Major Extracellular Glucocorticoid(GC)–Induced Glycoprotein Cloned from the Human Trabecular Meshwork (HTM) Cells," Abstract, ARVO meeting, (1997).*

English translation of EP 0 158 277.*

Kubota R et al., "Genomic organisation of the human myocilin gene (MYOC) responsible for primary open angle glaucoma," Biochemical and Biophysical Research Communications, US, Academic Press Inc., vol. 242, No. 242, 1998, pp. 396–400.*

* cited by examiner

```
1                                          ATC TTTGTTCAGT TTACCTCAGG GCTATTATGA  33

34 AATGAAATGA GATAACCAAT GTGAAAGTCC TATAAACTGT ATAGCCTCCA TTCGGATGTA  93

94 TGTCTTTGGC AGGATGATAA AGAATCAGGA AGAAGGAGTA TCCACGTTAG CCAAGTGTCC  153

154 AGGCTGTGTC TGCTCTTATT TTAGTGACAG ATGTTGCTCC TGACAGAAGC TATTCTTCAG 213

214 GAAACATCAC ATCCAATATG GTAAATCCAT CAAACAGGAG CTAAGAAACA GGAATGAGAT 273

274 GGGCACTTGC CCAAGGAAAA ATGCCAGGAG AGCAAATAAT GATGAAAAAT AAACTTTTCC 333

334 CTTTGTTTTT AATTTCAGGA AAAAATGATG AGGACCAAAA TCAATGAATA AGGAAAAACAG 393
                         (Prl.FPIII) CCTG AAAATGAATA AGAAA

394 CTCAGAAAAA AGATGTTTCC AAATTGGTAA TTAAGTATTT GTTCCTTGGG AAGAGACCTC 453
                         (PR/GR-MMTV) T GTTCTTTTGG AA
                                            (SSRE)  GAGACC

454 CATGTGAGCT TGATGGGAAA ATGGGAAAAA CGTCAAAAGC ATGATCTGAT CAGATCCCAA 513

514 AGTGGATTAT TATTTTAAAA ACCAGATGGC ATCACTCTGG GGAGGCAAGT TCAGGAAGGT 573

574 CATGTTAGCA AAGGACATAA CAATAACAGC AAAATCAAAA TTCCGCAAAT GCAGGAGGAA 633
    CCTTTTAG-A AAGGACAAAA CAGAATG (nGRE-PRL)

634 AATGGGGACT GGGAAAGCTT TCATAACAGT GATTAGGCAG TTGACCATGT TCGCAACACC 693

694 TCCCCGTCTA TACCAGGGAA CACAAAAATT GACTGGGCTA AGCCTGGACT TTCAAGGGAA 753
                                            GCCTGGACT GTC (CBE-P53)

754 ATATGAAAAA CTGAGAGCAA AACAAAAGAC ATGGTTAAAA GGCAACCAGA ACATTGTGAG 813
                          ATTTTTCTGA TTGGTTAAAA GT (NFEi)

814 CCTTCAAAGC AGCAGTGCCC CTCAGCAGGG ACCCTGAGGC ATTTGCCTTT AGGAAGGCCA 873
                                   G ACCCTGAGGC T (KTF.1-CS)

874 GTTTTCTTAA GGAATCTTAA GAAACTCTTG AAAGATCATG AATTTTAACC ATTTTAAGTA 933

934 TAAAACAAAT ATGCGATGCA TAATCAGTTT AGACATGGGT CCCAATTTTA TAAAGTCAGG 993
                                          (PRE-lysozyme) AGGCCGT

994 CATACAAGGA TAACGTGTCC CAGCTCCGGA TAGGTCAGAA ATCATTAGAA ATCACTGTGT 1053
    GATCCAAGGA GCAGAAGTTC CAGCTATGGT CAG      (GRE-hMT) GG TACACTGTGT

1054 CCCCATCCTA ACTTTTTCAG AATGATCTGT CATAGCCCTC ACACACAGGC CCGATGTGTC 1113
CCT

1114 TGACCTACAA CCACATCTAC AACCCAAGTG CCTCAACCAT TGTTAACGTG TCATCTCAGT 1173
```

FIG.1A

```
1174 AGGTCCCATT ACAAATGCCA CCTCCCCTGT GCAGCCCATC CCGCTCCACA GGAAGTCTCC 1233

1234 CCACTCTAGA CTTCTGCATC ACGATGTTAC AGCCAGAAGC TCCGTGAGGG TGAGGGTCTG 1293
                                                    (SSRE) GGTCTC

1294 TGTCTTACAC CTACCTGTAT GCTCTACACC TGAGCTCACT GCAACCTCTG CCTCCCAGGT 1353

1354 TCAAGCAATT CTCCTGTCTC AGCCTCCCGC GTAGCTGGGA CTACAGGCGC ACGCCCGGCT 1413
                         C AGCCCCCCGC GCAGC (ETF.EGFR)

1414 AATTTTTGTA TTGTTAGTAG AGATGGGGTT TCACCATATT AGCCCGGCTG GTCTTGAACT 1473
        Alu Repeat Region                CCATATT AGG (SRE-cFos)

1474 CCTGACCTCA GGTGATCCAC CCACCTCAGC CTCCTAAAGT GCTGGGATTA CAGGCATGAG 1533

1534 TCACCGCGCC CGGCCAAGGG TCAGTGTTTA ATAAGGAATA ACTTGAATGG TTTACTAAAC 1593

1594 CAACAGGGAA ACAGACAAAA GCTGTGATAA TTTCAGGGAT TCTTGGGATG GGGAATGGTG 1653

1654 CCATGAGCTG CCTGCCTAGT CCCAGACCAC TGGTCCTCAT CACTTTCTTC CCTCATCCTC 1713

1714 ATTTTCAGGC TAAGTTACCA TTTTATTCAC CATGCTTTTG TGGTAAGCCT CCACATCGTT 1773

1774 ACTGAAATAA GAGTATACAT AAACTAGTTC CATTTGGGGC CATCTGTGTG TGTGTATAGG 1833
             GTTTACAT AAAC (VBP-vitel)                               GG

1834 GGAGGAGGGC ATACCCCAGA GACTCCTTGA AGCCCCCGGC AGAGGTTTCC TCTCCAGCTG 1893
     GGAKGAGG (MalT-CS)

1894 GGGGAGCCCT GCAAGCACCC GGGGTCCTGG GTGTCCTGAG CAACCTGCCA GCCCGTGCCA 1953

1954 CTGGTTGTTT TGTTATCACT CTCTAGGGAC CTGTTGCTTT CTATTTCTGT GTGACTCGTT 2013

2014 CATTCATCCA GGCATTCATT GACAATTTAT TGAGTACTTA TATCTGCCAG ACACCAGAGA 2073

2074 CAAAATGGTG AGCAAAGCAG TCACTGCCCT ACCTTCGTGG AGGTGACAGT TTCTCATGGA 2133

2134 AGACGTGCAG AAGAAAATTA ATAGCCAGCC AACTTAAACC CAGTGCTGAA AGAAAGGAAA 2193
                                     GCGTGAC CGGAGCTGAA AGAAAGGAAC

2194 TAAACACCAT CTTGAAGAAT TGTGCGCAGC ATCCCTTAAC AAGGCCACCT CCCTAGCGCC 2253
     AC (ERE-c.vitel)

2254 CCCTGCTGCC TCCATCGTGC CCGGAGGCCC CCAAGCCCGA GTCTTCCAAG CCTCCTCCTC 2313

2314 CATCAGTCAC AGCGCTGCAG CTGGCCTGCC TCGCTTCCcG TGAATCGTCC TGGTGCATCT 2373
                AGCAG CTGGC (NF-mutagen)

2374 GAGCTGGAGA CTCCTTGGCT CCAGGCTCCA GAAAGGAAAT GGAGAGGGAA ACTAGTCTAA 2433
                                A GAAAGGGAAA GGA (PRF-myc)

2434 CGGAGAATCT GGAGGGGACA GTGTTTCCTC AGAGGGAAAG GGGCCTCCAC GTCCAGGAGA 2493
                ACCCGGTACA CTGTGTCCTC CCGCT (GRE-hMT.IIa)
             CC CTTTGGGCCA ATGTGTCCTG AGGGGA (GRE-hGH)
```

FIG.1B

```
2494 ATTCCAGGAG GTGGGGACTG CAGGGAGTGG GGACGCTGGG GCTGAGCGGG TGCTGAAAGG 2553
                                 CTGG GGAGCCTGGG GA (AP.2-SV40)

2554 CAGGAAGGTG AAAAGGGCAA GGCTGAAGCT GCCCAGATGT TCAGTGTTGT TCACGGGGCT 2613

2614 GGGAGTTTTC CGTTGCTTCC TGTGAGCCTT TTTATCTTTT CTCTGCTTGG AGGAGAAGAA 2673
             CT CGTTGCTTCG AG (HSTF-hsp70)

2674 GTCTATTTCA TGAAGGGATG CAGTTTCATA AAGTCAGCTG TTAAAATTCC AGGGTGTGCA 2733
                                                                   A

2734 TGGGTTTTCC TTCACGAAGG CCTTTATTTA ATGGGAATAT AGGAAGCGAG CTCATTTCCT 2793
     TGGGTTTTTG (SBF.yeast)

2794 AGGCCGTTAA TTCACGGAAG AAGTGACTGG AGTCTTTTCT TTCATGTCTT CTGGGCAACT 2853

2854 ACTCAGCCCT GTGGTGGACT TGGCTTATGC AAGACGGTCG AAAACCTTGG AATCAGGAGA 2913

2914 CTCGGTTTTC TTTCTGGTTC TGCCATTGGT TGGCTGTGCG ACCGTGGGCA AGTGTCTCTC 2973
              C TTTCTGGTTT TGCAG (NF.1-bithorax)
                 (NF-MHCII/)CCATTGGT T

2974 CTTCCCTGGG CCATAGTCTT CTCTGCTATA AAGACCCTTG CAGCTCTCGT GTTCTGTGAA 3033

3034 CACTTCCCTG TGATTCTCTG TGAGGGGGGA TGTTGAGAGG GGAAGGAGGC AGAGCTGGAG 3093

3094 CAGCTGAGCC ACAGGGGAGG TGGAGGGGGA CAGGAAGGCA GGCAGAAGCT GGGTGCTCCA 3153

3154 TCAGTCCTCA CTGATCACGT CAGACTCCAG GACCGAGAGC CACAATGCTT CAGGAAAGCT 2943

2944 CAATGAACCC AACAGCCACA TTTTCCTTCC CTAAGCATAG ACAATGGCAT TTGCCAATAA 3273

3274 CCAAAAAGAA TGCAGAGACT AACTGGTGGT AGCTTTTGCC TGGCATTCAA AAACTGGGCC 3333
                GAAGTGACT AACTG (PEA.1-Polyoma)

3334 AGAGCAAGTG GAAAATGCCA GAGATTGTTA AACTTTTCAC CCTGACCAGC ACCCCACGCA 3393

3394 GCTCAGCAGT GACTGCTGAC AGCACGGAGT GACCTGCAGC GCAGGGGAGG AGAAGAAAAA 3453
                        C AGGTCAGAGT GACCTG (ERE.2-Vitel.)

3454 GAGAGGGATA GTGTATGAGC AAGAAAGACA GATTCATTCA AGGGCAGTGG GAATTGACCA 3513

3514 CAGGGATTAT AGTCCACGTG ATCCTGGGTT CTAGGAGGCA GGGCTATATT GTGGGGGGAA 3573
                (GRE-FLV) CGGGATAC CGAGAGAACA GGGCTATAGG

3574 AAAATCAGTT CAAGGGAAGT CGGGAGACCT GATTTCTAAT ACTATATTTT TCCTTTACAA 3633
                              GAGACC (SSRE)

3634 GCTGAGTAAT TCTGAGCAAG TCACAAGGTA GTAACTGAGG CTGTAAGATT ACTTAGTTTC 3693
                                          (ICS-MTII/ HLA-DR/)AGTTTC

3694 TCCTTATTAG GAACTCTTTT TCTCTGTGGA GTTAGCAGCA CAAGGGCAAT CCCGTTTCTT 3753
     TCCTCT

3754 TTAACAGGAA GAAAACATTC CTAAGAGTAA AGCCAAACAG ATTCAAGCCT AGGTCTTGCT 3813

3814 GACTATATGA TTGGTTTTTT GAAAAATCAT TTCAGCGATG TTTACTATCT GATTCAGAAA 3873
```

FIG.1C

```
3874 ATGAGACTAG TACCCTTTGG TCAGCTGTAA ACAAACACCC ATTTGTAAAT GTCTCAAGTT 3933
                      GG TCA (1/2 ERE)

3934 CAGGCTTAAC TGCAGAACCA ATCAAATAAG AATAGAATCT TTAGAGCAAA CTGTGTTTCT 3993

3994 CCACTCTGGA GGTGAGTCTG CCAGGGCAGT TTGGAAATAT TTACTTCACA AGTATTGACA 4053

4054 CTGTTGTTGG TATTAACAAC ATAAAGTTGC TCAAAGGCAA TCATTATTTC AAGTGGCTTA 4113

4114 AAGTTACTTC TGACAGTTTT GGTATATTTA TTGGCTATTG CCATTTGCTT TTTGTTTTTT 4173
                      (NF.1-HCMV)TTGGCTATTG GCCA             CTTT

4174 CTCTTTGGGT TTATTAATGT AAAGCAGGGA TTATTAACCT ACAGTCCAGA AAGCCTGTGA 4233
     CTCTTT (ISGF2)

4234 ATTTGAATGA GGAAAAAATT ACATTTTTGT TTTTACCACC TTCTAACTAA ATTTAACATT 4293
                                             (Zn binding)---------

4294 TTATTCCATT GCGAATAGAG CCATAAACTC AAAGTGGTAA TAACAGTACC TGTGATTTTG 4353

4354 TCATTACCAA TAGAAATCAC AGACATTTTA TACTATATTA CAGTTGTTGC AGATACGTTG 4413
                   (CAP-gal0) ATTTA TTCCATGTCA CACTTTTCGC A

4414 TAAGTGAAAT ATTTATACTC AAAACTACTT TGAAATTAGA CCTCCTGCTG GATCTTGTTT 4473
                 TTACTC A (AP-1)

4474 TTAACATATT AATAAAACAT GTTTAAAATT TTGATATTTT GATAATCATA TTTCATTATC 4533
                    GAT GTTTAAAAT (PRL-FPII)

4534 ATTTGTTTCC TTTGTAATCT ATATTTTATA TATTTGAAAA CATCTTTCTG AGAAGAGTTC 4593
                                (GRE-MuRFV) TGTTTTTCTG AGAACATCAG

4594 CCCAGATTTC ACCAATGAGG TTCTTGGCAT GCACACACAC AGAGTAAGAA CTGATTTAGA 4653
      CCAGATCTC ACCATCATTAT (nGRE)     CACACACAC A (CACA)
CTCTGG                                    GGACAC AGAGTAGGG (AP.1-TGFb)

4654 GGCTAACATT GACATTGGTG CCTGAGATGC AAGACTGAAA TTAGAAAGTT CTCCCAAAGA 4713
                         (GC2) GATGCT GATGGATAAT TTAGAAGCTT CTCCCACA

4714 TACACAGTTG TTTTAAAGCT AGGGGTGAGG GGGGAAATCT GCCGCTTCTA TAGGAATGCT 4773
                                                   (PEA.3)AGGAA GGT_

4774 CTCCCTGGAG CCTGGTAGGG TGCTGTCCTT GTGTTCTGGC TGGCTGTTAT TTTTCTCTGT 4833
    CTC (SSRE)             MIR Repeat Region

4834 CCCTGCTACG TCTTAAAGGA CTTGTTTGGA TCTCCAGTTC CTAGCATAGT GCCTGGCACA 4893
                    GGA CTTGTTTGTT CT (GRE-rTAT-II)        TGGGCACA
                GCAAAAAGGA TCTATTTGGA A (GRE-MMTV)

4894 GTGCAGGTTC TCAATGAGTT TGCAGAGTGA ATGGAAATAT AAACTAGAAA TATATCCTTG 4953
     GTGCCAA (NF-1          (HNF-1)C TGTGAAATAT TAACTAAA

4954 TTGAAATCAG CACACCAGTA GTCCTGGTGT AAGTGTGTGT ACGTGTGTGT GTGTGTGTGT 5013
```

FIG. 1D

```
5014 GTGTGTGTGT AAAACCAGGT GGAGATATAG GAACTATTAT TGGGGTATGG GTGCATAAAT 5073
                                                           cat/reverse cat box

5074 TGGGATGTTC TTTTTAAAAA GAAACTCCAA ACAGACTTCT GGAAGGTTAT TTTCTAAGAA 5133
  (1/2GRE)TGTTC T       (HSTF)          GAAACTTCT GGAATATTCC CGAACTTTC
                C CTTTTAGAAA GGA---CAAA ACAGAATG(nGRE-Prl)

5134 TCTTGCTGGC AGCGTGAAGG CAACCCCCCT GTGCACAGCC CCACCCAGCC TCACGTGGCC 5193
                (1/2 TRE)AGG CAA             T-CC CCAGGCTCCC -CAG(AP.2-SV40)
                                   GGAGAGCC CC (NF-KB)

5194 ACCTCTGTCT TCCCCCATGA AGGGCTGGCT CCCCAGTATA TATAAACCTC TCTGGAGCTC 5253
                                             tata box GGTC TC (SSRE)

5254 GGGCATGAGC CAGCAAGGC*C* ACCCATCCAG GCACCTCTCA GCACAGC 5300
                     Start Sites
```

FIG.1E

```
1                                                ATC TTTGTTCAGT TTACCTCAGG GCTATTATGA 33
34 AATGAAATGA GATAACCAAT GTGAAAGTCC TATAAACTGT ATAGCCTCCA TTCGGATGTA 93
94 TGTCTTTGGC AGGATGATAA AGAATCAGGA AGAAGGAGTA TCCACGTTAG CCAAGTGTCC 153
154 AGGCTGTGTC TGCTCTTATT TTAGTGACAG ATGTTGCTCC TGACAGAAGC TATTCTTCAG 213
214 GAAACATCAC ATCCAATATG GTAAATCCAT CAAACAGGAG CTAAGAAACA GGAATGAGAT 273
274 GGGCACTTGC CCAAGGAAAA ATGCCAGGAG AGCAAATAAT GATGAAAAAT AAACTTTTCC 333
334 CTTTGTTTTT AATTTCAGGA AAAAATGATG AGGACCAAAA TCAATGAATA AGGAAAACAG 393
394 CTCAGAAAAA AGATGTTTCC AAATTGGTAA TTAAGTATTT GTTCCTTGGG AAGAGACCTC 453
454 CATGTGAGCT TGATGGGAAA ATGGGAAAAA CGTCAAAAGC ATGATCTGAT CAGATCCCAA 513
514 AGTGGATTAT TATTTTAAAA ACCAGATGGC ATCACTCTGG GGAGGCAAGT TCAGGAAGGT 573
574 CATGTTAGCA AAGGACATAA CAATAACAGC AAAATCAAAA TTCCGCAAAT GCAGGAGGAA 633
634 AATGGGGACT GGGAAAGCTT TCATAACAGT GATTAGGCAG TTGACCATGT TCGCAACACC 693
694 TCCCCGTCTA TACCAGGGAA CACAAAAATT GACTGGGCTA AGCCTGGACT TTCAAGGGAA 753
754 ATATGAAAAA CTGAGAGCAA AACAAAAGAC ATGGTTAAAA GGCAACCAGA ACATTGTGAG 813
814 CCTTCAAAGC AGCAGTGCCC CTCAGCAGGG ACCCTGAGGC ATTTGCCTTT AGGAAGGCCA 873
874 GTTTTCTTAA GGAATCTTAA GAAACTCTTG AAAGATCATG AATTTTAACC ATTTTAAGTA 933
934 TAAAACAAAT ATGCGATGCA TAATCAGTTT AGACATGGGT CCCAATTTTA TAAAGTCAGG 993
994 CATACAAGGA TAACGTGTCC CAGCTCCGGA TAGGTCAGAA ATCATTAGAA ATCACTGTGT 1053
1054 CCCCATCCTA ACTTTTTCAG AATGATCTGT CATAGCCCTC ACACACAGGC CCGATGTGTC 1113
1114 TGACCTACAA CCACATCTAC AACCCAAGTG CCTCAACCAT TGTTAACGTG TCATCTCAGT 1173
1174 AGGTCCCATT ACAAATGCCA CCTCCCCTGT GCAGCCCATC CCGCTCCACA GGAAGTCTCC 1233
1234 CCACTCTAGA CTTCTGCATC ACGATGTTAC AGCCAGAAGC TCCGTGAGGG TGAGGGTCTG 1293
1294 TGTCTTACAC CTACCTGTAT GCTCTACACC TGAGCTCACT GCAACCTCTG CCTCCCAGGT 1353
1354 TCAAGCAATT CTCCTGTCTC AGCCTCCCGC GTAGCTGGGA CTACAGGCGC ACGCCCGGCT 1413
1414 AATTTTTGTA TTGTTAGTAG AGATGGGGTT TCACCATATT AGCCCGGCTG GTCTTGAACT 1473
```

FIG.2A

1474 CCTGACCTCA GGTGATCCAC CCACCTCAGC CTCCTAAAGT GCTGGGATTA CAGGCATGAG 1533
1534 TCACCGCGCC CGGCCAAGGG TCAGTGTTTA ATAAGGAATA ACTTGAATGG TTTACTAAAC 1593
1594 CAACAGGGAA ACAGACAAAA GCTGTGATAA TTTCAGGGAT TCTTGGGATG GGGAATGGTG 1653
1654 CCATGAGCTG CCTGCCTAGT CCCAGACCAC TGGTCCTCAT CACTTTCTTC CCTCATCCTC 1713
1714 ATTTTCAGGC TAAGTTACCA TTTTATTCAC CATGCTTTTG TGGTAAGCCT CCACATCGTT 1773
1774 ACTGAAATAA GAGTATACAT AAACTAGTTC CATTTGGGGC CATCTGTGTG TGTGTATAGG 1833
1834 GGAGGAGGGC ATACCCCAGA GACTCCTTGA AGCCCCCGGC AGAGGTTTCC TCTCCAGCTG 1893
1894 GGGGAGCCCT GCAAGCACCC GGGGTCCTGG GTGTCCTGAG CAACCTGCCA GCCCGTGCCA 1953
1954 CTGGTTGTTT TGTTATCACT CTCTAGGGAC CTGTTGCTTT CTATTTCTGT GTGACTCGTT 2013
2014 CATTCATCCA GGCATTCATT GACAATTTAT TGAGTACTTA TATCTGCCAG ACACCAGAGA 2073
2074 CAAAATGGTG AGCAAAGCAG TCACTGCCCT ACCTTCGTGG AGGTGACAGT TTCTCATGGA 2133
2134 AGACGTGCAG AAGAAAATTA ATAGCCAGCC AACTTAAACC CAGTGCTGAA AGAAAGGAAA 2193
2194 TAAACACCAT CTTGAAGAAT TGTGCGCAGC ATCCCTTAAC AAGGCCACCT CCCTAGCGCC 2253
2254 CCCTGCTGCC TCCATCGTGC CCGGAGGCCC CCAAGCCCGA GTCTTCCAAG CCTCCTCCTC 2313
2314 CATCAGTCAC AGCGCTGCAG CTGGCCTGCC TCGCTTCCCG TGAATCGTCC TGGTGCATCT 2373
2374 GAGCTGGAGA CTCCTTGGCT CCAGGCTCCA GAAAGGAAAT GGAGAGGGAA ACTAGTCTAA 2433
2434 CGGAGAATCT GGAGGGGACA GTGTTTCCTC AGAGGGAAAG GGGCCTCCAC GTCCAGGAGA 2493
2494 ATTCCAGGAG GTGGGGACTG CAGGGAGTGG GGACGCTGGG GCTGAGCGGG TGCTGAAAGG 2553
2554 CAGGAAGGTG AAAAGGGCAA GGCTGAAGCT GCCCAGATGT TCAGTGTTGT TCACGGGGCT 2613
2614 GGGAGTTTTC CGTTGCTTCC TGTGAGCCTT TTTATCTTTT CTCTGCTTGG AGGAGAAGAA 2673
2674 GTCTATTTCA TGAAGGGATG CAGTTTCATA AAGTCAGCTG TTAAAATTCC AGGGTGTGCA 2733
2734 TGGGTTTTCC TTCACGAAGG CCTTTATTTA ATGGGAATAT AGGAAGCGAG CTCATTTCCT 2793
2794 AGGCCGTTAA TTCACGGAAG AAGTGACTGG AGTCTTTTCT TTCATGTCTT CTGGGCAACT 2853
2854 ACTCAGCCCT GTGGTGGACT TGGCTTATGC AAGACGGTCG AAAACCTTGG AATCAGGAGA 2913
2914 CTCGGTTTTC TTTCTGGTTC TGCCATTGGT TGGCTGTGCG ACCGTGGGCA AGTGTCTCTC 2973
2974 CTTCCCTGGG CCATAGTCTT CTCTGCTATA AAGACCCTTG CAGCTCTCGT GTTCTGTGAA 3033
3034 CACTTCCCTG TGATTCTCTG TGAGGGGGGA TGTTGAGAGG GGAAGGAGGC AGAGCTGGAG 3093

FIG.2B

3094 CAGCTGAGCC ACAGGGGAGG TGGAGGGGGA CAGGAAGGCA GGCAGAAGCT GGGTGCTCCA 3153

3154 TCAGTCCTCA CTGATCACGT CAGACTCCAG GACCGAGAGC CACAATGCTT CAGGAAAGCT 2943

2944 CAATGAACCC AACAGCCCACA TTTTCCTTCC CTAAGCATAG ACAATGGCAT TTGCCAATAA 3273

3274 CCAAAAAGAA TGCAGAGACT AACTGGTGGT AGCTTTTGCC TGGCATTCAA AAACTGGGCC 3333

3334 AGAGCAAGTG GAAAATGCCA GAGATTGTTA AACTTTTCAC CCTGACCAGC ACCCCACGCA 3393

3394 GCTCAGCAGT GACTGCTGAC AGCACGGAGT GACCTGCAGC GCAGGGGAGG AGAAGAAAAA 3453

3454 GAGAGGGATA GTGTATGAGC AAGAAAGACA GATTCATTCA AGGGCAGTGG GAATTGACCA 3513

3514 CAGGGATTAT AGTCCACGTG ATCCTGGGTT CTAGGAGGCA GGGCTATATT GTGGGGGGAA 3573

3574 AAAATCAGTT CAAGGGAAGT CGGGAGACCT GATTTCTAAT ACTATATTTT TCCTTTACAA 3633

3634 GCTGAGTAAT TCTGAGCAAG TCACAAGGTA GTAACTGAGG CTGTAAGATT ACTTAGTTTC 3693

3694 TCCTTATTAG GAACTCTTTT TCTCTGTGGA GTTAGCAGCA CAAGGGCAAT CCCGTTTCTT 3753

3754 TTAACAGGAA GAAAACATTC CTAAGAGTAA AGCCAAACAG ATTCAAGCCT AGGTCTTGCT 3813

3814 GACTATATGA TTGGTTTTTT GAAAAATCAT TTCAGCGATG TTTACTATCT GATTCAGAAA 3873

3874 ATGAGACTAG TACCCTTTGG TCAGCTGTAA ACAAACACCC ATTTGTAAAT GTCTCAAGTT 3933

3934 CAGGCTTAAC TGCAGAACCA ATCAAATAAG AATAGAATCT TTAGAGCAAA CTGTGTTTCT 3993

3994 CCACTCTGGA GGTGAGTCTG CCAGGGCAGT TTGGAAATAT TTACTTCACA AGTATTGACA 4053

4054 CTGTTGTTGG TATTAACAAC ATAAAGTTGC TCAAAGGCAA TCATTATTTC AAGTGGCTTA 4113

4114 AAGTTACTTC TGACAGTTTT GGTATATTTA TTGGCTATTG CCATTTGCTT TTTGTTTTTT 4173

4174 CTCTTTGGGT TTATTAATGT AAAGCAGGGA TTATTAACCT ACAGTCCAGA AAGCCTGTGA 4233

4234 ATTTGAATGA GGAAAAAATT ACGTTTTTAT TTTTACCACC TTCTAACTAA ATTTAACATT 4293

4294 TTATTCCATT GCGAATAGAG CCATAAACTC AAAGTGGTAA TAAGAGTACC TGTGATTTTG 4353

4354 TCATTACCAA TAGAAATCAC AGACATTTTA TACTATATTA CAGTTGTTGC AGGTACGTTG 4413

4414 TAAGTGAAAT ATTTATACTC AAAACTACTT TGAAATTAGA CCTCCTGCTG GATCTTGTTT 4473

4474 TTAACATATT AATAAAACAT GTTTAAAATT TTGATATTTT GATAATCATA TTTCATTATC 4533

4534 ATTTGTTTCC TTTGTAATCT ATATTTTATA TATTTGAAAA CATCTTTCTG AGAAGAGTTC 4593

4594 CCCAGATTTC ACCAATGAGG TTCTTGGCAT GCACACACAC AGAGTAAGAA CTGATTTAGA 4653

4654 GGCTAACATT GACATTGGTG CCTGAGATGC AAGACTGAAA TTAGAAAGTT CTCCCAAAGA 4713

FIG.2C

4714 TACACAGTTG TTTTAAAGCT AGGGGTGAGG GGGGAAATCT GCCGCTTCTA TAGGAATGCT 4773

4774 CTCCCTGGAG CCTGGTAGGG TGCTGTCCTT GTGTTCTGGC TGGCTGTTAT TTTTCTCTGT 4833

4834 CCCTGCTACG TCTTAAAGGA CTTGTTTGGA TCTCCAGTTC CTAGCATAGT GCCTGGCACA 4893

4894 GTGCAGGTTC TCAATGAGTT TGCAGAGTGA ATGGAAATAT AAACTAGAAA TATATCTTTG 4953

4954 TTGAAATCAG CACACCAGTA GTCCTGGTGT AAGTGTGTGT ACGTGTGTGTGTGT GTGTGTGTGT5017

5018 GTGTGTGTGT AAAACCAGGT GGAGATATAG GAACTATTAT TGGGGTATGG GTGCATAAAT 5077

5078 TGGGATGTTC TTTTTAAAAA GAAACTCCAA ACAGACTTCT GGAAGGTTAT TTTCTAAGAA 5137

5138 TCTTGCTGGC AGCGTGAAGG CAACCCCCCT GTGCACAGCC CCACCCAGCC TCACGTGGCC 5197

5198 ACCTCTGTCT TCCCCCATGA AGGGCTGGCT CCCCAGTATA TATAAACCTC TCTGGAGCTC 5257

5258 GGGCATGAGC CAGCAAGGCC ACCCATCCAG GCACCTCTCA GCACAGC 5304

FIG.2D

1 ATCTTTGTTC AGTTTACCTC AGGGCTATTA TGAAATGAAA TGAGATAACC

51 AATGTGAAAG TCCTATAAAC TGTATAGCCT CCATTCGGAT GTATGTCTTT

101 GGCAGGATGA TAAAGAATCA GGAAGAAGGA GTATCCACGT TAGCCAAGTG

151 TCCAGGCTGT GTCTGCTCTT ATTTTAGTGA CAGATGTTGC TCCTGACAGA

201 AGCTATTCTT CAGGAAACAT CACATCCAAT ATGGTAAATC CATCAAACAG

251 GAGCTAAGAA ACAGGAATGA GATGGGCACT TGCCCAAGGA AAAATGCCAG

301 GAGAGCAAAT AATGATGAAA AATAAACTTT TCCCTTTGTT TTTAATTTCA

351 GGAAAAAATG ATGAGGACCA AAATCAATGA ATAAGGAAAA CAGCTCAGAA

401 AAAAGATGTT TCCAAATTGG TAATTAAGTA TTTGTTCCTT GGGAAGAGAC

451 CTCCATGTGA GCTTGATGGG AAAATGGGAA AAACGTCAAA AGCATGATCT

501 GATCAGATCC CAAAGTGGAT TATTATTTTA AAAACCAGAT GGCATCACTC

551 TGGGGAGGCA AGTTCAGGAA GGTCATGTTA GCAAAGGACA TAACAATAAC

601 AGCAAAATCA AAATTCCGCA AATGCAGGAG GAAAATGGGG ACTGGGAAAG

651 CTTTCATAAC AGTGATTAGG CAGTTGACCA TGTTCGCAAC ACCTCCCCGT

701 CTATACCAGG GAACACAAAA ATTGACTGGG CTAAGCCTGG ACTTTCAAGG

751 GAAATATGAA AAACTGAGAG CAAAACAAAA GACATGGTTA AAAGGCAACC

801 AGAACATTGT GAGCCTTCAA AGCAGCAGTG CCCCTCAGCA GGGACCCTGA

851 GGCATTTGCC TTTAGGAAGG CCAGTTTTCT TAAGGAATCT TAAGAAACTC

901 TTGAAAGATC ATGAATTTTA ACCATTTTAA GTATAAAACA AATATGCGAT

951 GCATAATCAG TTTAGACATG GGTCCCAATT TTATAAAGTC AGGCATACAA

1001 GGATAACGTG TCCCAGCTCC GGATAGGTCA GAAATCATTA GAAATCACTG

1051 TGTCCCCATC CTAACTTTTT CAGAATGATC TGTCATAGCC CTCACACACA

1101 GGCCCGATGT GTCTGACCTA CAACCACATC TACAACCCAA GTGCCTCAAC

1151 CATTGTTAAC GTGTCATCTC AGTAGGTCCC ATTACAAATG CCACCTCCCC

1201 TGTGCAGCCC ATCCCGCTCC ACAGGAAGTC TCCCCACTCT AGACTTCTGC

1251 ATCACGATGT TACAGCCAGA AGCTCCGTGA GGGTGAGGGT CTGTGTCTTA

FIG.3A

```
1301 CACCTACCTG TATGCTCTAC ACCTGAGCTC ACTGCAACCT CTGCCTCCCA
1351 GGTTCAAGCA ATTCTCCTGT CTCAGCCTCC CGCGTAGCTG GGACTACAGG
1401 CGCACGCCCG GCTAATTTTT GTATTGTTAG TAGAGATGGG GTTTCACCAT
1451 ATTAGCCCGG CTGGTCTTGA ACTCCTGACC TCAGGTGATC CACCCACCTC
1501 AGCCTCCTAA AGTGCTGGGA TTACAGGCAT GAGTCACCGC GCCCGGCCAA
1551 GGGTCAGTGT TTAATAAGGA ATAACTTGAA TGGTTTACTA AACCAACAGG
1601 GAAACAGACA AAAGCTGTGA TAATTTCAGG GATTCTTGGG ATGGGGAATG
1651 GTGCCATGAG CTGCCTGCCT AGTCCCAGAC CACTGGTCCT CATCACTTTC
1701 TTCCCTCATC CTCATTTTCA GGCTAAGTTA CCATTTTATT CACCATGCTT
1751 TTGTGGTAAG CCTCCACATC GTTACTGAAA TAAGAGTATA CATAAACTAG
1801 TTCCATTTGG GGCCATCTGT GTGTGTGTAT AGGGGAGGAG GGCATACCCC
1851 AGAGACTCCT TGAAGCCCCC GGCAGAGGTT TCCTCTCCAG CTGGGGGAGC
1901 CCTGCAAGCA CCCGGGGTCC TGGGTGTCCT GAGCAACCTG CCAGCCCGTG
1951 CCACTGGTTG TTTTGTTATC ACTCTCTAGG GACCTGTTGC TTTCTATTTC
2001 TGTGTGACTC GTTCATTCAT CCAGGCATTC ATTGACAATT TATTGAGTAC
2051 TTATATCTGC CAGACACCAG AGACAAAATG GTGAGCAAAG CAGTCACTGC
2101 CCTACCTTCG TGGAGGTGAC AGTTTCTCAT GGAAGACGTG CAGAAGAAAA
2151 TTAATAGCCA GCCAACTTAA ACCCAGTGCT GAAAGAAAGG AAATAAACAC
2201 CATCTTGAAG AATTGTGCGC AGCATCCCTT AACAAGGCCA CCTCCCTAGC
2251 GCCCCCTGCT GCCTCCATCG TGCCCGGAGG CCCCCAAGCC CGAGTCTTCC
2301 AAGCCTCCTC CTCCATCAGT CACAGCGCTG CAGCTGGCCT GCCTCGCTTC
2351 CCGTGAATCG TCCTGGTGCA TCTGAGCTGG AGACTCCTTG GCTCCAGGCT
2401 CCAGAAAGGA AATGGAGAGG GAAACTAGTC TAACGGAGAA TCTGGAGGGG
2451 ACAGTGTTTC CTCAGAGGGA AAGGGGCCTC CACGTCCAGG AGAATTCCAG
2501 GAGGTGGGGA CTGCAGGGAG TGGGGACGCT GGGGCTGAGC GGGTGCTGAA
2551 AGGCAGGAAG GTGAAAAGGG CAAGGCTGAA GCTGCCCAGA TGTTCAGTGT
2601 TGTTCACGGG GCTGGGAGTT TTCCGTTGCT TCCTGTGAGC CTTTTTATCT
```

FIG.3B

2651 TTTCTCTGCT TGGAGGAGAA GAAGTCTATT TCATGAAGGG ATGCAGTTTC
2701 ATAAAGTCAG CTGTTAAAAT TCCAGGGTGT GCATGGGTTT TCCTTCACGA
2751 AGGCCTTTAT TTAATGGGAA TATAGGAAGC GAGCTCATTT CCTAGGCCGT
2801 TAATTCACGG AAGAAGTGAC TGGAGTCTTT TCTTTCATGT CTTCTGGGCA
2851 ACTACTCAGC CCTGTGGTGG ACTTGGCTTA TGCAAGACGG TCGAAAACCT
2901 TGGAATCAGG AGACTCGGTT TTCTTTCTGG TTCTGCCATT GGTTGGCTGT
2951 GCGACCGTGG GCAAGTGTCT CTCCTTCCCT GGGCCATAGT CTTCTCTGCT
3001 ATAAAGACCC TTGCAGCTCT CGTGTTCTGT GAACACTTCC CTGTGATTCT
3051 CTGTGAGGGG GGATGTTGAG AGGGGAAGGA GGCAGAGCTG GAGCAGCTGA
3101 GCCACAGGGG AGGTGGAGGG GGACAGGAAG GCAGGCAGAA GCTGGGTGCT
3151 CCATCAGTCC TCACTGATCA CGTCAGACTC CAGGACCGAG AGCCACAATG
3201 CTTCAGGAAA GCTCAATGAA CCCAACAGCC ACATTTTCCT TCCCTAAGCA
3251 TAGACAATGG CATTTGCCAA TAACCAAAAA GAATGCAGAG ACTAACTGGT
3301 GGTAGCTTTT GCCTGGCATT CAAAAACTGG GCCAGAGCAA GTGGAAAATG
3351 CCAGAGATTG TTAAACTTTT CACCCTGACC AGCACCCCAC GCAGCTCAGC
3401 AGTGACTGCT GACAGCACGG AGTGACCTGC AGCGCAGGGG AGGAGAAGAA
3451 AAAGAGAGGG ATAGTGTATG AGCAAGAAAG ACAGATTCAT TCAAGGGCAG
3501 TGGGAATTGA CCACAGGGAT TATAGTCCAC GTGATCCTGG GTTCTAGGAG
3551 GCAGGGCTAT ATTGTGGGGG GAAAAAATCA GTTCAAGGGA AGTCGGGAGA
3601 CCTGATTTCT AATACTATAT TTTTCCTTTA CAAGCTGAGT AATTCTGAGC
3651 AAGTCACAAG GTAGTAACTG AGGCTGTAAG ATTACTTAGT TTCTCCTTAT
3701 TAGGAACTCT TTTTCTCTGT GGAGTTAGCA GCACAAGGGC AATCCCGTTT
3751 CTTTTAACAG GAAGAAAACA TTCCTAAGAG TAAAGCCAAA CAGATTCAAG
3801 CCTAGGTCTT GCTGACTATA TGATTGGTTT TTTGAAAAAT CATTTCAGCG
3851 ATGTTTACTA TCTGATTCAG AAAATGAGAC TAGTACCCTT TGGTCAGCTG
3901 TAAACAAACA CCCATTTGTA AATGTCTCAA GTTCAGGCTT AACTGCAGAA
3951 CCAATCAAAT AAGAATAGAA TCTTTAGAGC AAACTGTGTT TCTCCACTCT

FIG.3C

4001 GGAGGTGAGT CTGCCAGGGC AGTTTGGAAA TATTTACTTC ACAAGTATTG

4051 ACACTGTTGT TGGTATTAAC AACATAAAGT TGCTCAAAGG CAATCATTAT

4101 TTCAAGTGGC TTAAAGTTAC TTCTGACAGT TTTGGTATAT TTATTGGCTA

4151 TTGCCATTTG CTTTTTGTTT TTTCTCTTTG GGTTTATTAA TGTAAAGCAG

4201 GGATTATTAA CCTACAGTCC AGAAAGCCTG TGAATTTGAA TGAGGAAAAA

4251 ATTACATTTT TGTTTTTACC ACCTTCTAAC TAAATTTAAC ATTTTATTCC

4301 ATTGCGAATA GAGCCATAAA CTCAAAGTGG TAATAACAGT ACCTGTGATT

4351 TTGTCATTAC CAATAGAAAT CACAGACATT TTATACTATA TTACAGTTGT

4401 TGCAGATACG TTGTAAGTGA AATATTTATA CTCAAAACTA CTTTGAAATT

4451 AGACCTCCTG CTGGATCTTG TTTTTAACAT ATTAATAAAA CATGTTTAAA

4501 ATTTTGATAT TTTGATAATC ATATTTCATT ATCATTTGTT TCCTTTGTAA

4551 TCTATATTTT ATATATTTGA AAACATCTTT CTGAGAAGAG TTCCCCAGAT

4601 TTCACCAATG AGGTTCTTGG CATGCACACA CACAGAGTAA GAACTGATTT

4651 AGAGGCTAAC ATTGACATTG GTGCCTGAGA TGCAAGACTG AAATTAGAAA

4701 GTTCTCCCAA AGATACACAG TTGTTTTAAA GCTAGGGGTG AGGGGGGAAA

4751 TCTGCCGCTT CTATAGGAAT GCTCTCCCTG GAGCCTGGTA GGGTGCTGTC

4801 CTTGTGTTCT GGCTGGCTGT TATTTTTCTC TGTCCCTGCT ACGTCTTAAA

4851 GGACTTGTTT GGATCTCCAG TTCCTAGCAT AGTGCCTGGC ACAGTGCAGG

4901 TTCTCAATGA GTTTGCAGAG TGAATGGAAA TATAAACTAG AAATATATCC

4951 TTGTTGAAAT CAGCACACCA GTAGTCCTGG TGTAAGTGTG TGTACGTGTG

5001 TGTGTGTGTG TGTGTGTGTG TGTAAAACCA GGTGGAGATA TAGGAACTAT

5051 TATTGGGGTA TGGGTGCATA AATTGGGATG TTCTTTTTAA AAAGAAACTC

5101 CAAACAGACT TCTGGAAGGT TATTTTCTAA GAATCTTGCT GGCAGCGTGA

5151 AGGCAACCCC CCTGTGCACA GCCCCACCCA GCCTCACGTG GCCACCTCTG

5201 TCTTCCCCCA TGAAGGGCTG GCTCCCCAGT ATATATAAAC CTCTCTGGAG

5251 CTCGGGCATG AGCCAGCAAG GCCACCCATC CAGGCACCTC TCAGCACAGC 5300

FIG.3D

```
1 AGAGCTTTCCAGAGGAAGCCTCACCAAGCCTCTGCAATGAGGTTCTTCTGTGCACGTTGC 60

61 TGCAGCTTTGGGCCTGAGATGCCAGCTGTCCAGCTGCTGCTTCTGGCCTGCCTGGTGTGG 120

121 GATGTGGGGGCCAGGACAGCTCAGCTCAGGAAGGCCAATGACCAGAGTGGCCGATGCCAG 180

181 TATACCTTCAGTGTGGCCAGTCCCAATGAATCCAGCTGCCCAGAGCAGAGCCAGGCCATG 240

241 TCAGTCATCCATAACTTACAGAGAGACAGCAGCACCCAACGCTTAGACCTGGAGGCCACC 300

301 AAAGCTCGACTCAGCTCCCTGGAGAGCCTCCTCCACCAATTGACCTTGGACCAGGCTGCC 360

361 AGGCCCCAGGAGACCCAGGAGGGGCTGCAGAGGGAGCTGGGCACCCTGAGGCGGGAGCGG 420

421 GACCAGCTGGAAACCCAAACCAGAGAGTTGGAGACTGCCTACAGCAACCTCCTCCGAGAC 480

481 AAGTCAGTTCTGGAGGAAGAGAAGAAGCGACTAAGGCAAGAAAATGAGAATCTGGCCAGG 540

541 AGGTTGGAAAGCAGCAGCCAGGAGGTAGCAAGGCTGAGAAGGGGCCAGTGTCCCCAGACC 600

601 CGAGACACTGCTCGGGCTGTGCCACCAGGCTCCAGAGAAG

                         (intron #1) gtaagaatgcagagtgggggactct
 gagttcagcaggtgatatggctcgtagtgacctgctacaggcgctccaggcctccctgccctttctccta
 gagactgcacagctagcacaagacagatgaattaaggaaagcacacgatcaccttcaagtattacta
 gtaatttagctcctgagagcttcatttagattagtggttcagagttcttgtgcccctccatgtcag-----
 -----------------------   Intron I ~10 Kb---------------------------
 aaggtaggcacattgccctgcaatttataatttatgaggtgttcaattatggaattgtcaaatattaaca
 aaagtagagagactacaatgaactccaatgtagccataactcaggcccaactgttatcagcacagtcc
 aatcatgttttatctttccttctctgacccccaacccatccccagtccttatctaaaatcaaatatcaaaca
 ccatactctttgggagcctatttatttagttagttagttttcagacagagtttctttcttgttcccaagctgg
 agtacaatagtgtagtctcggctaacagcaatctccccctccttggttcaagcaattctcctgcctcagtc
 tcccaagaagctgggattatagacacctgccaccacatccagctaatttttttgtgttttagaaaagaca
 gggtttcaccatgttggccaggctggtttcgaactcctgacctcaggtgatccgcctgcctcggcctccca
 aagtgctgggattacaggcatgagccaccacgcctggccggcagcctatttaaatgtcatcctcaacat
 agtcaatccttgggccatttttttcttacagtaaaattttgtctctttcttttaatcag

                         (exon #2) TT TCT ACG TGG AAT TTG GAC

661 ACT TTG GCC TTC CAG GAA CTG AAG TCC GAG CTA ACT GAA GTT CCT GCT TCC CGA ATT TTG 720
721 AAG GAG AGC CCA TCT GGC TAT CTC AGG AGT GGA GAG GGA GAC ACCG

 (intron #2)
 gtatgaagttaagtttcttccccttttgtgcccacgtggtctttattcatgtctagtgctgtgttcagagaa
 tcagtatagggtaaatgcccacccaaggggaaattaacttccctgggagcagagggaggggagga
 gaagaggaacagaactctctctctctctgttacccttgt------Intron II ~ 3 kb-------
```

FIG.3E

```
tggctctgccaagcttccgcatgatcattgtctgtgtttggaagattatggattaagtggtgcttcgtttt
ctttctgaatttaccag
                                        (exon #3) GA TGT GGA GAA CTA 780

 781 GTT TGG GTA GGA GAG CCT CTC ACG CTG AGA ACA GCA GAA ACA ATT ACT GGC AAG TAT GGT 840
 841 GTG TGG ATG CGA GAC CCC AAG CCC ACC TAC CCC TAC ACC CAG GAG ACC ACG TGG AGA ATC 900
 901 GAC ACA GTT GGC ACG GAT GTC CGC CAG GTT TTT GAG TAT GAC CTC ATC AGC CAG TTT ATG 960
 961 CAG GGC TAC CCT TCT AAG GTT CAC ATA CTG CCT AGG CCA CTG GAA AGC ACG GGT GCT GTG 1020
1021 GTG TAC TCG GGG AGC CTC TAT TTC CAG GGC GCT GAG TCC AGA ACT GTC ATA AGA TAT GAG 1080
1081 CTG AAT ACC GAG ACA GTG AAG GCT GAG AAG GAA ATC CCT GGA GCT GGC TAC CAC GGA CAG 1140
1141 TTC CCG TAT TCT TGG GGT GGC TAC ACG GAC ATT GAC TTG GCT GTG GAT GAA GCA GGC CTC 1200
1201 TGG GTC ATT TAC AGC ACC GAT GAG GCC AAA GGT GCC ATT GTC CTC TCC AAA CTG AAC CCA 1260
1261 GAG AAT CTG GAA CTC GAA CAA ACC TGG GAG ACA AAC ATC CGT AAG CAG TCA GTC GCC AAT 1320
1321 GCC TTC ATC ATC TGT GGC ACC TTG TAC ACC GTC AGC AGC TAC ACC TCA GCA GAT GCT ACC 1380
1381 GTC AAC TTT GCT TAT GAC ACA GGC ACA GGT ATC AGC AAG ACC CTG ACC ATC CCA TTC AAG 1440
1441 AAC CGC TAT AAG TAC AGC AGC ATG ATT GAC TAC AAC CCC CTG GAG AAG AAG CTC TTT GCC 1500
1501 TGG GAC AAC TTG AAC ATG GTC ACT TAT GAC ATC AAG CTC TCC AAG ATG

                               (3' flanking region) TGA AAA GCC TCC 1560

1561 AAG CTG TAC AGG CAA TGG CAG AAG GAG ATG CTC AGG GCT CCT GGG GGG AGC AGG CTG AAG 1620
1621 GGA GAG CCA GCC AGC CAG GGC CCA GGC AGC TTT GAC TGC TTT CCA AGT TTT CAT TAA TCC 1680
1681 AGA AGG ATG AAC ATG GTC ACC ATC TAA CTA TTC AGG AAT TGT AGT CTG AGG GCG TAG ACA 1740
1741 ATT TCA TAT AAT AAA TAT CCT TTA TCT TCT GTC AGC ATT TAT GGG ATG TTT AAT GAC ATA 1800
1801 GTT CAA GTT TTC TTG TGA TTT GGG GCA AAA GCT GTA AGG CAT AAT AGT CTT TTC CTG AAA 1860
1861 ACC ATT GCT CTT GCA TGT TAC ATG GTT ACC ACA AGC CAC AAT AAA AAG CAT AAC TTC TAA 1920
1921 AGG AAG CAG AAT AGC TCC TCT GGC CAG CAT CGA ATA TAA GTA AGA TGC ATT TAC TAC AGT 1980
1981 TGG CTT CTA ATG CTT CAG ATA GAA TAC AGT TGG GTC TCA CAT AAC CCT TAC ATT GTG AAA 2040
2041 TAA AAT TTT CTT ACC CAA CGT TCT CTT CCT TGA ACT TTG TGG GAA TCT TTG CTT AAG AGA 2100
2101 AGG ATA TAG ATT CCA ACC ATC AGG TAA TTC CTT CAG GTT GGG AGA TGT GAT TGC AGG ATG 2160
```

FIG.3F

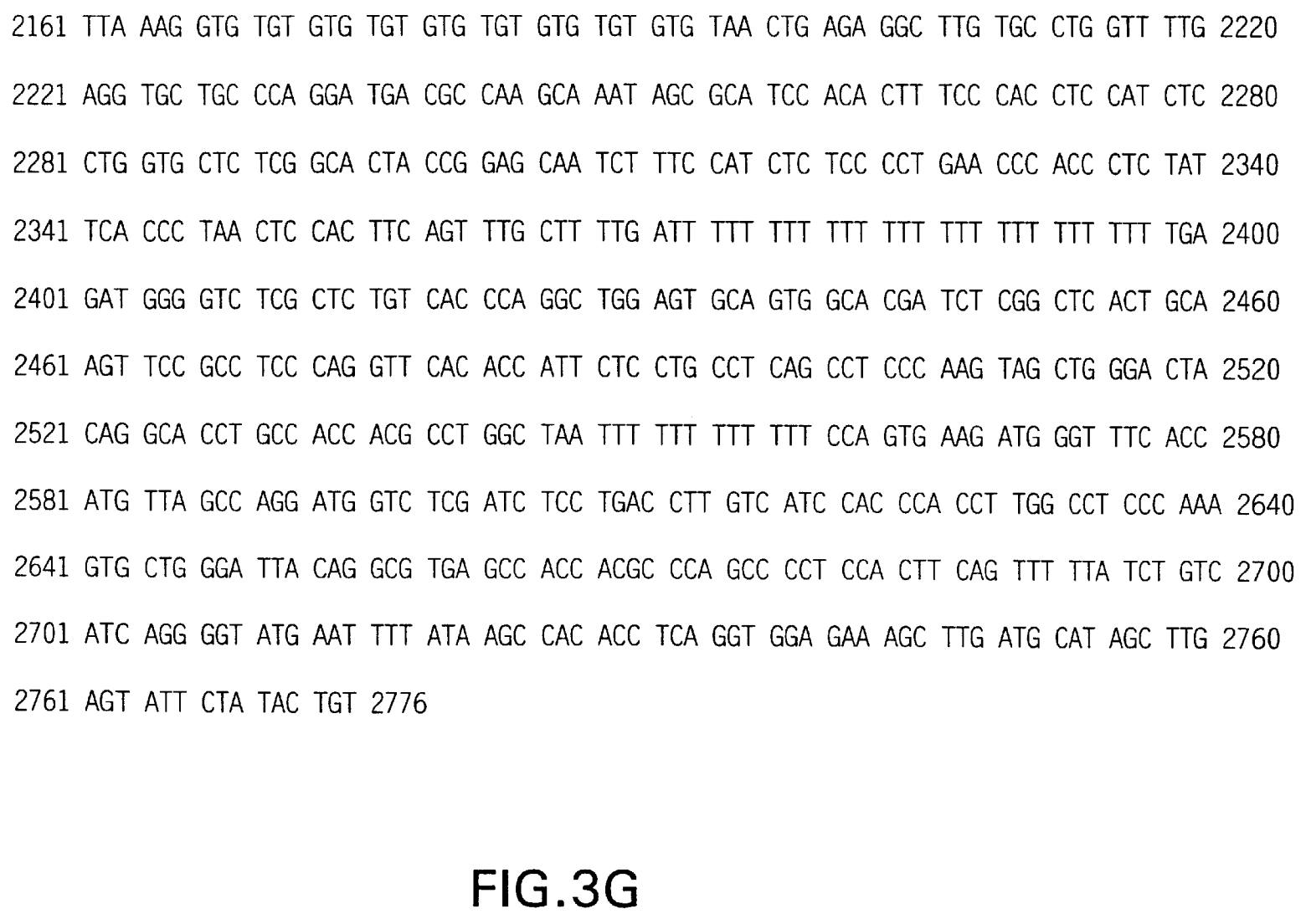

2161 TTA AAG GTG TGT GTG TGT GTG TGT GTG TGT GTG TAA CTG AGA GGC TTG TGC CTG GTT TTG 2220

2221 AGG TGC TGC CCA GGA TGA CGC CAA GCA AAT AGC GCA TCC ACA CTT TCC CAC CTC CAT CTC 2280

2281 CTG GTG CTC TCG GCA CTA CCG GAG CAA TCT TTC CAT CTC TCC CCT GAA CCC ACC CTC TAT 2340

2341 TCA CCC TAA CTC CAC TTC AGT TTG CTT TTG ATT TTT TTT TTT TTT TTT TTT TTT TTT TGA 2400

2401 GAT GGG GTC TCG CTC TGT CAC CCA GGC TGG AGT GCA GTG GCA CGA TCT CGG CTC ACT GCA 2460

2461 AGT TCC GCC TCC CAG GTT CAC ACC ATT CTC CTG CCT CAG CCT CCC AAG TAG CTG GGA CTA 2520

2521 CAG GCA CCT GCC ACC ACG CCT GGC TAA TTT TTT TTT TTT CCA GTG AAG ATG GGT TTC ACC 2580

2581 ATG TTA GCC AGG ATG GTC TCG ATC TCC TGAC CTT GTC ATC CAC CCA CCT TGG CCT CCC AAA 2640

2641 GTG CTG GGA TTA CAG GCG TGA GCC ACC ACGC CCA GCC CCT CCA CTT CAG TTT TTA TCT GTC 2700

2701 ATC AGG GGT ATG AAT TTT ATA AGC CAC ACC TCA GGT GGA GAA AGC TTG ATG CAT AGC TTG 2760

2761 AGT ATT CTA TAC TGT 2776

FIG.3G

```
TIGR        -TGAVVYSGS LYFQGAESRT VIRYELNTET VKAEKEIPGA GYHGQFPYSW GGYTDIDLAV 59
ym08h12.r1  ---------- ---------- --RFDLKTET ILKTRSLDYA GYNNMYHYAW GGHSDIDLMV 38
1B426bAMZ   GTGQVVYNGS IYFNKFQSHI IIRFDLKTET ILKTRSLDYA GYNNMYHYAW GGHSDIDLMV 60
ranofm      GAGVVVHNNN LYYNCFNSHD MCRASL-TSG VYQKKPLLNA LFNNRFSYAG TMFQDMDFSS 59
Consensus   ..G.VV.... .Y.....S.. ..R..L.TET ......L..A GYNN...YAW GG..DIDL.V 60

TIGR        DEAGLWVIYS TDEAKGAIVL SKLNPENLEL EQTWETNIRK QSVANAFIIC GTLYTVSSYT 119
ym08h12.r1  DESGLWAVYA TNQNAGNIVV SRLDPVSLQT LQTWNTSYPK RXPGXAFIIC GTCYVTNGY- 97
1B426bAMZ   DENGLWAVYA TNQNAGNIVI SKLDPVSLQI LQTWNTSYPK RSAGEAFIIC GTLYVTNGYS 120
ranofm      DEKGLWVIFT TEKSAGKIVV GKVNVATFTV DNIWITTQNK SDASNAFMIC GVLYVTRSLG 119
Consensus   DE.GLW..Y. T...AG.IV. SKL.P..L.. .QTW.T...K .....AFIIC GTLYVT..Y. 120

TIGR        SADATVNFAY DTGTGISKTL TIPFKNRYKY SSMIDYNPLE KKLFAWDNLN MVTYDIKLS  178
ym08h12.r1  SGGTKVHYAY QTNAST---- -------YEY ---IDI-PFQ NKLXP----- --HFPC---  131
1B426bAMZ   GG-TKVHYAY QTNASTYEYI DIPFQNKYSH ISMLDYNPKD RALYAWNNGH QTLYNVTLF  178
ranofm      PKMEEVFYMF DTKTGKEGHL SIMMEKMAEK VHSLSYNSND RKLYMFSEGY LLHYDIAL-  177
Consensus   .....V.YAY .T........ .I.....Y.. ....DYNP.. .KL....... ...Y...L.  178
```

FIG.6

```
  1 AGA GCT TTC CAG AGG AAG CCT CAC CAA GCC TCT GCA ATG AGG TTC TTC TGT GCA CGT TGC 60
 61 TGC AGC TTT GGG CCT GAG ATG CCA GCT GTC CAG CTG CTG CTT CTG GCC TGC CTG GTG TGG 120
121 GAT GTG GGG GCC AGG ACA GCT CAG CTC AGG AAG GCC AAT GAC CAG AGT GGC CGA TGC CAG 180
181 TAT ACC TTC AGT GTG GCC AGT CCC AAT GAA TCC AGC TGC CCA GAG CAG AGC CAG GCC ATG 240
241 TCA GTC ATC CAT AAC TTA CAG AGA GAC AGC AGC ACC CAA CGC TTA GAC CTG GAG GCC ACC 300
301 AAA GCT CGA CTC AGC TCC CTG GAG AGC CTC CTC CAC CAA TTG ACC TTG GAC CAG GCT GCC 360
361 AGG CCC CAG GAG ACC CAG GAG GGG CTG CAG AGG GAG CTG GGC ACC CTG AGG CGG GAG CGG 420
421 GAC CAG CTG GAA ACC CAA ACC AGA GAG TTG GAG ACT GCC TAC AGC AAC CTC CTC CGA GAC 480
481 AAG TCA GTT CTG GAG GAA GAG AAG AAG CGA CTA AGG CAA GAA AAT GAG AAT CTG GCC AGG 540
541 AGG TTG GAA AGC AGC AGC CAG GAG GTA GCA AGG CTG AGA AGG GGC CAG TGT CCC CAG ACC 600
601 CGA GAC ACT GCT CGG GCT GTG CCA CCA GGC TCC AGA GAA GTT TCT ACG TGG AAT TTG GAC 660
661 ACT TTG GCC TTC CAG GAA CTG AAG TCC GAG CTA ACT GAA GTT CCT GCT TCC CGA ATT TTG 720
721 AAG GAG AGC CCA TCT GGC TAT CTC AGG AGT GGA GAG GGA GAC ACC GGA TGT GGA GAA CTA 780
781 GTT TGG GTA GGA GAG CCT CTC ACG CTG AGA ACA GCA GAA ACA ATT ACT GGC AAG TAT GGT 840
841 GTG TGG ATG CGA GAC CCC AAG CCC ACC TAC CCC TAC ACC CAG GAG ACC ACG TGG AGA ATC 900
```

FIG. 7

```
901 GAC ACA GTT GGC ACG GAT GTC CGC CAG GTT TTT GAG TAT GAC CTC ATC AGC CAG TTT ATG 960
961 CAG GGC TAC CCT TCT AAG GTT CAC ATA CTG CCT AGG CCA CTG GAA AGC ACG GGT GCT GTG 1020
1021 GTG TAC TCG GGG AGC CTC TAT TTC CAG GGC GCT GAG TCC AGA ACT GTC ATA AGA TAT GAG 1080
1081 CTG AAT ACC GAG ACA GTG AAG GCT GAG AAG GAA ATC CCT GGA GCT GGC TAC CAC GGA CAG 1140
1141 TTC CCG TAT TCT TGG GGT GGC TAC ACG GAC ATT GAC TTG GCT GTG GAT GAA GCA GGC CTC 1200
1201 TGG GTC ATT TAC AGC ACC GAT GAG GCC AAA GGT GCC ATT GTC CTC TCC AAA CTG AAC CCA 1260
1261 GAG ATT CTG GAA CTC GAA CAA ACC TGG GAG ACA AAC ATC CGT AAG CAG TCA GTC GCC AAT 1320
1321 GCC TTC ATC ATC TGT GGC ACC TTG TAC ACC GTC AGC AGC TAC ACC TCA GCA GAT GCT ACC 1380
1381 GTC AAC TTT GCT TAT GAC ACA GGC ACA GGT ATC AGC AAG ACC CTG ACC ATC CCA TTC AAG 1440
1441 AAC CGC TAT AAG TAC AGC AGC ATG ATT GAC TAC ACC CCC CTG GAG AAG AAG CTC TTT GCC 1500
1501 TGG GAC AAC TTG AAC ATG GTC ACT TAT GAC ATC AAG CTC TCC AAG ATG 1548
```

FIG. 7 Cont.

```
1                                                   Met Arg Phe Phe Cys Ala Arg Cys 20
21 Cys Ser Phe Gly Pro Glu Met Pro Ala Val Gln Leu Leu Leu Leu Ala Cys Leu Val Trp 40
41 Asp Val Gly Ala Arg Thr Ala Gln Leu Arg Lys Ala Asn Asp Gln Ser Gly Arg Cys Gln 60
61 Tyr Thr Phe Ser Val Ala Ser Pro Asn Glu Ser Ser Cys Pro Glu Gln Ser Gln Ala Met 80
81 Ser Val Ile His Asn Leu Gln Arg Asp Ser Ser Thr Gln Arg Leu Asp Leu Glu Ala Thr 100
101 Lys Ala Arg Leu Ser Ser Leu Glu Ser Leu Leu His Gln Leu Thr Leu Asp Gln Ala Ala 120
121 Arg Pro Gln Glu Thr Gln Glu Gly Leu Gln Arg Glu Leu Gly Thr Leu Arg Arg Glu Arg 140
141 Asp Gln Leu Glu Thr Gln Thr Arg Glu Leu Glu Thr Ala Tyr Ser Asn Leu Leu Arg Asp 160
161 Lys Ser Val Leu Glu Glu Glu Lys Lys Arg Leu Arg Gln Glu Asn Glu Asn Leu Ala Arg 180
181 Arg Leu Glu Ser Ser Ser Gln Glu Val Ala Arg Leu Arg Arg Gly Gln Cys Pro gln Thr 200
201 Arg Asp Thr Ala Arg Ala Val Pro Pro Gly Ser Arg Glu Val Ser Thr Trp Asn Leu Asp 220
221 Thr Leu Ala Phe Gln Glu Leu Lys Ser Glu Leu Thr Glu Val Pro Ala Ser Arg Ile Leu 240
241 Lys Glu Ser Pro Ser Gly Tyr Leu Arg Ser Gly Glu Gly Asp Thr Gly Cys Gly Glu Leu 260
261 Val Trp Val Gly Glu Pro Leu Thr Leu Arg Thr Ala Glu Thr Ile Thr Gly Lys Tyr Gly 280
281 Val Trp Met Arg Asp Pro Lys Pro Thr Tyr Pro Tyr Thr Gln Glu Thr Thr Trp Arg Ile 300
```

FIG.8

301 Asp Thr Val Gly Thr Asp Val Arg Gln Val Phe Glu Tyr Asp Leu Ile Ser Gln Phe Met 320

321 Gln Gly Tyr Pro Ser Lys Val His Ile Leu Pro Arg Pro Leu Glu Ser Thr Gly Ala Val 340

341 Val Tyr Ser Gly Ser Leu Tyr Phe Gln Gly Ala Glu Ser Arg Thr Val Ile Arg Tyr Glu 360

361 Leu Asn Thr Glu Thr Val Lys Ala Glu Lys Glu Ile Pro Gly Ala Gly Tyr His Gly Gln 380

381 Phe Pro Tyr Ser Trp Gly Gly Tyr Thr Asp Ile Asp Leu Ala Val Asp Glu Ala Gly Leu 400

401 Trp Val Ile Tyr Ser Thr Asp Glu Ala Lys Gly Ala Ile Val Leu Ser Lys Leu Asn Pro 420

421 Glu Asn Leu Glu Leu Glu Gln Thr Trp Glu Thr Asn Ile Arg Lys Gln Ser Val Ala Asn 440

441 Ala Phe Ile Ile Cys Gly Thr Leu Tyr Thr Val Ser Ser Tyr Thr Ser Ala Asp Ala Thr 460

461 Val Asn Phe Ala Tyr Asp Thr Gly Thr Gly Ile Ser Lys Thr Leu Thr Ile Pro Phe Lys 480

481 Asn Arg Tyr Lys Tyr Ser Ser Met Ile Asp Tyr Asn Pro Leu Glu Lys Lys Leu Phe Ala 500

501 Trp Asp Asn Leu Asn Met Val Thr Tyr Asp Ile Lys Leu Ser Lys Met

FIG. 8 Cont.

SEQUENCE LISTING

```
(1) GENERAL INFORMATION:

   (iii) NUMBER OF SEQUENCES: 32

(2) INFORMATION FOR SEQ ID NO:1:

     (i) SEQUENCE CHARACTERISTICS:
          (A) LENGTH: 5300 base pairs
          (B) TYPE: nucleic acid
          (C) STRANDEDNESS: single
          (D) TOPOLOGY: linear

    (xi) SEQUENCE DESCRIPTION: SEQ ID NO:1:

ATCTTTGTTC AGTTTACCTC AGGGCTATTA TGAAATGAAA TGAGATAACC AATGTGAAAG     60

TCCTATAAAC TGTATAGCCT CCATTCGGAT GTATGTCTTT GGCAGGATGA TAAAGAATCA    120

GGAAGAAGGA GTATCCACGT TAGCCAAGTG TCCAGGCTGT GTCTGCTCTT ATTTTAGTGA    180

CAGATGTTGC TCCTGACAGA AGCTATTCTT CAGGAAACAT CACATCCAAT ATGGTAAATC    240

CATCAAACAG GAGCTAAGAA ACAGGAATGA GATGGGCACT TGCCCAAGGA AAAATGCCAG    300

GAGAGCAAAT AATGATGAAA AATAAACTTT TCCCTTTGTT TTTAATTTCA GGAAAAAATG    360

ATGAGGACCA AAATCAATGA ATAAGGAAAA CAGCTCAGAA AAAAGATGTT TCCAAATTGG    420

TAATTAAGTA TTTGTTCCTT GGGAAGAGAC CTCCATGTGA GCTTGATGGG AAAATGGGAA    480

AAACGTCAAA AGCATGATCT GATCAGATCC CAAAGTGGAT TATTATTTTA AAAACCAGAT    540

GGCATCACTC TGGGGAGGCA AGTTCAGGAA GGTCATGTTA GCAAAGGACA TAACAATAAC    600

AGCAAAATCA AAATTCCGCA AATGCAGGAG GAAAATGGGG ACTGGGAAAG CTTTCATAAC    660

AGTGATTAGG CAGTTGACCA TGTTCGCAAC ACCTCCCCGT CTATACCAGG GAACACAAAA    720

ATTGACTGGG CTAAGCCTGG ACTTTCAAGG GAAATATGAA AAACTGAGAG CAAAACAAAA    780

GACATGGTTA AAAGGCAACC AGAACATTGT GAGCCTTCAA AGCAGCAGTG CCCCTCAGCA    840

GGGACCCTGA GGCATTTGCC TTTAGGAAGG CCAGTTTTCT TAAGGAATCT TAAGAAACTC    900

TTGAAAGATC ATGAATTTTA ACCATTTTAA GTATAAAACA AATATGCGAT GCATAATCAG    960

TTTAGACATG GGTCCCAATT TTATAAAGTC AGGCATACAA GGATAACGTG TCCCAGCTCC   1020

GGATAGGTCA GAAATCATTA GAAATCACTG TGTCCCCATC CTAACTTTTT CAGAATGATC   1080

TGTCATAGCC CTCACACACA GGCCCGATGT GTCTGACCTA CAACCACATC TACAACCCAA   1140

GTGCCTCAAC CATTGTTAAC GTGTCATCTC AGTAGGTCCC ATTACAAATG CCACCTCCCC   1200

TGTGCAGCCC ATCCCGCTCC ACAGGAAGTC TCCCCACTCT AGACTTCTGC ATCACGATGT   1260
```

-continued

```
TACAGCCAGA AGCTCCGTGA GGGTGAGGGT CTGTGTCTTA CACCTACCTG TATGCTCTAC   1320
ACCTGAGCTC ACTGCAACCT CTGCCTCCCA GGTTCAAGCA ATTCTCCTGT CTCAGCCTCC   1380
CGCGTAGCTG GGACTACAGG CGCACGCCCG GCTAATTTTT GTATTGTTAG TAGAGATGGG   1440
GTTTCACCAT ATTAGCCCGG CTGGTCTTGA ACTCCTGACC TCAGGTGATC CACCCACCTC   1500
AGCCTCCTAA AGTGCTGGGA TTACAGGCAT GAGTCACCGC GCCCGGCCAA GGGTCAGTGT   1560
TTAATAAGGA ATAACTTGAA TGGTTTACTA AACCAACAGG GAAACAGACA AAAGCTGTGA   1620
TAATTTCAGG GATTCTTGGG ATGGGGAATG GTGCCATGAG CTGCCTGCCT AGTCCCAGAC   1680
CACTGGTCCT CATCACTTTC TTCCCTCATC CTCATTTTCA GGCTAAGTTA CCATTTTATT   1740
CACCATGCTT TTGTGGTAAG CCTCCACATC GTTACTGAAA TAAGAGTATA CATAAACTAG   1800
TTCCATTTGG GGCCATCTGT GTGTGTGTAT AGGGGAGGAG GGCATACCCC AGAGACTCCT   1860
TGAAGCCCCC GGCAGAGGTT TCCTCTCCAG CTGGGGGAGC CCTGCAAGCA CCCGGGGTCC   1920
TGGGTGTCCT GAGCAACCTG CCAGCCCGTG CCACTGGTTG TTTTGTTATC ACTCTCTAGG   1980
GACCTGTTGC TTTCTATTTC TGTGTGACTC GTTCATTCAT CCAGGCATTC ATTGACAATT   2040
TATTGAGTAC TTATATCTGC CAGACACCAG AGACAAAATG GTGAGCAAAG CAGTCACTGC   2100
CCTACCTTCG TGGAGGTGAC AGTTTCTCAT GGAAGACGTG CAGAAGAAAA TTAATAGCCA   2160
GCCAACTTAA ACCCAGTGCT GAAAGAAAGG AAATAAACAC CATCTTGAAG AATTGTGCGC   2220
AGCATCCCTT AACAAGGCCA CCTCCCTAGC GCCCCCTGCT GCCTCCATCG TGCCCGGAGG   2280
CCCCCAAGCC CGAGTCTTCC AAGCCTCCTC CTCCATCAGT CACAGCGCTG CAGCTGGCCT   2340
GCCTCGCTTC CCGTGAATCG TCCTGGTGCA TCTGAGCTGG AGACTCCTTG GCTCCAGGCT   2400
CCAGAAAGGA AATGGAGAGG GAAACTAGTC TAACGGAGAA TCTGGAGGGG ACAGTGTTTC   2460
CTCAGAGGGA AAGGGGCCTC CACGTCCAGG AGAATTCCAG GAGGTGGGGA CTGCAGGGAG   2520
TGGGGACGCT GGGGCTGAGC GGGTGCTGAA AGGCAGGAAG GTGAAAAGGG CAAGGCTGAA   2580
GCTGCCCAGA TGTTCAGTGT TGTTCACGGG GCTGGGAGTT TTCCGTTGCT TCCTGTGAGC   2640
CTTTTTATCT TTTCTCTGCT TGGAGGAGAA GAAGTCTATT TCATGAAGGG ATGCAGTTTC   2700
ATAAAGTCAG CTGTTAAAAT TCCAGGGTGT GCATGGGTTT TCCTTCACGA AGGCCTTTAT   2760
TTAATGGGAA TATAGGAAGC GAGCTCATTT CCTAGGCCGT TAATTCACGG AAGAAGTGAC   2820
TGGAGTCTTT TCTTTCATGT CTTCTGGGCA ACTACTCAGC CCTGTGGTGG ACTTGGCTTA   2880
TGCAAGACGG TCGAAAACCT TGGAATCAGG AGACTCGGTT TTCTTTCTGG TTCTGCCATT   2940
GGTTGGCTGT GCGACCGTGG GCAAGTGTCT CTCCTTCCCT GGGCCATAGT CTTCTCTGCT   3000
ATAAAGACCC TTGCAGCTCT CGTGTTCTGT GAACACTTCC CTGTGATTCT CTGTGAGGGG   3060
GGATGTTGAG AGGGGAAGGA GGCAGAGCTG GAGCAGCTGA GCCACAGGGG AGGTGGAGGG   3120
GGACAGGAAG GCAGGCAGAA GCTGGGTGCT CCATCAGTCC TCACTGATCA CGTCAGACTC   3180
CAGGACCGAG AGCCACAATG CTTCAGGAAA GCTCAATGAA CCCAACAGCC ACATTTTCCT   3240
TCCCTAAGCA TAGACAATGG CATTTGCCAA TAACCAAAAA GAATGCAGAG ACTAACTGGT   3300
GGTAGCTTTT GCCTGGCATT CAAAAACTGG GCCAGAGCAA GTGGAAAATG CCAGAGATTG   3360
TTAAACTTTT CACCCTGACC AGCACCCCAC GCAGCTCAGC AGTGACTGCT GACAGCACGG   3420
AGTGACCTGC AGCGCAGGGG AGGAGAAGAA AAAGAGAGGG ATAGTGTATG AGCAAGAAAG   3480
ACAGATTCAT TCAAGGGCAG TGGGAATTGA CCACAGGGAT TATAGTCCAC GTGATCCTGG   3540
GTTCTAGGAG GCAGGGCTAT ATTGTGGGGG GAAAAAATCA GTTCAAGGGA AGTCGGGAGA   3600
```

-continued

```
CCTGATTTCT AATACTATAT TTTTCCTTTA CAAGCTGAGT AATTCTGAGC AAGTCACAAG   3660

GTAGTAACTG AGGCTGTAAG ATTACTTAGT TTCTCCTTAT TAGGAACTCT TTTTCTCTGT   3720

GGAGTTAGCA GCACAAGGGC AATCCCGTTT CTTTTAACAG GAAGAAAACA TTCCTAAGAG   3780

TAAAGCCAAA CAGATTCAAG CCTAGGTCTT GCTGACTATA TGATTGGTTT TTTGAAAAAT   3840

CATTTCAGCG ATGTTTACTA TCTGATTCAG AAAATGAGAC TAGTACCCTT TGGTCAGCTG   3900

TAAACAAACA CCCATTTGTA AATGTCTCAA GTTCAGGCTT AACTGCAGAA CCAATCAAAT   3960

AAGAATAGAA TCTTTAGAGC AAACTGTGTT TCTCCACTCT GGAGGTGAGT CTGCCAGGGC   4020

AGTTTGGAAA TATTTACTTC ACAAGTATTG ACACTGTTGT TGGTATTAAC AACATAAAGT   4080

TGCTCAAAGG CAATCATTAT TTCAAGTGGC TTAAAGTTAC TTCTGACAGT TTTGGTATAT   4140

TTATTGGCTA TTGCCATTTG CTTTTTGTTT TTTCTCTTTG GGTTTATTAA TGTAAAGCAG   4200

GGATTATTAA CCTACAGTCC AGAAAGCCTG TGAATTTGAA TGAGGAAAAA ATTACATTTT   4260

TGTTTTTACC ACCTTCTAAC TAAATTTAAC ATTTTATTCC ATTGCGAATA GAGCCATAAA   4320

CTCAAAGTGG TAATAACAGT ACCTGTGATT TTGTCATTAC CAATAGAAAT CACAGACATT   4380

TTATACTATA TTACAGTTGT TGCAGATACG TTGTAAGTGA AATATTTATA CTCAAAACTA   4440

CTTTGAAATT AGACCTCCTG CTGGATCTTG TTTTTAACAT ATTAATAAAA CATGTTTAAA   4500

ATTTTGATAT TTTGATAATC ATATTTCATT ATCATTTGTT TCCTTTGTAA TCTATATTTT   4560

ATATATTTGA AAACATCTTT CTGAGAAGAG TTCCCCAGAT TTCACCAATG AGGTTCTTGG   4620

CATGCACACA CACAGAGTAA GAACTGATTT AGAGGCTAAC ATTGACATTG GTGCCTGAGA   4680

TGCAAGACTG AAATTAGAAA GTTCTCCCAA AGATACACAG TTGTTTTAAA GCTAGGGGTG   4740

AGGGGGGAAA TCTGCCGCTT CTATAGGAAT GCTCTCCCTG GAGCCTGGTA GGGTGCTGTC   4800

CTTGTGTTCT GGCTGGCTGT TATTTTTCTC TGTCCCTGCT ACGTCTTAAA GGACTTGTTT   4860

GGATCTCCAG TTCCTAGCAT AGTGCCTGGC ACAGTGCAGG TTCTCAATGA GTTTGCAGAG   4920

TGAATGGAAA TATAAACTAG AAATATATCC TTGTTGAAAT CAGCACACCA GTAGTCCTGG   4980

TGTAAGTGTG TGTACGTGTG TGTGTGTGTG TGTGTGTGTG TGTAAAACCA GGTGGAGATA   5040

TAGGAACTAT TATTGGGGTA TGGGTGCATA AATTGGGATG TTCTTTTTAA AAAGAAACTC   5100

CAAACAGACT TCTGGAAGGT TATTTTCTAA GAATCTTGCT GGCAGCGTGA AGGCAACCCC   5160

CCTGTGCACA GCCCCACCCA GCCTCACGTG GCCACCTCTG TCTTCCCCCA TGAAGGGCTG   5220

GCTCCCCAGT ATATATAAAC CTCTCTGGAG CTCGGGCATG AGCCAGCAAG GCCACCCATC   5280

CAGGCACCTC TCAGCACAGC                                               5300
```

(2) INFORMATION FOR SEQ ID NO:2:

(i) SEQUENCE CHARACTERISTICS:
(A) LENGTH: 5304 base pairs
(B) TYPE: nucleic acid
(C) STRANDEDNESS: single
(D) TOPOLOGY: linear (xi) SEQUENCE DESCRIPTION: SEQ ID NO:2:

```
ATCTTTGTTC AGTTTACCTC AGGGCTATTA TGAAATGAAA TGAGATAACC AATGTGAAAG     60

TCCTATAAAC TGTATAGCCT CCATTCGGAT GTATGTCTTT GGCAGGATGA TAAAGAATCA    120

GGAAGAAGGA GTATCCACGT TAGCCAAGTG TCCAGGCTGT GTCTGCTCTT ATTTTAGTGA    180

CAGATGTTGC TCCTGACAGA AGCTATTCTT CAGGAAACAT CACATCCAAT ATGGTAAATC    240

CATCAAACAG GAGCTAAGAA ACAGGAATGA GATGGGCACT TGCCCAAGGA AAAATGCCAG    300
```

-continued

```
GAGAGCAAAT AATGATGAAA AATAAACTTT TCCCTTTGTT TTTAATTTCA GGAAAAAATG    360
ATGAGGACCA AAATCAATGA ATAAGGAAAA CAGCTCAGAA AAAAGATGTT TCCAAATTGG    420
TAATTAAGTA TTTGTTCCTT GGGAAGAGAC CTCCATGTGA GCTTGATGGG AAAATGGGAA    480
AAACGTCAAA AGCATGATCT GATCAGATCC CAAAGTGGAT TATTATTTTA AAAACCAGAT    540
GGCATCACTC TGGGGAGGCA AGTTCAGGAA GGTCATGTTA GCAAAGGACA TAACAATAAC    600
AGCAAAATCA AAATTCCGCA AATGCAGGAG GAAAATGGGG ACTGGGAAAG CTTTCATAAC    660
AGTGATTAGG CAGTTGACCA TGTTCGCAAC ACCTCCCCGT CTATACCAGG GAACACAAAA    720
ATTGACTGGG CTAAGCCTGG ACTTTCAAGG GAAATATGAA AAACTGAGAG CAAAACAAAA    780
GACATGGTTA AAAGGCAACC AGAACATTGT GAGCCTTCAA AGCAGCAGTG CCCCTCAGCA    840
GGGACCCTGA GGCATTTGCC TTTAGGAAGG CCAGTTTTCT TAAGGAATCT TAAGAAACTC    900
TTGAAAGATC ATGAATTTTA ACCATTTTAA GTATAAAACA AATATGCGAT GCATAATCAG    960
TTTAGACATG GGTCCCAATT TTATAAAGTC AGGCATACAA GGATAACGTG TCCCAGCTCC   1020
GGATAGGTCA GAAATCATTA GAAATCACTG TGTCCCCATC CTAACTTTTT CAGAATGATC   1080
TGTCATAGCC CTCACACACA GGCCCGATGT GTCTGACCTA CAACCACATC TACAACCCAA   1140
GTGCCTCAAC CATTGTTAAC GTGTCATCTC AGTAGGTCCC ATTACAAATG CCACCTCCCC   1200
TGTGCAGCCC ATCCCGCTCC ACAGGAAGTC TCCCCACTCT AGACTTCTGC ATCACGATGT   1260
TACAGCCAGA AGCTCCGTGA GGGTGAGGGT CTGTGTCTTA CACCTACCTG TATGCTCTAC   1320
ACCTGAGCTC ACTGCAACCT CTGCCTCCCA GGTTCAAGCA ATTCTCCTGT CTCAGCCTCC   1380
CGCGTAGCTG GGACTACAGG CGCACGCCCG GCTAATTTTT GTATTGTTAG TAGAGATGGG   1440
GTTTCACCAT ATTAGCCCGG CTGGTCTTGA ACTCCTGACC TCAGGTGATC CACCCACCTC   1500
AGCCTCCTAA AGTGCTGGGA TTACAGGCAT GAGTCACCGC GCCCGGCCAA GGGTCAGTGT   1560
TTAATAAGGA ATAACTTGAA TGGTTTACTA AACCAACAGG GAAACAGACA AAAGCTGTGA   1620
TAATTTCAGG GATTCTTGGG ATGGGGAATG GTGCCATGAG CTGCCTGCCT AGTCCCAGAC   1680
CACTGGTCCT CATCACTTTC TTCCCTCATC CTCATTTTCA GGCTAAGTTA CCATTTTATT   1740
CACCATGCTT TTGTGGTAAG CCTCCACATC GTTACTGAAA TAAGAGTATA CATAAACTAG   1800
TTCCATTTGG GGCCATCTGT GTGTGTGTAT AGGGGAGGAG GGCATACCCC AGAGACTCCT   1860
TGAAGCCCCC GGCAGAGGTT TCCTCTCCAG CTGGGGGAGC CCTGCAAGCA CCCGGGGTCC   1920
TGGGTGTCCT GAGCAACCTG CCAGCCCGTG CCACTGGTTG TTTTGTTATC ACTCTCTAGG   1980
GACCTGTTGC TTTCTATTTC TGTGTGACTC GTTCATTCAT CCAGGCATTC ATTGACAATT   2040
TATTGAGTAC TTATATCTGC CAGACACCAG AGACAAAATG GTGAGCAAAG CAGTCACTGC   2100
CCTACCTTCG TGGAGGTGAC AGTTTCTCAT GGAAGACGTG CAGAAGAAAA TTAATAGCCA   2160
GCCAACTTAA ACCCAGTGCT GAAAGAAAGG AAATAAACAC CATCTTGAAG AATTGTGCGC   2220
AGCATCCCTT AACAAGGCCA CCTCCCTAGC GCCCCCTGCT GCCTCCATCG TGCCCGGAGG   2280
CCCCCAAGCC CGAGTCTTCC AAGCCTCCTC CTCCATCAGT CACAGCGCTG CAGCTGGCCT   2340
GCCTCGCTTC CCGTGAATCG TCCTGGTGCA TCTGAGCTGG AGACTCCTTG GCTCCAGGCT   2400
CCAGAAAGGA AATGGAGAGG GAAACTAGTC TAACGGAGAA TCTGGAGGGG ACAGTGTTTC   2460
CTCAGAGGGA AAGGGGCCTC CACGTCCAGG AGAATTCCAG GAGGTGGGGA CTGCAGGGAG   2520
TGGGGACGCT GGGGCTGAGC GGGTGCTGAA AGGCAGGAAG GTGAAAAGGG CAAGGCTGAA   2580
GCTGCCCAGA TGTTCAGTGT TGTTCACGGG GCTGGGAGTT TTCCGTTGCT TCCTGTGAGC   2640
CTTTTTATCT TTTCTCTGCT TGGAGGAGAA GAAGTCTATT TCATGAAGGG ATGCAGTTTC   2700
```

-continued

```
ATAAAGTCAG CTGTTAAAAT TCCAGGGTGT GCATGGGTTT TCCTTCACGA AGGCCTTTAT   2760
TTAATGGGAA TATAGGAAGC GAGCTCATTT CCTAGGCCGT TAATTCACGG AAGAAGTGAC   2820
TGGAGTCTTT TCTTTCATGT CTTCTGGGCA ACTACTCAGC CCTGTGGTGG ACTTGGCTTA   2880
TGCAAGACGG TCGAAAACCT TGGAATCAGG AGACTCGGTT TTCTTTCTGG TTCTGCCATT   2940
GGTTGGCTGT GCGACCGTGG GCAAGTGTCT CTCCTTCCCT GGGCCATAGT CTTCTCTGCT   3000
ATAAAGACCC TTGCAGCTCT CGTGTTCTGT GAACACTTCC CTGTGATTCT CTGTGAGGGG   3060
GGATGTTGAG AGGGGAAGGA GGCAGAGCTG GAGCAGCTGA GCCACAGGGG AGGTGGAGGG   3120
GGACAGGAAG GCAGGCAGAA GCTGGGTGCT CCATCAGTCC TCACTGATCA CGTCAGACTC   3180
CAGGACCGAG AGCCACAATG CTTCAGGAAA GCTCAATGAA CCCAACAGCC ACATTTTCCT   3240
TCCCTAAGCA TAGACAATGG CATTTGCCAA TAACCAAAAA GAATGCAGAG ACTAACTGGT   3300
GGTAGCTTTT GCCTGGCATT CAAAAACTGG GCCAGAGCAA GTGGAAAATG CCAGAGATTG   3360
TTAAACTTTT CACCCTGACC AGCACCCCAC GCAGCTCAGC AGTGACTGCT GACAGCACGG   3420
AGTGACCTGC AGCGCAGGGG AGGAGAAGAA AAAGAGAGGG ATAGTGTATG AGCAAGAAAG   3480
ACAGATTCAT TCAAGGGCAG TGGGAATTGA CCACAGGGAT TATAGTCCAC GTGATCCTGG   3540
GTTCTAGGAG GCAGGGCTAT ATTGTGGGGG GAAAAAATCA GTTCAAGGGA AGTCGGGAGA   3600
CCTGATTTCT AATACTATAT TTTTCCTTTA CAAGCTGAGT AATTCTGAGC AAGTCACAAG   3660
GTAGTAACTG AGGCTGTAAG ATTACTTAGT TTCTCCTTAT TAGGAACTCT TTTTCTCTGT   3720
GGAGTTAGCA GCACAAGGGC AATCCCGTTT CTTTTAACAG GAAGAAAACA TTCCTAAGAG   3780
TAAAGCCAAA CAGATTCAAG CCTAGGTCTT GCTGACTATA TGATTGGTTT TTTGAAAAAT   3840
CATTTCAGCG ATGTTTACTA TCTGATTCAG AAAATGAGAC TAGTACCCTT TGGTCAGCTG   3900
TAAACAAACA CCCATTTGTA AATGTCTCAA GTTCAGGCTT AACTGCAGAA CCAATCAAAT   3960
AAGAATAGAA TCTTTAGAGC AAACTGTGTT TCTCCACTCT GGAGGTGAGT CTGCCAGGGC   4020
AGTTTGGAAA TATTTACTTC ACAAGTATTG ACACTGTTGT TGGTATTAAC AACATAAAGT   4080
TGCTCAAAGG CAATCATTAT TTCAAGTGGC TTAAAGTTAC TTCTGACAGT TTTGGTATAT   4140
TTATTGGCTA TTGCCATTTG CTTTTTGTTT TTTCTCTTTG GGTTTATTAA TGTAAAGCAG   4200
GGATTATTAA CCTACAGTCC AGAAAGCCTG TGAATTTGAA TGAGGAAAAA ATTACGTTTT   4260
TATTTTTACC ACCTTCTAAC TAAATTTAAC ATTTTATTCC ATTGCGAATA GAGCCATAAA   4320
CTCAAAGTGG TAATAAGAGT ACCTGTGATT TTGTCATTAC CAATAGAAAT CACAGACATT   4380
TTATACTATA TTACAGTTGT TGCAGGTACG TTGTAAGTGA AATATTTATA CTCAAAACTA   4440
CTTTGAAATT AGACCTCCTG CTGGATCTTG TTTTTAACAT ATTAATAAAA CATGTTTAAA   4500
ATTTTGATAT TTTGATAATC ATATTTCATT ATCATTTGTT TCCTTTGTAA TCTATATTTT   4560
ATATATTTGA AAACATCTTT CTGAGAAGAG TTCCCCAGAT TTCACCAATG AGGTTCTTGG   4620
CATGCACACA CACAGAGTAA GAACTGATTT AGAGGCTAAC ATTGACATTG GTGCCTGAGA   4680
TGCAAGACTG AAATTAGAAA GTTCTCCCAA AGATACACAG TTGTTTTAAA GCTAGGGGTG   4740
AGGGGGGAAA TCTGCCGCTT CTATAGGAAT GCTCTCCCTG GAGCCTGGTA GGGTGCTGTC   4800
CTTGTGTTCT GGCTGGCTGT TATTTTTCTC TGTCCCTGCT ACGTCTTAAA GGACTTGTTT   4860
GGATCTCCAG TTCCTAGCAT AGTGCCTGGC ACAGTGCAGG TTCTCAATGA GTTTGCAGAG   4920
TGAATGGAAA TATAAACTAG AAATATATCT TTGTTGAAAT CAGCACACCA GTAGTCCTGG   4980
TGTAAGTGTG TGTACGTGTG TGTGTGTGTG TGTGTGTGTG TGTGTGTAAA ACCAGGTGGA   5040
```

-continued

```
GATATAGGAA CTATTATTGG GGTATGGGTG CATAAATTGG GATGTTCTTT TTAAAAAGAA   5100

ACTCCAAACA GACTTCTGGA AGGTTATTTT CTAAGAATCT TGCTGGCAGC GTGAAGGCAA   5160

CCCCCCTGTG CACAGCCCCA CCCAGCCTCA CGTGGCCACC TCTGTCTTCC CCCATGAAGG   5220

GCTGGCTCCC CAGTATATAT AAACCTCTCT GGAGCTCGGG CATGAGCCAG CAAGGCCACC   5280

CATCCAGGCA CCTCTCAGCA CAGC                                          5304
```

(2) INFORMATION FOR SEQ ID NO:3:

(i) SEQUENCE CHARACTERISTICS:
(A) LENGTH: 6169 base pairs
(B) TYPE: nucleic acid
(C) STRANDEDNESS: single
(D) TOPOLOGY: linear (xi) SEQUENCE DESCRIPTION: SEQ ID NO:3:

```
ATCTTTGTTC AGTTTACCTC AGGGCTATTA TGAAATGAAA TGAGATAACC AATGTGAAAG     60

TCCTATAAAC TGTATAGCCT CCATTCGGAT GTATGTCTTT GGCAGGATGA TAAAGAATCA    120

GGAAGAAGGA GTATCCACGT TAGCCAAGTG TCCAGGCTGT GTCTGCTCTT ATTTTAGTGA    180

CAGATGTTGC TCCTGACAGA AGCTATTCTT CAGGAAACAT CACATCCAAT ATGGTAAATC    240

CATCAAACAG GAGCTAAGAA ACAGGAATGA GATGGGCACT TGCCCAAGGA AAAATGCCAG    300

GAGAGCAAAT AATGATGAAA AATAAACTTT TCCCTTTGTT TTTAATTTCA GGAAAAAATG    360

ATGAGGACCA AAATCAATGA ATAAGGAAAA CAGCTCAGAA AAAAGATGTT TCCAAATTGG    420

TAATTAAGTA TTTGTTCCTT GGGAAGAGAC CTCCATGTGA GCTTGATGGG AAAATGGGAA    480

AAACGTCAAA AGCATGATCT GATCAGATCC CAAAGTGGAT TATTATTTTA AAAACCAGAT    540

GGCATCACTC TGGGGAGGCA AGTTCAGGAA GGTCATGTTA GCAAAGGACA TAACAATAAC    600

AGCAAAATCA AAATTCCGCA AATGCAGGAG GAAAATGGGG ACTGGGAAAG CTTTCATAAC    660

AGTGATTAGG CAGTTGACCA TGTTCGCAAC ACCTCCCCGT CTATACCAGG GAACACAAAA    720

ATTGACTGGG CTAAGCCTGG ACTTTCAAGG GAAATATGAA AAACTGAGAG CAAAACAAAA    780

GACATGGTTA AAAGGCAACC AGAACATTGT GAGCCTTCAA AGCAGCAGTG CCCCTCAGCA    840

GGGACCCTGA GGCATTTGCC TTTAGGAAGG CCAGTTTTCT TAAGGAATCT TAAGAAACTC    900

TTGAAAGATC ATGAATTTTA ACCATTTTAA GTATAAAACA AATATGCGAT GCATAATCAG    960

TTTAGACATG GGTCCCAATT TTATAAAGTC AGGCATACAA GGATAACGTG TCCCAGCTCC   1020

GGATAGGTCA GAAATCATTA GAAATCACTG TGTCCCCATC CTAACTTTTT CAGAATGATC   1080

TGTCATAGCC CTCACACACA GGCCCGATGT GTCTGACCTA CAACCACATC TACAACCCAA   1140

GTGCCTCAAC CATTGTTAAC GTGTCATCTC AGTAGGTCCC ATTACAAATG CCACCTCCCC   1200

TGTGCAGCCC ATCCCGCTCC ACAGGAAGTC TCCCCACTCT AGACTTCTGC ATCACGATGT   1260

TACAGCCAGA AGCTCCGTGA GGGTGAGGGT CTGTGTCTTA CACCTACCTG TATGCTCTAC   1320

ACCTGAGCTC ACTGCAACCT CTGCCTCCCA GGTTCAAGCA ATTCTCCTGT CTCAGCCTCC   1380

CGCGTAGCTG GGACTACAGG CGCACGCCCG GCTAATTTTT GTATTGTTAG TAGAGATGGG   1440

GTTTCACCAT ATTAGCCCGG CTGGTCTTGA ACTCCTGACC TCAGGTGATC CACCCACCTC   1500

AGCCTCCTAA AGTGCTGGGA TTACAGGCAT GAGTCACCGC GCCCGGCCAA GGGTCAGTGT   1560

TTAATAAGGA ATAACTTGAA TGGTTTACTA AACCAACAGG GAAACAGACA AAAGCTGTGA   1620

TAATTTCAGG GATTCTTGGG ATGGGGAATG GTGCCATGAG CTGCCTGCCT AGTCCCAGAC   1680

CACTGGTCCT CATCACTTTC TTCCCTCATC CTCATTTTCA GGCTAAGTTA CCATTTTATT   1740
```

-continued

```
CACCATGCTT TTGTGGTAAG CCTCCACATC GTTACTGAAA TAAGAGTATA CATAAACTAG   1800
TTCCATTTGG GGCCATCTGT GTGTGTGTAT AGGGGAGGAG GGCATACCCC AGAGACTCCT   1860
TGAAGCCCCC GGCAGAGGTT TCCTCTCCAG CTGGGGGAGC CCTGCAAGCA CCCGGGGTCC   1920
TGGGTGTCCT GAGCAACCTG CCAGCCCGTG CCACTGGTTG TTTTGTTATC ACTCTCTAGG   1980
GACCTGTTGC TTTCTATTTC TGTGTGACTC GTTCATTCAT CCAGGCATTC ATTGACAATT   2040
TATTGAGTAC TTATATCTGC CAGACACCAG AGACAAAATG GTGAGCAAAG CAGTCACTGC   2100
CCTACCTTCG TGGAGGTGAC AGTTTCTCAT GGAAGACGTG CAGAAGAAAA TTAATAGCCA   2160
GCCAACTTAA ACCCAGTGCT GAAAGAAAGG AAATAAACAC CATCTTGAAG AATTGTGCGC   2220
AGCATCCCTT AACAAGGCCA CCTCCCTAGC GCCCCCTGCT GCCTCCATCG TGCCCGGAGG   2280
CCCCCAAGCC CGAGTCTTCC AAGCCTCCTC CTCCATCAGT CACAGCGCTG CAGCTGGCCT   2340
GCCTCGCTTC CCGTGAATCG TCCTGGTGCA TCTGAGCTGG AGACTCCTTG GCTCCAGGCT   2400
CCAGAAAGGA AATGGAGAGG GAAACTAGTC TAACGGAGAA TCTGGAGGGG ACAGTGTTTC   2460
CTCAGAGGGA AAGGGGCCTC CACGTCCAGG AGAATTCCAG GAGGTGGGGA CTGCAGGGAG   2520
TGGGGACGCT GGGGCTGAGC GGGTGCTGAA AGGCAGGAAG GTGAAAAGGG CAAGGCTGAA   2580
GCTGCCCAGA TGTTCAGTGT TGTTCACGGG GCTGGGAGTT TTCCGTTGCT TCCTGTGAGC   2640
CTTTTTATCT TTTCTCTGCT TGGAGGAGAA GAAGTCTATT TCATGAAGGG ATGCAGTTTC   2700
ATAAAGTCAG CTGTTAAAAT TCCAGGGTGT GCATGGGTTT TCCTTCACGA AGGCCTTTAT   2760
TTAATGGGAA TATAGGAAGC GAGCTCATTT CCTAGGCCGT TAATTCACGG AAGAAGTGAC   2820
TGGAGTCTTT TCTTTCATGT CTTCTGGGCA ACTACTCAGC CCTGTGGTGG ACTTGGCTTA   2880
TGCAAGACGG TCGAAAACCT TGGAATCAGG AGACTCGGTT TTCTTTCTGG TTCTGCCATT   2940
GGTTGGCTGT GCGACCGTGG GCAAGTGTCT CTCCTTCCCT GGGCCATAGT CTTCTCTGCT   3000
ATAAAGACCC TTGCAGCTCT CGTGTTCTGT GAACACTTCC CTGTGATTCT CTGTGAGGGG   3060
GGATGTTGAG AGGGGAAGGA GGCAGAGCTG GAGCAGCTGA GCCACAGGGG AGGTGGAGGG   3120
GGACAGGAAG GCAGGCAGAA GCTGGGTGCT CCATCAGTCC TCACTGATCA CGTCAGACTC   3180
CAGGACCGAG AGCCACAATG CTTCAGGAAA GCTCAATGAA CCCAACAGCC ACATTTTCCT   3240
TCCCTAAGCA TAGACAATGG CATTTGCCAA TAACCAAAAA GAATGCAGAG ACTAACTGGT   3300
GGTAGCTTTT GCCTGGCATT CAAAAACTGG GCCAGAGCAA GTGGAAAATG CCAGAGATTG   3360
TTAAACTTTT CACCCTGACC AGCACCCCAC GCAGCTCAGC AGTGACTGCT GACAGCACGG   3420
AGTGACCTGC AGCGCAGGGG AGGAGAAGAA AAAGAGAGGG ATAGTGTATG AGCAAGAAAG   3480
ACAGATTCAT TCAAGGGCAG TGGGAATTGA CCACAGGGAT TATAGTCCAC GTGATCCTGG   3540
GTTCTAGGAG GCAGGGCTAT ATTGTGGGGG GAAAAAATCA GTTCAAGGGA AGTCGGGAGA   3600
CCTGATTTCT AATACTATAT TTTTCCTTTA CAAGCTGAGT AATTCTGAGC AAGTCACAAG   3660
GTAGTAACTG AGGCTGTAAG ATTACTTAGT TTCTCCTTAT TAGGAACTCT TTTTCTCTGT   3720
GGAGTTAGCA GCACAAGGGC AATCCCGTTT CTTTTAACAG GAAGAAAACA TTCCTAAGAG   3780
TAAAGCCAAA CAGATTCAAG CCTAGGTCTT GCTGACTATA TGATTGGTTT TTTGAAAAAT   3840
CATTTCAGCG ATGTTTACTA TCTGATTCAG AAAATGAGAC TAGTACCCTT TGGTCAGCTG   3900
TAAACAAACA CCCAGTTGTA AATGTCTCAA GTTCAGGCTT AACTGCAGAA CCAATCAAAA   3960
AGAATAGAAT CTTTAGAGCA AACTGTGTTT CTCCACATCT GGAGGTGAGT CTGCCAGGGC   4020
AGTTTGGAAA TATTTACTTC ACAAGTATTG ACACTGTTGT TGGTATTAAC AACATAAAGT   4080
TGCTCAAAGG CAATCATTAT TTCAAGTGGC TTAAAGTTAC TTCTGACAGT TTTGGTATAT   4140
```

-continued

```
TTATTGGCTA TTGCCATTTG CTTTTTGTTT TTTCTCTTTG GGTTTATTAA TGTAAAGCAG   4200

GGATTATTAA CCTACAGTCC AGAAAGCCTG TGAATTTGAA TGAGGAAAAA ATTACATTTT   4260

TGTTTTTACC ACCTTCTAAC TAAATTTAAC ATTTTATTCC ATTGCGAATA GAGCCATAAA   4320

CTCAAAGTGG TAATAACAGT ACCTGTGATT TTGTCATTAC CAATAGAAAT CACAGACATT   4380

TTATACTATA TTACAGTTGT TGCAGATACG TTGTAAGTGA AATATTTATA CTCAAAACTA   4440

CTTTGAAATT AGACCTCCTG CTGGATCTTG TTTTTAACAT ATTAATAAAA CATGTTTAAA   4500

ATTTTGATAT TTTGATAATC ATATTTCATT ATCATTTGTT TCCTTTGTAA TCTATATTTT   4560

ATATATTTGA AAACATCTTT CTGAGAAGAG TTCCCCAGAT TTCACCAATG AGGTTCTTGG   4620

CATGCACACA CACAGAGTAA GAACTGATTT AGAGGCTAAC ATTGACATTG GTGCCTGAGA   4680

TGCAAGACTG AAATTAGAAA GTTCTCCCAA AGATACACAG TTGTTTTAAA GCTAGGGGTG   4740

AGGGGGGAAA TCTGCCGCTT CTATAGGAAT GCTCTCCCTG GAGCCTGGTA GGGTGCTGTC   4800

CTTGTGTTCT GGCTGGCTGT TATTTTTCTC TGTCCCTGCT ACGTCTTAAA GGACTTGTTT   4860

GGATCTCCAG TTCCTAGCAT AGTGCCTGGC ACAGTGCAGG TTCTCAATGA GTTTGCAGAG   4920

TGAATGGAAA TATAAACTAG AAATATATCC TTGTTGAAAT CAGCACACCA GTAGTCCTGG   4980

TGTAAGTGTG TGTACGTGTG TGTGTGTGTG TGTGTGTGTG TGTAAAACCA GGTGGAGATA   5040

TAGGAACTAT TATTGGGGTA TGGGTGCATA AATTGGGATG TTCTTTTTAA AAAGAAACTC   5100

CAAACAGACT TCTGGAAGGT TATTTTCTAA GAATCTTGCT GGCAGCGTGA AGGCAACCCC   5160

CCTGTGCACA GCCCCACCCA GCCTCACGTG GCCACCTCTG TCTTCCCCCA TGAAGGGCTG   5220

GCTCCCCAGT ATATATAAAC CTCTCTGGAG CTCGGGCATG AGCCAGCAAG GCCACCCATC   5280

CAGGCACCTC TCAGCACAGC AGAGCTTTCC AGAGGAAGCC TCACCAAGCC TCTGCAATGA   5340

GGTTCTTCTG TGCACGTTGC TGCAGCTTTG GGCCTGAGAT GCCAGCTGTC CAGCTGCTGC   5400

TTCTGGCCTG CCTGGTGTGG GATGTGGGGG CCAGGACAGC TCAGCTCAGG AAGGCCAATG   5460

ACCAGAGTGG CCGATGCCAG TATACCTTCA GTGTGGCCAG TCCCAATGAA TCCAGCTGCC   5520

CAGAGCAGAG CCAGGCCATG TCAGTCATCC ATAACTTACA GAGAGACAGC AGCACCCAAC   5580

GCTTAGACCT GGAGGCCACC AAAGCTCGAC TCAGCTCCCT GGAGAGCCTC CTCCACCAAT   5640

TGACCTTGGA CCAGGCTGCC AGGCCCCAGG AGACCCAGGA GGGGCTGCAG AGGGAGCTGG   5700

GCACCCTGAG GCGGGAGCGG GACCAGCTGG AAACCCAAAC CAGAGAGTTG GAGACTGCCT   5760

ACAGCAACCT CCTCCGAGAC AAGTCAGTTC TGGAGGAAGA GAAGAAGCGA CTAAGGCAAG   5820

AAAATGAGAA TCTGGCCAGG AGGTTGGAAA GCAGCAGCCA GGAGGTAGCA AGGCTGAGAA   5880

GGGGCCAGTG TCCCCAGACC CGAGACACTG CTCGGGCTGT GCCACCAGGC TCCAGAGAAG   5940

GTAAGAATGC AGAGTGGGGG GACTCTGAGT TCAGCAGGTG ATATGGCTCG TAGTGACCTG   6000

CTACAGGCGC TCCAGGCCTC CCTGCCCTTT CTCCTAGAGA CTGCACAGCT AGCACAAGAC   6060

AGATGAATTA AGGAAAGCAC ACGATCACCT TCAAGTATTA CTAGTAATTT AGCTCCTGAG   6120

AGCTTCATTT AGATTAGTGG TTCAGAGTTC TTGTGCCCCT CCATGTCAG              6169
```

(2) INFORMATION FOR SEQ ID NO:4:

(i) SEQUENCE CHARACTERISTICS:
(A) LENGTH: 926 base pairs
(B) TYPE: nucleic acid
(C) STRANDEDNESS: single
(D) TOPOLOGY: linear (xi) SEQUENCE DESCRIPTION: SEQ ID NO:4:

-continued

```
AAGGTAGGCA CATTGCCCTG CAATTTATAA TTTATGAGGT GTTCAATTAT GGAATTGTCA     60

AATATTAACA AAAGTAGAGA GACTACAATG AACTCCAATG TAGCCATAAC TCAGGCCCAA    120

CTGTTATCAG CACAGTCCAA TCATGTTTTA TCTTTCCTTC TCTGACCCCC AACCCATCCC    180

CAGTCCTTAT CTAAAATCAA ATATCAAACA CCATACTCTT TGGGAGCCTA TTTATTTAGT    240

TAGTTAGTTT TCAGACAGAG TTTCTTTCTT GTTCCCAAGC TGGAGTACAA TAGTGTAGTC    300

TCGGCTAACA GCAATCTCCC CCTCCTTGGT TCAAGCAATT CTCCTGCCTC AGTCTCCCAA    360

GAAGCTGGGA TTATAGACAC CTGCCACCAC ATCCAGCTAA TTTTTTTGTG TTTTAGAAAA    420

GACAGGGTTT CACCATGTTG GCCAGGCTGG TTTCGAACTC CTGACCTCAG GTGATCCGCC    480

TGCCTCGGCC TCCCAAAGTG CTGGGATTAC AGGCATGAGC CACCACGCCT GGCCGGCAGC    540

CTATTTAAAT GTCATCCTCA ACATAGTCAA TCCTTGGGCC ATTTTTTCTT ACAGTAAAAT    600

TTTGTCTCTT TCTTTTAATC AGTTTCTACG TGGAATTTGG ACACTTTGGC CTTCCAGGAA    660

CTGAAGTCCG AGCTAACTGA AGTTCCTGCT TCCCGAATTT TGAAGGAGAG CCCATCTGGC    720

TATCTCAGGA GTGGAGAGGG AGACACCGGT ATGAAGTTAA GTTTCTTCCC TTTTGTGCCC    780

ACGTGGTCTT TATTCATGTC TAGTGCTGTG TTCAGAGAAT CAGTATAGGG TAAATGCCCA    840

CCCAAGGGGG AAATTAACTT CCCTGGGAGC AGAGGGAGGG GAGGAGAAGA GGAACAGAAC    900

TCTCTCTCTC TCTCTGTTAC CCTTGT                                         926
```

(2) INFORMATION FOR SEQ ID NO:5:

(i) SEQUENCE CHARACTERISTICS:
 (A) LENGTH: 2099 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:5:

```
TGGCTCTGCC AAGCTTCCGC ATGATCATTG TCTGTGTTTG GAAGATTATG GATTAAGTGG     60

TGCTTCGTTT TCTTTCTGAA TTTACCAGGA TGTGGAGAAC TAGTTTGGGT AGGAGAGCCT    120

CTCACGCTGA GAACAGCAGA AACAATTACT GGCAAGTATG GTGTGTGGAT GCGAGACCCC    180

AAGCCCACCT ACCCCTACAC CCAGGAGACC ACGTGGAGAA TCGACACAGT TGGCACGGAT    240

GTCCGCCAGG TTTTTGAGTA TGACCTCATC AGCCAGTTTA TGCAGGGCTA CCCTTCTAAG    300

GTTCACATAC TGCCTAGGCC ACTGGAAAGC ACGGGTGCTG TGGTGTACTC GGGGAGCCTC    360

TATTTCCAGG GCGCTGAGTC CAGAACTGTC ATAAGATATG AGCTGAATAC CGAGACAGTG    420

AAGGCTGAGA AGGAAATCCC TGGAGCTGGC TACCACGGAC AGTTCCCGTA TTCTTGGGGT    480

GGCTACACGG ACATTGACTT GGCTGTGGAT GAAGCAGGCC TCTGGGTCAT TTACAGCACC    540

GATGAGGCCA AAGGTGCCAT TGTCCTCTCC AAACTGAACC CAGAGAATCT GGAACTCGAA    600

CAAACCTGGG AGACAAACAT CCGTAAGCAG TCAGTCGCCA ATGCCTTCAT CATCTGTGGC    660

ACCTTGTACA CCGTCAGCAG CTACACCTCA GCAGATGCTA CCGTCAACTT TGCTTATGAC    720

ACAGGCACAG GTATCAGCAA GACCCTGACC ATCCCATTCA AGAACCGCTA TAAGTACAGC    780

AGCATGATTG ACTACAACCC CCTGGAGAAG AAGCTCTTTG CCTGGGACAA CTTGAACATG    840

GTCACTTATG ACATCAAGCT CTCCAAGATG TGAAAAGCCT CCAAGCTGTA CAGGCAATGG    900

CAGAAGGAGA TGCTCAGGGC TCCTGGGGGG AGCAGGCTGA AGGGAGAGCC AGCCAGCCAG    960

GGCCCAGGCA GCTTTGACTG CTTTCCAAGT TTTCATTAAT CCAGAAGGAT GAACATGGTC   1020
```

-continued

```
ACCATCTAAC TATTCAGGAA TTGTAGTCTG AGGGCGTAGA CAATTTCATA TAATAAATAT   1080

CCTTTATCTT CTGTCAGCAT TTATGGGATG TTTAATGACA TAGTTCAAGT TTTCTTGTGA   1140

TTTGGGGCAA AAGCTGTAAG GCATAATAGT TTCTTCCTGA AAACCATTGC TCTTGCATGT   1200

TACATGGTTA CCACAAGCCA CAATAAAAAG CATAACTTCT AAAGGAAGCA GAATAGCTCC   1260

TCTGGCCAGC ATCGAATATA AGTAAGATGC ATTTACTACA GTTGGCTTCT AATGCTTCAG   1320

ATAGAATACA GTTGGGTCTC ACATAACCCT TACATTGTGA AATAAAATTT TCTTACCCAA   1380

CGTTCTCTTC CTTGAACTTT GTGGGAATCT TTGCTTAAGA GAAGGATATA GATTCCAACC   1440

ATCAGGTAAT TCCTTCAGGT TGGGAGATGT GATTGCAGGA TGTTAAAGGT GTGTGTGTGT   1500

GTGTGTGTGT GTGTGTAACT GAGAGGCTTG TGCCTGGTTT TGAGGTGCTG CCCAGGATGA   1560

CGCCAAGCAA ATAGCGCATC CACACTTTCC CACCTCCATC TCCTGGTGCT CTCGGCACTA   1620

CCGGAGCAAT CTTTCCATCT CTCCCCTGAA CCCACCCTCT ATTCACCCTA ACTCCACTTC   1680

AGTTTGCTTT TGATTTTTTT TTTTTTTTTT TTTTTTTTTT GAGATGGGGT CTCGCTCTGT   1740

CACCCAGGCT GGAGTGCAGT GGCACGATCT CGGCTCACTG CAAGTTCCGC CTCCCAGGTT   1800

CACACCATTC TCCTGCCTCA GCCTCCCAAG TAGCTGGGAC TACAGGCACC TGCCACCACG   1860

CCTGGCTAAT TTTTTTTTTT TCCAGTGAAG ATGGGTTTCA CCATGTTAGC CAGGATGGTC   1920

TCGATCTCCT GACCTTGTCA TCCACCCACC TTGGCCTCCC AAAGTGCTGG GATTACAGGC   1980

GTGAGCCACC ACGCCCAGCC CCTCCACTTC AGTTTTTATC TGTCATCAGG GGTATGAATT   2040

TTATAAGCCA CACCTCAGGT GGAGAAAGCT TGATGCATAG CTTGAGTATT CTATACTGT    2099
```

(2) INFORMATION FOR SEQ ID NO:6:

(i) SEQUENCE CHARACTERISTICS:
- (A) LENGTH: 19 base pairs
- (B) TYPE: nucleic acid
- (C) STRANDEDNESS: single
- (D) TOPOLOGY: linear (xi) SEQUENCE DESCRIPTION: SEQ ID NO:6:

```
TGAGGCTTCC TCTGGAAAC                                                  19
```

(2) INFORMATION FOR SEQ ID NO:7:

(i) SEQUENCE CHARACTERISTICS:
- (A) LENGTH: 20 base pairs
- (B) TYPE: nucleic acid
- (C) STRANDEDNESS: single
- (D) TOPOLOGY: linear (xi) SEQUENCE DESCRIPTION: SEQ ID NO:7:

```
TGAAATCAGC ACACCAGTAG                                                 20
```

(2) INFORMATION FOR SEQ ID NO:8:

(i) SEQUENCE CHARACTERISTICS:
- (A) LENGTH: 21 base pairs
- (B) TYPE: nucleic acid
- (C) STRANDEDNESS: single
- (D) TOPOLOGY: linear (xi) SEQUENCE DESCRIPTION: SEQ ID NO:8:

```
GCACCCATAC CCCAATAATA G                                               21
```

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:9:

AGAGTTCCCC AGATTTCACC 20

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:10:

ATCTGGGGAA CTCTTCTCAG 20

(2) INFORMATION FOR SEQ ID NO:11:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:11:

TACAGTTGTT GCAGATACG 19

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:12:

ACAACGTATC TGCAACAACT G 21

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:13:

TCAGGCTTAA CTGCAGAACC 20

(2) INFORMATION FOR SEQ ID NO:14:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:14:

TTGGTTCTGC AGTTAAGCC 19

(2) INFORMATION FOR SEQ ID NO:15:

(i) SEQUENCE CHARACTERISTICS:

(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:15:

AGCAGCACAA GGGCAATCC 19

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:16:

ACAGGGCTAT ATTGTGGG 18

(2) INFORMATION FOR SEQ ID NO:17:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:17:

CCTGAGATGC CAGCTGTCC 19

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:18:

CTGAAGCATT AGAAGCCAAC 20

(2) INFORMATION FOR SEQ ID NO:19:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:19:

ACCTTGGACC AGGCTGCCAG 20

(2) INFORMATION FOR SEQ ID NO:20:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:20:

AGGTTTGTTC GAGTTCCAG 19

(2) INFORMATION FOR SEQ ID NO:21:

(i) SEQUENCE CHARACTERISTICS:
(A) LENGTH: 20 base pairs (B) TYPE: nucleic acid
(C) STRANDEDNESS: single
(D) TOPOLOGY: linear (xi) SEQUENCE DESCRIPTION: SEQ ID NO:21:

ACAATTACTG GCAAGTATGG 20

(2) INFORMATION FOR SEQ ID NO:22:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:22:

CCTTCTCAGC CTTGCTACC 19

(2) INFORMATION FOR SEQ ID NO:23:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:23:

ACACCTCAGC AGATGCTACC 20

(2) INFORMATION FOR SEQ ID NO:24:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:24:

ATGGATGACT GACATGGCC 19

(2) INFORMATION FOR SEQ ID NO:25:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:25:

AAGGATGAAC ATGGTCACC 19

(2) INFORMATION FOR SEQ ID NO:26:

(i) SEQUENCE CHARACTERISTICS:
(A) LENGTH: 1548 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:26:

AGAGCTTTCC AGAGGAAGCC TCACCAAGCC TCTGCAATGA GGTTCTTCTG TGCACGTTGC 60

TGCAGCTTTG GGCCTGAGAT GCCAGCTGTC CAGCTGCTGC TTCTGGCCTG CCTGGTGTGG 120

GATGTGGGGG CCAGGACAGC TCAGCTCAGG AAGGCCAATG ACCAGAGTGG CCGATGCCAG 180

-continued

```
TATACCTTCA GTGTGGCCAG TCCCAATGAA TCCAGCTGCC CAGAGCAGAG CCAGGCCATG    240

TCAGTCATCC ATAACTTACA GAGAGACAGC AGCACCCAAC GCTTAGACCT GGAGGCCACC    300

AAAGCTCGAC TCAGCTCCCT GGAGAGCCTC CTCCACCAAT TGACCTTGGA CCAGGCTGCC    360

AGGCCCCAGG AGACCCAGGA GGGGCTGCAG AGGGAGCTGG GCACCCTGAG GCGGGAGCGG    420

GACCAGCTGG AAACCCAAAC CAGAGAGTTG GAGACTGCCT ACAGCAACCT CCTCCGAGAC    480

AAGTCAGTTC TGGAGGAAGA GAAGAAGCGA CTAAGGCAAG AAAATGAGAA TCTGGCCAGG    540

AGGTTGGAAA GCAGCAGCCA GGAGGTAGCA AGGCTGAGAA GGGGCCAGTG TCCCCAGACC    600

CGAGACACTG CTCGGGCTGT GCCACCAGGC TCCAGAGAAG TTTCTACGTG GAATTTGGAC    660

ACTTTGGCCT TCCAGGAACT GAAGTCCGAG CTAACTGAAG TTCCTGCTTC CCGAATTTTG    720

AAGGAGAGCC CATCTGGCTA TCTCAGGAGT GGAGAGGGAG ACACCGGATG TGGAGAACTA    780

GTTTGGGTAG GAGAGCCTCT CACGCTGAGA ACAGCAGAAA CAATTACTGG CAAGTATGGT    840

GTGTGGATGC GAGACCCCAA GCCCACCTAC CCCTACACCC AGGAGACCAC GTGGAGAATC    900

GACACAGTTG GCACGGATGT CCGCCAGGTT TTTGAGTATG ACCTCATCAG CCAGTTTATG    960

CAGGGCTACC CTTCTAAGGT TCACATACTG CCTAGGCCAC TGGAAAGCAC GGGTGCTGTG   1020

GTGTACTCGG GGAGCCTCTA TTTCCAGGGC GCTGAGTCCA GAACTGTCAT AAGATATGAG   1080

CTGAATACCG AGACAGTGAA GGCTGAGAAG GAAATCCCTG GAGCTGGCTA CCACGGACAG   1140

TTCCCGTATT CTTGGGGTGG CTACACGGAC ATTGACTTGG CTGTGGATGA AGCAGGCCTC   1200

TGGGTCATTT ACAGCACCGA TGAGGCCAAA GGTGCCATTG TCCTCTCCAA ACTGAACCCA   1260

GAGAATCTGG AACTCGAACA AACCTGGGAG ACAAACATCC GTAAGCAGTC AGTCGCCAAT   1320

GCCTTCATCA TCTGTGGCAC CTTGTACACC GTCAGCAGCT ACACCTCAGC AGATGCTACC   1380

GTCAACTTTG CTTATGACAC AGGCACAGGT ATCAGCAAGA CCCTGACCAT CCCATTCAAG   1440

AACCGCTATA AGTACAGCAG CATGATTGAC TACAACCCCC TGGAGAAGAA GCTCTTTGCC   1500

TGGGACAACT TGAACATGGT CACTTATGAC ATCAAGCTCT CCAAGATG                1548
```

(2) INFORMATION FOR SEQ ID NO:27:

(i) SEQUENCE CHARACTERISTICS:
(A) LENGTH: 178 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:27:

```
Thr Gly Ala Val Val Tyr Ser Gly Ser Leu Tyr Phe Gln Gly Ala Glu
 1               5                  10                  15

Ser Arg Thr Val Ile Arg Tyr Glu Leu Asn Thr Glu Thr Val Lys Ala
            20                  25                  30

Glu Lys Glu Ile Pro Gly Ala Gly Tyr His Gly Gln Phe Pro Tyr Ser
        35                  40                  45

Trp Gly Gly Tyr Thr Asp Ile Asp Leu Ala Val Asp Glu Ala Gly Leu
    50                  55                  60

Trp Val Ile Tyr Ser Thr Asp Glu Ala Lys Gly Ala Ile Val Leu Ser
65                  70                  75                  80

Lys Leu Asn Pro Glu Asn Leu Glu Leu Glu Gln Thr Trp Glu Thr Asn
                85                  90                  95

Ile Arg Lys Gln Ser Val Ala Asn Ala Phe Ile Ile Cys Gly Thr Leu
            100                 105                 110
```

```
Tyr Thr Val Ser Ser Tyr Thr Ser Ala Asp Ala Thr Val Asn Phe Ala
        115                 120                 125

Tyr Asp Thr Gly Thr Gly Ile Ser Lys Thr Leu Thr Ile Pro Phe Lys
    130                 135                 140

Asn Arg Tyr Lys Tyr Ser Ser Met Ile Asp Tyr Asn Pro Leu Glu Lys
145                 150                 155                 160

Lys Leu Phe Ala Trp Asp Asn Leu Asn Met Val Thr Tyr Asp Ile Lys
                165                 170                 175

Leu Ser
```

(2) INFORMATION FOR SEQ ID NO:28:

(i) SEQUENCE CHARACTERISTICS:
(A) LENGTH: 131 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:28:

```
Arg Phe Asp Leu Lys Thr Glu Thr Ile Leu Lys Thr Arg Ser Leu Asp
 1               5                  10                  15

Tyr Ala Gly Tyr Asn Asn Met Tyr His Tyr Ala Trp Gly Gly His Ser
            20                  25                  30

Asp Ile Asp Leu Met Val Asp Glu Ser Gly Leu Trp Ala Val Tyr Ala
        35                  40                  45

Thr Asn Gln Asn Ala Gly Asn Ile Val Val Ser Arg Leu Asp Pro Val
    50                  55                  60

Ser Leu Gln Thr Leu Gln Thr Trp Asn Thr Ser Tyr Pro Lys Arg Xaa
65                  70                  75                  80

Pro Gly Xaa Ala Phe Ile Ile Cys Gly Thr Cys Tyr Val Thr Asn Gly
                85                  90                  95

Tyr Ser Gly Gly Thr Lys Val His Tyr Ala Tyr Gln Thr Asn Ala Ser
            100                 105                 110

Thr Tyr Glu Tyr Ile Asp Ile Pro Phe Gln Asn Lys Leu Xaa Pro His
        115                 120                 125

Phe Pro Cys
    130
```

(2) INFORMATION FOR SEQ ID NO:29:

(i) SEQUENCE CHARACTERISTICS:
(A) LENGTH: 178 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:29:

```
Gly Thr Gly Gln Val Val Tyr Asn Gly Ser Ile Tyr Phe Asn Lys Phe
 1               5                  10                  15

Gln Ser His Ile Ile Ile Arg Phe Asp Leu Lys Thr Glu Thr Ile Leu
            20                  25                  30

Lys Thr Arg Ser Leu Asp Tyr Ala Gly Tyr Asn Asn Met Tyr His Tyr
        35                  40                  45

Ala Trp Gly Gly His Ser Asp Ile Asp Leu Met Val Asp Glu Asn Gly
    50                  55                  60
```

-continued

```
Leu Trp Ala Val Tyr Ala Thr Asn Gln Asn Ala Gly Asn Ile Val Ile
65                  70                  75                  80

Ser Lys Leu Asp Pro Val Ser Leu Gln Ile Leu Gln Thr Trp Asn Thr
                85                  90                  95

Ser Tyr Pro Lys Arg Ser Ala Gly Glu Ala Phe Ile Ile Cys Gly Thr
            100                 105                 110

Leu Tyr Val Thr Asn Gly Tyr Ser Gly Gly Thr Lys Val His Tyr Ala
        115                 120                 125

Tyr Gln Thr Asn Ala Ser Thr Tyr Glu Tyr Ile Asp Ile Pro Phe Gln
    130                 135                 140

Asn Lys Tyr Ser His Ile Ser Met Leu Asp Tyr Asn Pro Lys Asp Arg
145                 150                 155                 160

Ala Leu Tyr Ala Trp Asn Asn Gly His Gln Thr Leu Tyr Asn Val Thr
                165                 170                 175

Leu Phe
```

(2) INFORMATION FOR SEQ ID NO:30:

(i) SEQUENCE CHARACTERISTICS:
(A) LENGTH: 177 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:30:

```
Gly Ala Gly Val Val Val His Asn Asn Asn Leu Tyr Tyr Asn Cys Phe
 1               5                  10                  15

Asn Ser His Asp Met Cys Arg Ala Ser Leu Thr Ser Gly Val Tyr Gln
            20                  25                  30

Lys Lys Pro Leu Leu Asn Ala Leu Phe Asn Asn Arg Phe Ser Tyr Ala
        35                  40                  45

Gly Thr Met Phe Gln Asp Met Asp Phe Ser Ser Asp Glu Lys Gly Leu
    50                  55                  60

Trp Val Ile Phe Thr Thr Glu Lys Ser Ala Gly Lys Ile Val Val Gly
65                  70                  75                  80

Lys Val Asn Val Ala Thr Phe Thr Val Asp Asn Ile Trp Ile Thr Thr
                85                  90                  95

Gln Asn Lys Ser Asp Ala Ser Asn Ala Phe Met Ile Cys Gly Val Leu
            100                 105                 110

Tyr Val Thr Arg Ser Leu Gly Pro Lys Met Glu Glu Val Phe Tyr Met
        115                 120                 125

Phe Asp Thr Lys Thr Gly Lys Glu Gly His Leu Ser Ile Met Met Glu
    130                 135                 140

Lys Met Ala Glu Lys Val His Ser Leu Ser Tyr Asn Ser Asn Asp Arg
145                 150                 155                 160

Lys Leu Tyr Met Phe Ser Glu Gly Tyr Leu Leu His Tyr Asp Ile Ala
                165                 170                 175

Leu
```

(2) INFORMATION FOR SEQ ID NO:31:

(i) SEQUENCE CHARACTERISTICS:
(A) LENGTH: 74 amino acids
(B) TYPE: amino acid
(C) STRANDEDNESS: single (D) TOPOLOGY: linear (ii) MOLECULE TYPE: None (xi) SEQUENCE DESCRIPTION: SEQ ID NO:31:

```
Gly Val Val Tyr Ser Arg Leu Thr Glu Thr Leu Ala Gly Tyr Asn Asn
 1               5                  10                  15

Tyr Ala Trp Gly Gly Asp Ile Asp Leu Val Asp Glu Gly Leu Trp Tyr
            20                  25                  30

Thr Ala Gly Ile Val Ser Lys Leu Pro Leu Gln Thr Trp Thr Lys Ala
        35                  40                  45

Phe Ile Ile Cys Gly Thr Leu Tyr Val Thr Tyr Val Tyr Ala Tyr Thr
    50                  55                  60

Ile Tyr Asp Tyr Asn Pro Lys Leu Tyr Leu
65                  70
```

(2) INFORMATION FOR SEQ ID NO:32:

(i) SEQUENCE CHARACTERISTICS:
(A) LENGTH: 504 amino acids
(B) TYPE: amino acid
(C) STRANDEDNESS: single
(D) TOPOLOGY: linear (ii) MOLECULE TYPE: protein (v) FRAGMENT TYPE: N-terminal (xi) SEQUENCE DESCRIPTION: SEQ ID NO:32:

```
Met Arg Phe Phe Cys Ala Arg Cys Cys Ser Phe Gly Pro Glu Met Pro
 1               5                  10                  15

Ala Val Gln Leu Leu Leu Leu Ala Cys Leu Val Trp Asp Val Gly Ala
            20                  25                  30

Arg Thr Ala Gln Leu Arg Lys Ala Asn Asp Gln Ser Gly Arg Cys Gln
        35                  40                  45

Tyr Thr Phe Ser Val Ala Ser Pro Asn Glu Ser Ser Cys Pro Glu Gln
    50                  55                  60

Ser Gln Ala Met Ser Val Ile His Asn Leu Gln Arg Asp Ser Ser Thr
65                  70                  75                  80

Gln Arg Leu Asp Leu Glu Ala Thr Lys Ala Arg Leu Ser Ser Leu Glu
                85                  90                  95

Ser Leu Leu His Gln Leu Thr Leu Asp Gln Ala Ala Arg Pro Gln Glu
            100                 105                 110

Thr Gln Glu Gly Leu Gln Arg Glu Leu Gly Thr Leu Arg Arg Glu Arg
        115                 120                 125

Asp Gln Leu Glu Thr Gln Thr Arg Glu Leu Glu Thr Ala Tyr Ser Asn
    130                 135                 140

Leu Leu Arg Asp Lys Ser Val Leu Glu Glu Glu Lys Lys Arg Leu Arg
145                 150                 155                 160

Gln Glu Asn Glu Asn Leu Ala Arg Arg Leu Glu Ser Ser Ser Gln Glu
                165                 170                 175

Val Ala Arg Leu Arg Arg Gly Gln Cys Pro Gln Thr Arg Asp Thr Ala
            180                 185                 190

Arg Ala Val Pro Pro Gly Ser Arg Glu Val Ser Thr Trp Asn Leu Asp
        195                 200                 205

Thr Leu Ala Phe Gln Glu Leu Lys Ser Glu Leu Thr Glu Val Pro Ala
    210                 215                 220

Ser Arg Ile Leu Lys Glu Ser Pro Ser Gly Tyr Leu Arg Ser Gly Glu
```

-continued

```
225                 230                 235                 240

Gly Asp Thr Gly Cys Gly Glu Leu Val Trp Val Gly Glu Pro Leu Thr
                245                 250                 255

Leu Arg Thr Ala Glu Thr Ile Thr Gly Lys Tyr Gly Val Trp Met Arg
            260                 265                 270

Asp Pro Lys Pro Thr Tyr Pro Tyr Thr Gln Glu Thr Thr Trp Arg Ile
        275                 280                 285

Asp Thr Val Gly Thr Asp Val Arg Gln Val Phe Glu Tyr Asp Leu Ile
    290                 295                 300

Ser Gln Phe Met Gln Gly Tyr Pro Ser Lys Val His Ile Leu Pro Arg
305                 310                 315                 320

Pro Leu Glu Ser Thr Gly Ala Val Val Tyr Ser Gly Ser Leu Tyr Phe
                325                 330                 335

Gln Gly Ala Glu Ser Arg Thr Val Ile Arg Tyr Glu Leu Asn Thr Glu
            340                 345                 350

Thr Val Lys Ala Glu Lys Glu Ile Pro Gly Ala Gly Tyr His Gly Gln
        355                 360                 365

Phe Pro Tyr Ser Trp Gly Gly Tyr Thr Asp Ile Asp Leu Ala Val Asp
    370                 375                 380

Glu Ala Gly Leu Trp Val Ile Tyr Ser Thr Asp Glu Ala Lys Gly Ala
385                 390                 395                 400

Ile Val Leu Ser Lys Leu Asn Pro Glu Asn Leu Glu Leu Glu Gln Thr
                405                 410                 415

Trp Glu Thr Asn Ile Arg Lys Gln Ser Val Ala Asn Ala Phe Ile Ile
            420                 425                 430

Cys Gly Thr Leu Tyr Thr Val Ser Ser Tyr Thr Ser Ala Asp Ala Thr
        435                 440                 445

Val Asn Phe Ala Tyr Asp Thr Gly Thr Gly Ile Ser Lys Thr Leu Thr
    450                 455                 460

Ile Pro Phe Lys Asn Arg Tyr Lys Tyr Ser Ser Met Ile Asp Tyr Asn
465                 470                 475                 480

Pro Leu Glu Lys Lys Leu Phe Ala Trp Asp Asn Leu Asn Met Val Thr
                485                 490                 495

Tyr Asp Ile Lys Leu Ser Lys Met
            500
```

METHODS FOR THE DIAGNOSIS, PROGNOSIS AND TREATMENT OF GLAUCOMA AND RELATED DISORDERS

This application is a continuation-in-part of U.S. patent application Ser. No. 08/791,154, filed Jan. 28, 1997, now abandoned, which is herein by reference.

FIELD OF THE INVENTION

The present invention is in the fields of diagnostics, prognosis, and treatment, and concerns methods and reagents for diagnosing and treating glaucoma and related disorders.

BACKGROUND OF THE INVENTION

"Glaucomas" are a group of debilitating eye diseases that are the leading cause of preventable blindness in the United States and other developed nations. Primary Open Angle Glaucoma ("POAG") is the most common form of glaucoma. The disease is characterized by the alteration of the trabecular meshwork, leading to obstruction of the normal ability of aqueous humor to leave the eye without closure of the space (e.g., the "angle") between the iris and cornea (see, Vaughan, D. et al., In: *General Ophthalmology,* Appleton & Lange, Norwalk, Conn., pp. 213–230 (1992)). A characteristic of such obstruction in this disease is an increased intraocular pressure ("IOP"), resulting in progressive visual loss and blindness if not treated appropriately and in a timely fashion.

The disease is estimated to affect between 0.4% and 3.3% of all adults over 40 years old (Leske, M. C. et al., *Amer. J. Epidemiol.* 113:1843–1846 (1986); Bengtsson, B., *Br. J. Ophthamol.* 73:483–487 (1989); Strong, N. P., *Ophthal. Physiol. Opt.* 12:3–7 (1992)). Moreover, the prevalence of the disease rises with age to over 6% of those 75 years or older (Strong, N. P., *Ophthal. Physiol. Opt.* 12:3–7 (1992)).

A link between the IOP response of patients to glucocorticoids and the disease of POAG has long been suspected. While only 5% of the normal population shows a high IOP increase (16 mm Hg) to topical glucocorticoid testing, greater than 40–50% of patients with POAG show this response. In addition, an Open Angle glaucoma may be induced by exposure to glucocorticoids. This observation has suggested that an increased or abnormal glucocorticoid response in trabecular cells may be involved in POAG (Zhan, G. L. et al., *Exper. Eye Res.* 54:211–218 (1992); Yun, A. J. et al., *Invest. Ophthamol. Vis. Sci.* 30:2012–2022 (1989); Clark, A. F., *Exper. Eye Res.* 55:265 (1992); Klemetti, A., *Acta Ophthamol.* 68:29–33 (1990); Knepper, P. A., U.S. Pat. No. 4,617,299).

The ability of glucocorticoids to induce a glaucoma-like condition has led to efforts to identify genes or gene products that would be induced by the cells of the trabecular meshwork in response to glucocorticoids (Polansky, J. R. et al., In: *Glaucoma Update IV,* Springer-Verlag, Berlin, pp. 20–29 (1991)). Initial efforts using short-term exposure to dexamethasone revealed only changes in specific protein synthesis. Extended exposure to relatively high levels of dexamethasone was, however, found to induce the expression of related 66 kD and 55 kD proteins that could be visualized by gel electrophoresis (Polansky, J. R. et al., In: *Glaucoma Update IV,* Springer-Verlag, Berlin, pp. 20–29 (1991)). The induction kinetics of these proteins as well as their dose response characteristics were similar to the kinetics that were required for steroid-induced IOP elevation in human subjects (Polansky, J. R. et al., In: *Glaucoma Update IV,* Springer-Verlag, Berlin, pp. 20–29 (1991)). Problems of aggregation and apparent instability or loss of protein in the purification process were obstacles in obtaining a direct protein sequence.

Because increased IOP is a readily measurable characteristic of glaucoma, the diagnosis of the disease is largely screened for by measuring intraocular pressure (tonometry) (Strong, N. P., *Ophthal. Physiol. Opt.* 12:3–7 (1992), Greve, M. et al., *Can. J. Ophthamol.* 28:201–206 (1993)). Unfortunately, because glaucomatous and normal pressure ranges overlap, such methods are of limited value unless multiple readings are obtained (Hitchings, R. A., *Br. J. Ophthamol.* 77:326 (1993); Tuck, M. W. et al., *Ophthal. Physiol. Opt.* 13:227–232 (1993); Vaughan, D. et al., In: *General Ophthamology,* Appleton & Lange, Norwalk, Conn., pp. 213–230 (1992); Vernon, S. A., *Eye* 7:134–137 (1993)). For this reason, additional methods, such as direct examination of the optic disk and determination of the extent of a patient's visual field loss are often conducted to improve the accuracy of diagnosis (Greve, M. et al., *Can. J. Ophthamol.* 28:201–206 (1993)). Moreover, these techniques are of limited prognostic value.

Nguyen et al., U.S. patent application Ser. No. 08/649,432 filed May 17, 1996, now U.S. Pat. No. 5,789,169, the entire disclosure of which is hereby incorporated by reference as if set forth at length herein, disclosed a novel protein sequence highly induced by glucocorticoids in the endothelial lining cells of the human trabecular meshwork. Nguyen et al., U.S. patent application Ser. No. 08/649,432, now U.S. Pat. No. 5,789,169 also disclosed the cDNA sequence for that protein, the protein itself, molecules that bind to it, and nucleic acid molecules that encode it, and provided improved methods and reagents for diagnosing glaucoma and related disorders, as well as for diagnosing other diseases or conditions, such as cardiovascular, immunological, or other diseases or conditions that affect the expression or activity of the protein.

The present invention provides improved diagnostic agents, prognostic agents, therapeutic agents and methods.

SUMMARY OF THE INVENTION

An object of the invention is to provide a method for diagnosing glaucoma in a patient which comprises the steps: (A) incubating under conditions permitting nucleic acid hybridization: a marker nucleic acid molecule, said marker nucleic acid molecule comprising a nucleotide sequence of a polynucleotide that specifically hybridizes to a polynucleotide that is linked to a TIGR promoter, and a complementary nucleic acid molecule obtained from a cell or a bodily fluid of said patient, wherein nucleic acid hybridization between said marker nucleic acid molecule, and said complementary nucleic acid molecule obtained from said patient permits the detection of a polymorphism whose presence is predictive of a mutation affecting TIGR response in said patient; (B) permitting hybridization between said marker nucleic acid molecule and said complementary nucleic acid molecule obtained from said patient; and (C) detecting the presence of said polymorphism, wherein the detection of the polymorphism is diagnostic of glaucoma.

Another object of the invention is to provide a method for prognosing glaucoma in a patient which comprises the steps: (A) incubating under conditions permitting nucleic acid hybridization: a marker nucleic acid molecule, said marker nucleic acid molecule comprising a nucleotide sequence of a polynucleotide that specifically hybridizes to a polynucleotide that is linked to a TIGR promoter, and a complementary nucleic acid molecule obtained from a cell or a bodily fluid of said patient, wherein nucleic acid hybridization between said marker nucleic acid molecule, and said complementary nucleic acid molecule obtained from said patient permits the detection of a polymorphism whose presence is predictive of a mutation affecting TIGR response in said patient; (B) permitting hybridization between said marker nucleic acid molecule and said complementary nucleic acid molecule obtained from said patient; and (C) detecting the presence of said polymorphism, wherein the detection of the polymorphism is prognostic of glaucoma.

Another object of the invention is to provide marker nucleic acid molecules capable of specifically detecting TIGRmt1, TIGRmt2, TIGRmt3, TIGRmt4, TIGRmt5 and TIGRsv1.

Another object of the invention is to provide a method for diagnosing steroid sensitivity in a patient which comprises the steps: (A) incubating under conditions permitting nucleic acid hybridization: a marker nucleic acid molecule, the marker nucleic acid molecule comprising a nucleotide sequence of a polynucleotide that is linked to a TIGR promoter, and a complementary nucleic acid molecule obtained from a cell or a bodily fluid of the patient, wherein nucleic acid hybridization between the marker nucleic acid molecule, and the complementary nucleic acid molecule obtained from the patient permits the detection of a polymorphism whose presence is predictive of a mutation affecting TIGR response in the patient; (B) permitting hybridization between said TIGR-encoding marker nucleic acid molecule and the complementary nucleic acid molecule obtained from the patient; and (C) detecting the presence of the polymorphism, wherein the detection of the polymorphism is diagnostic of steroid sensitivity.

Further objects of the invention provide a nucleic acid molecule that comprises the sequence of SEQ ID NO: 1, recombinant DNA molecules containing a polynucleotide that specifically hybridizes to SEQ ID NO: 1 and substantially purified molecules that specifically bind to a nucleic acid molecule that comprises the sequence of SEQ ID NO: 1.

Further objects of the invention provide a nucleic acid molecule that comprises the sequence of SEQ ID NO: 3, recombinant DNA molecules containing a polynucleotide that specifically hybridizes to SEQ ID NO: 3 and substantially purified molecules that specifically bind to a nucleic acid molecule that comprises the sequence of SEQ ID NO: 3.

Additional objects of the invention provide a nucleic acid molecule that comprises the sequence of SEQ ID NO: 4, recombinant DNA molecules containing a polynucleotide that specifically hybridizes to SEQ ID NO: 4 and substantially purified molecules that specifically bind to a nucleic acid molecule that comprises the sequence of SEQ ID NO: 4.

Additional objects of the invention provide a nucleic acid molecule that comprises the sequence of SEQ ID NO: 5, recombinant DNA molecules containing a polynucleotide that specifically hybridizes to SEQ ID NO: 5 and substantially purified molecules that specifically bind to a nucleic acid molecule that comprises the sequence of SEQ ID NO: 5.

An additional object of the present invention is to provide a method of treating glaucoma which comprises administering to a glaucomatous patient an effective amount of an agent that inhibits the synthesis of a TIGR protein.

Indeed, the molecules of the present invention may be used to diagnose diseases or conditions which are characterized by alterations in the expression of extracellular proteins.

BRIEF DESCRIPTION OF THE FIGURES

FIGS. 1A, 1B, 1C, 1D and 1E provide the nucleic acid sequence of a TIGR promoter region (SEQ ID NO: 1) from an individual without glaucoma.

FIGS. 2A, 2B, 2C and 2D provide the location and sequence changes highlighted in bold associated with glaucoma mutants TIGRmt1, TIGRmt2, TIGRmt3, TIGRmt4, TIGRmt5, and TIGRsv1 (SEQ ID NO: 2).

FIGS. 3A, 3B, 3C, 3D, 3E, 3F, and 3G provide nucleic acid sequences of a TIGR promoter, and TIGR exons, TIGR introns and TIGR downstream sequences (SEQ ID NO: 3, SEQ ID NO: 4, and SEQ ID NO: 5).

FIG. 6 provides a homology analysis of TIGR homology with olfactomedin and olfactomedin-related proteins (SEQ ID NO: 27–31).

FIG. 7 shows the nucleotide sequence of TIGR (SEQ ID NO: 26).

FIG. 8 shows the amino acid sequence of TIGR (SEQ ID NO: 32).

DETAILED DESCRIPTION OF THE INVENTION

I. Agents of the Invention

Figure 4:
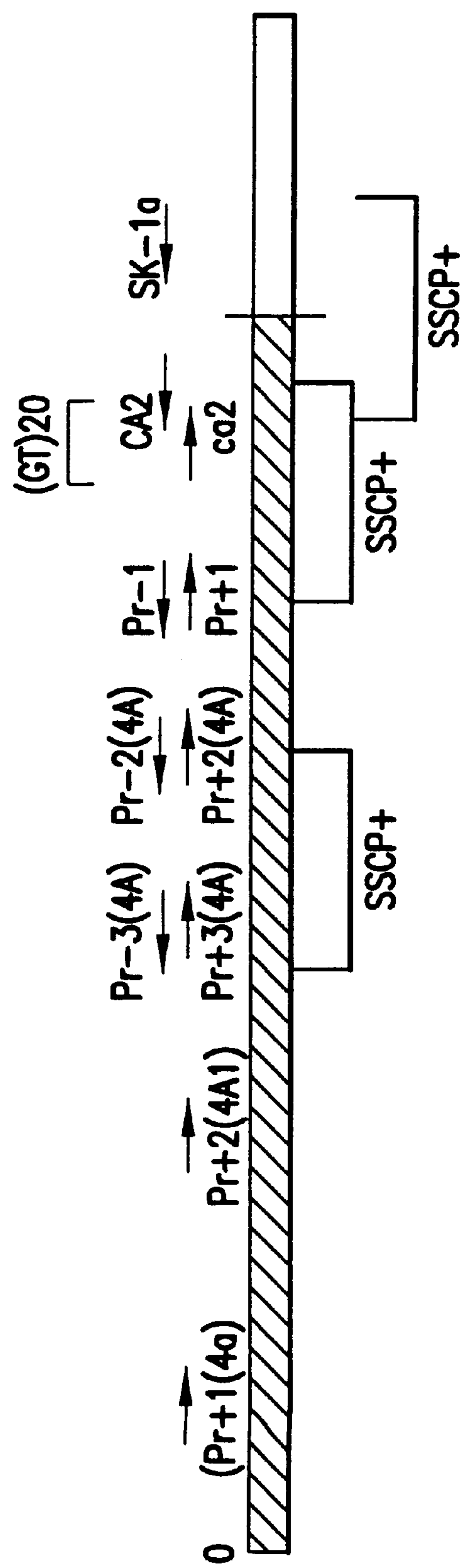
FIG. 4 provides a diagrammatic representation of the location of primers on the TIGR gene promoter for Single Strand Conformational Polymorphism (SSCP) analysis.

As used herein, the term "glaucoma" has its art recognized meaning, and includes both primary glaucomas, secondary glaucomas, juvenile glaucomas, congenital glaucomas, and familial glaucomas, including, without limitation, pigmentary glaucoma, high tension glaucoma and low tension glaucoma and their related diseases. The methods of the present invention are particularly relevant to the diagnosis of POAG, OAG, juvenile glaucoma, and inherited glaucomas. The methods of the present invention are also particularly relevant to the prognosis of POAG, OAG, juvenile glaucoma, and inherited glaucomas. A disease or condition is said to be related to glaucoma if it possesses or exhibits a symptom of glaucoma, for example, an increased intra-ocular pressure resulting from aqueous outflow resistance (see, Vaughan, D. et al., In: *General Ophthamology,* Appleton & Lange, Norwalk, Conn., pp. 213–230 (1992)). The preferred agents of the present invention are discussed in detail below.

The agents of the present invention are capable of being used to diagnose the presence or severity of glaucoma and its related diseases in a patient suffering from glaucoma (a "glaucomatous patient"). The agents of the present invention are also capable of being used to prognose the presence or severity of glaucoma and its related diseases in a person not yet suffering from any clinical manifestations of glaucoma. Such agents may be either naturally occurring or non-naturally occurring. As used herein, a naturally occurring molecule may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

As used herein, the term "TIGR protein" refers to a protein having the amino acid sequence of SEQ ID NO: 32. As used herein, the agents of the present invention comprise nucleic acid molecules, proteins, and organic molecules.

As indicated above, the trabecular meshwork has been proposed to play an important role in the normal flow of the aqueous, and has been presumed to be the major site of outflow resistance in glaucomatous eyes. Human trabecular meshwork (HTM) cells are endothelial like cells which line the outflow channels by which aqueous humor exits the eye; altered synthetic function of the cells may be involved in the pathogenesis of steroid glaucoma and other types of glaucoma. Sustained steroid treatment of these cells are interesting because it showed that a major difference was observed when compared to 1–2 day glucocorticoid (GC) exposure. This difference appears relevant to the clinical onset of steroid glaucoma (1–6 weeks).

Although trabecular meshwork cells had been found to induce specific proteins in response to glucocorticoids (see, Polansky, J. R., In: "Basic *Aspects of Glaucoma Research III*", Schattauer, N.Y. 307–318 (1993)), efforts to purify the expressed protein were encumbered by insolubility and other problems. Nguyen, T. D. et al., (In: "*Basic Aspects of Glaucoma Research III*", Schattauer, N.Y., 331–343 (1993), herein incorporated by reference) used a molecular cloning approach to isolate a highly induced mRNA species from glucocorticoid-induced human trabecular cells. The mRNA exhibited a time course of induction that was similar to the glucocorticoid-induced proteins. The clone was designated "II.2" (ATCC No. 97994, deposited on Apr. 18, 1997, American Type Culture Collection, Manassas, Va.

Nguyen et al., U.S. patent application Ser. No. 08/649,432 filed May 17, 1996, now U.S. Pat. No. 5,789,169, isolated a 11.2 clone which encoded a novel secretory protein that is induced in cells of the trabecular meshwork upon exposure to glucocorticoids. It has been proposed that this protein may become deposited in the extracellular spaces of the trabecular meshwork and bind to the surface of the endothelial cells that line the trabecular meshwork, thus causing a decrease in aqueous flow. Quantitative dot blot analysis and PCR evaluations have shown that the mRNA exhibits a progressive induction with time whereas other known GC-inductions from other systems and found in HTM cells (metallothionein, alpha-1 acid glycoprotein and alpha-1 antichymotrypsin) reached maximum level at one day or earlier. Of particular interest, the induction level of this clone was very high (4–6% total cellular mRNA) with control levels undetectable without PCR method. Based on studies of $^{35}$S methionine cell labeling, the clone has the characteristics recently discovered for the major GC-induced extracellular glycoprotein in these cells, which is a sialenated, N-glycosylated molecule with a putative inositol phosphate anchor. The induction of mRNA approached 4% of the total cellular mRNA. The mRNA increased progressively over 10 days of dexamethasone treatment. The 11.2 clone is 2.0 Kb whereas the Northern blotting shows a band of 2.5 Kb. Although not including a poly A tail, the 3' end of the clone contains two consensus polyadenylation signals.

A genomic clone was isolated and designated P,TIGR clone (ATCC No. 97570, deposited on May 14, 1996, American Type Culture Collection, Manassas, Va. In-situ hybridization using the PITIGR clone shows a TIGR gene and/or a sequence or sequences that specifically hybridize to the TIGR gene located at chromosome 1, q21–27, and more preferably to the TIGR gene located at chromosome 1, q22–26, and most preferably to the TIGR gene located at chromosome 1, q24. Clone $P_1$TIGR comprises human genomic sequences that specifically hybridize to the TIGR gene cloned into the BamHI site of vector pCYPAC (Ioannou et al., *Nature Genetics,* 6:84–89 (1994) herein incorporated by reference).

As used herein, the term "TIGR gene" refers to the region of DNA involved in producing a TIGR protein; it includes, without limitation, regions preceeding and following the coding region as well as intervening sequences between individual coding regions.

As used herein, the term "TIGR exon" refers to any interrupted region of the TIGR gene that serves as a template for a mature TIGR mRNA molecule. As used herein, the term "TIGR intron" refers to a region of the TIGR gene which is non-coding and serves as a template for a TIGR mRNA molecule.

Localization studies using a Stanford G3 radiation hybrid panel mapped the TIGR gene near the D1S2536 marker with a LOD score of 6.0 (Richard et al., *American Journal of Human Genetics* 52.5: 915–921 (1993), herein incorporated by reference); Frazer et al., *Genomics* 14.3: 574–578 (1992), herein incorporated by reference; Research Genetics, Huntsville, Ala.). Other markers in this region include: DlS210; DIS1552; D1S2536; DlS2790; SHGC-12820; and D1S2558.

Sequences located upstream of the TIGR coding region are isolated and sequenced in a non-glaucomic individual. The upstream sequence is set forth in SEQ ID. No. 1. Sequence comparisons of the upstream region of a non-glaucoma individual and individuals with glaucoma identify a number of mutations in individuals with glaucoma. These mutations are illustrated in FIG. 2. Five mutations are identified. TIGRmt1 is the result of a replacement of a cytosine with a guanine at position 4337 (SEQ ID NO: 1, SEQ ID NO: 2, and SEQ ID NO: 3). TIGRmt2 is the result of a replacement of a cytosine with a thymine at position 4950 (SEQ ID NO: 1, SEQ ID NO: 2, and SEQ ID NO: 3). TIGRmt3 is the result of an addition in the following order of a guanine, a thymine, a guanine, and a thymine (GTGT) at position 4998 (SEQ ID NO: 1, SEQ ID NO: 2, and SEQ ID NO: 3). TIGRmt4 is the result of a replacement of an adenine with a guanine at position 4256 (SEQ ID NO: 1, SEQ ID NO: 2, and SEQ ID NO: 3). TIGRmt5 is the result of a replacement of a guanine with an adenine at position 4262 (SEQ ID NO: 1, SEQ ID NO: 2 and SEQ ID NO: 3). One or more of TIGRmt1, TIGRmt2, TIGRmt3, TIGRmt4, and TIGRmt5 can be homozygous or heterozygous.

Sequence comparisons of the upstream region of a non-glaucoma individual and individuals with glaucoma identify at least one sequence variation in individuals with glaucoma. One such sequence variant is illustrated in FIG. 2. TIGRsv1 is the result of a replacement of an adenine with a guanine at position 4406 (SEQ ID NO: 1, SEQ ID NO: 2 and SEQ ID NO: 3).

Molecules comprising sequences upstream of the TIGR coding region provide useful markers for polymorphic studies. Such molecules include primers suitable for single strand conformational polymorphic studies, examples of which are as follows: forward primer "Sk-1a": 5'-TGA GGC TTC CTC TGG AAA C-3' (SEQ ID NO: 6); reverse primer "ca2": 5'-TGA AAT CAG CAC ACC AGT AG-3' (SEQ ID NO: 7); forward primer "CA2": 5'-GCA CCC ATA CCC CAA TAA TAG-3' (SEQ ID NO: 8); reverse primer "Pr+1": 5'-AGA GTT CCC CAG ATT TCA CC-3' (SEQ ID NO: 9); forward primer "Pr-1": 5'-ATC TGG GGA ACT CTT CTC AG-3' (SEQ ID NO: 10); reverse primer "Pr+2 (4A2)": 5'-TAC AGT TGT TGC AGA TAC G-3' (SEQ ID NO: 11); forward primer "Pr−2(4A)": 5'-ACA ACG TAT CTG CAA CAA CTG-3' (SEQ ID NO: 12); reverse primer "Pr+3(4A)": 5'-TCA GGC TTA ACT GCA GAA CC-3' (SEQ ID NO: 13); forward primer "Pr−3(4A)": 5'-TTG GTT CTG CAG TTA AGC C-3' (SEQ ID NO: 14); reverse primer "Pr+2(4A1)": 5'-AGC AGC ACA AGG GCA ATC C-3' (SEQ ID NO: 15); reverse primer "Pr+1(4A)": 5'-ACA GGG CTA TAT TGT GGG-3' (SEQ ID NO: 16).

In addition, molecules comprising sequences within TIGR exons provide useful markers for polymorphic studies. Such molecules include primers suitable for single strand conformational polymorphic studies, examples of which are as follows: forward primer "KS1X": 5'-CCT GAG ATG CCA GCT GTC C-3' (SEQ ID NO: 17); reverse primer "SK1XX": 5'-CTG AAG CAT TAG AAG CCA AC-3' (SEQ ID NO: 18); forward primer "KS2a1": 5'-ACC TTG GAC CAG GCT GCC AG-3' (SEQ ID NO: 19); reverse primer "SK3"5'-AGG TTT GTT CGA GTT CCA G-3' (SEQ ID NO: 20); forward primer "KS4": 5'-ACA ATT ACT GGC AAG TAT GG-3' (SEQ ID NO: 21); reverse primer "SK6A": 5'-CCT TCT CAG CCT TGC TAC C-3' (SEQ ID NO: 22); forward primer "KS5": 5'-ACA CCT CAG CAG ATG CTA CC-3' (SEQ ID NO: 23); reverse primer "SK8": 5'-ATG GAT GAC TGA CAT GGC C-3' (SEQ ID NO: 24); forward primer "KS6": 5'-AAG GAT GAA CAT GGT CAC C-3' (SEQ ID NO: 25).

Figure 5:
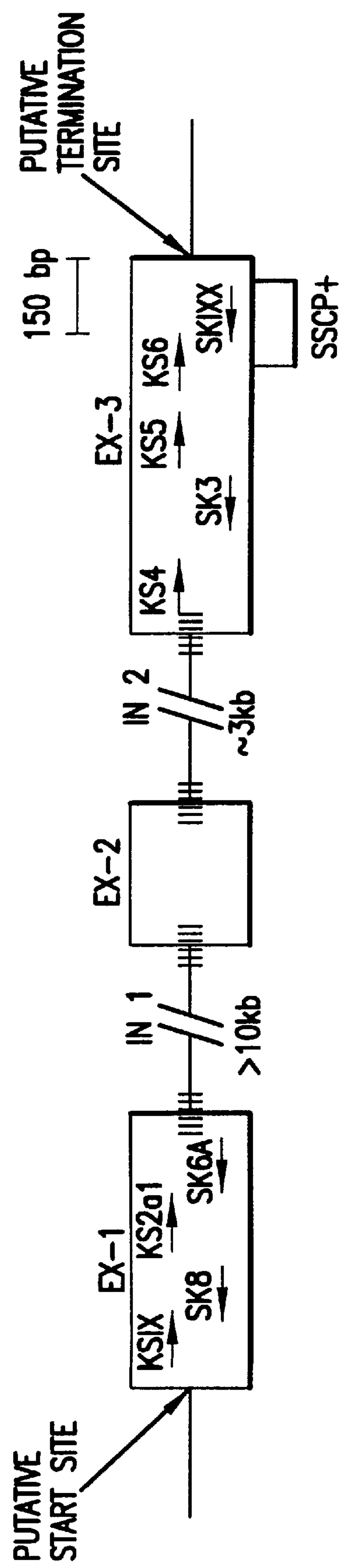
FIG. 5 provides a diagrammatic representation of the TIGR exons and the arrangement of SSCP primers.

The locations of primers: Sk−1a, ca2, CA2, Pr+1, Pr−1, Pr+2(4A2), Pr−2(4A), Pr+3(4A), Pr−3(4A), Pr−3(4A), Pr+2 (4A1), and Pr+1(4A) are diagramatically set forth in FIG. 4. The location of primers: KS1X, SKlXX, Ks2a1, SK3, KS4, SK6A, KS5, SK8, and KS6 are diagramatically set forth in FIG. 5.

The primary structure of the TIGR coding region initiates from an ATG initiation site (SEQ ID NO:3, residues 5337–5339) and includes a 20 amino acid consensus signal sequence a second ATG (SEQ ID NO: 3, residues 5379–5381), indicating that the protein is a secretory protein. The nucleotide sequence for the TIGR coding region is depicted in FIG. 7 (SEQ ID NO: 26). The protein contains an N-linked glycosylation site located in the most hydrophilic region of the molecule. The amino terminal portion of the protein is highly polarized and adopts alpha helical structure as shown by its hydropathy profile and the Gamier-Robison structure analysis. In contrast, the protein contains a 25 amino acid hydrophobic region near its carboxy terminus. This region may comprise a glucocorticoid-induced protein (GIP) anchoring sequence. The amino acid sequence of TIGR is depicted in FIG. 8 (SEQ ID NO: 33).

Study of cyclohexamide treatment in the absence and presence of GC suggest that the induction of TIGR may involve factors in addition to the GC receptor. The TIGR gene may be involved in the cellular stress response since it is also induced by stimulants such as $H_2O_2$, 12-O-tetradecanolyphorbol-13-acetate (TPA), and high glucose; this fact may relate to glaucoma pathogenesis and treatment.

Sequence comparison of the upstream region identify a number of DNA motifs (cis elements). These DNA motifs or cis elements are shown in FIG. 1. These motifs include, without limitation, glucocorticoid response motif(s), shear stress response motif(s), NFκB recognition motif(s), and AP1 motif(s). The locations of these and other motifs are diagramatically set forth in FIG. 1. As used herein, the term "cis elements capable of binding" refers to the ability of one or more of the described cis elements to specifically bind an agent. Such binding may be by any chemical, physical or biological interaction between the cis element and the agent, including, but not limited, to any covalent, steric, agostic, electronic and ionic interaction between the cis element and the agent. As used herein, the term "specifically binds" refers to the ability of the agent to bind to a specified cis element but not to wholly unrelated nucleic acid sequences.

A preferred class of agents comprises TIGR nucleic acid molecules ("TIGR molecules"). Such molecules may be either DNA or RNA. A second preferred class of agents ("TIGR molecules") comprises the TIGR protein, its peptide fragments, fusion proteins, and analogs.

Expression of the rat PRL gene is highly restricted to pituitary lactotroph cells and is induced by the cAMP-dependent protein kinase A pathway. At least one of the redundant pituitary specific elements (PRL-FP111) of the proximal rat PRL promotor is required for this protein kinase A effect (Rajnarayan et al., *Molecular Endochronology* 4: 502–512 (1995), herein incorporated by reference). A sequence corresponding to an upstream motif or cis element characteristic of PRL-FP111 is set forth in FIG. 1 at residues 370–388 and 4491–4502, respectively. In accordance with the embodiments of the present invention, transcription of TIGR molecules can be effected by agents capable of altering the biochemical properties or concentration of molecules that bind the PRL-FL111 upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence (GR/PR), recognized by both the glucocorticoid receptor of rat liver and the progesterone receptor from rabbit uterus, has been reported to be involved in glucocorticoid and progesterone-dependent gene expression (Von der Ahe et al., *Nature* 313: 706–709 (1985), herein incorporated by reference). A sequence corresponding to a GC/PR upstream motif or cis element is set forth in FIG. 1 at residues 433–445. In accordance with the embodiments of the present invention, transcription of TIGR molecules can be effected by agents capable of altering the biochemical properties or concentration of glucocorticoid or progesterone or their homologues, including, but not limited to, the concentration of glucocorticoid or progesterone or their homologues bound to an GC/PR upstream motif or cis element. Such agents can be used in the study of glaucoma pathogenesis. In another embodiment, such agents can also be used in the study of glaucoma prognosis. In another embodiment such agents can be used in the treatment of glaucoma.

Shear stress motif (SSRE) or cis element has been identified in a number of genes including platelet-derived growth factor B chain, tissue plasminogen activator (tPA), ICAM-1 and TGF-β1 (Resnick et al., *Proc. Natl. Acad. Sci.* (*USA*) 80: 4591–4595 (1993), herein incorporated by reference). Transcription of these genes has been associated with humoral stimuli such as cytokines and bacterial products as well as hemodynamic stress forces. Sequences corresponding to a upstream shear stress motif or cis element are set forth in FIG. 1 at residues 446–451, 1288–1293, 3597–3602, 4771–4776, and 5240–5245, respectively. In accordance with the embodiments of the present invention, transcription of TIGR molecules can be effected by agents capable of altering the biochemical properties or concentration of molecules capable of binding the shear stress motif. Such agents can be used in the study of glaucoma pathogenesis. In another embodiment, such agents can also be used in the study of glaucoma prognosis. In another embodiment such agents can be used in the treatment of glaucoma.

A consensus sequence for a glucocorticoid response upstream motif (GRE) or cis element has been characterized (Beato, *Cell* 56: 335–344 (1989); Becker et al., *Nature* 324: 686–688 (1986), herein incorporated by reference; Sakai et al., *Genes and Development* 2: 1144–1154 (1988), herein incorporated by reference). Genes containing this upstream motif or cis element are regulated by glucocorticoids, progesterone, androgens and mineral corticoids (Beato, *Cell* 56: 335–344 (1989)). Sequences corresponding to glucocorticoid response upstream motif or cis element are set forth in FIG. 1 at residues 574–600, 1042–1056, 2444–2468, 2442–2269, 3536–3563, 4574–4593, 4595–4614, 4851–4865, 4844–4864, 5079–5084, and 5083–5111, respectively. In accordance with the embodiments of the present invention, transcription of TIGR molecules can be effected by agents capable of altering the biochemical properties or concentration of molecules capable of binding a glucocorticoid response upstream motif or cis element. Such agents can be used in the study of glaucoma pathogenesis. In another embodiment, such agents can also be used in the study of glaucoma prognosis. In another embodiment such agents can be used in the treatment of glaucoma.

A sequence specific binding site (CBE) for the wild type nuclear phosphoprotein, p53, has been identified and appears to be associated with replication origins (Kern et al. *Science* 252: 1708–1711 (1991), herein incorporated by reference). A sequence corresponding to an CBE upstream motif or cis element is set forth in FIG. 1 at residues 735–746. In accordance with the embodiments of the present invention, transcription of TIGR molecules can be effected by agents capable of altering the biochemical properties or concentration of p53 or its homologues, including, but not limited to, the concentration of p53 or its homologues bound to an CBE upstream motif or cis element. Such agents can be used in the study of glaucoma pathogenesis. In another embodiment, such agents can also be used in the study of glaucoma prognosis. In another embodiment such agents can be used in the treatment of glaucoma.

Nuclear factor ets-like (NFE), a transcriptional activator that facilitates p50 and c-Rel-dependent IgH 3' enhancer activity has been shown to bind to an NFE site in the Rel-dependent IgH 3' enhancer (Linderson et al., *European J. Immunology* 27: 468–475 (1997), herein incorporated by reference). A sequence corresponding to an NFE upstream motif or cis element is set forth in FIG. 1 at residues 774–795. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an NFE upstream motif or cis element. Such agents can be used in the study of glaucoma pathogenesis. In another embodiment, such agents can also be used in the study of glaucoma prognosis. In another embodiment such agents can be used in the treatment of glaucoma.

An upstream motif or cis element (KTF.1-CS) for a control element 3' to the human keratin 1 gene that regulates cell type and differentiation-specific expression has been identified (Huff et al., *J. Biological Chemistry* 268: 377–384 (1993), herein incorporated by reference). A sequence corresponding to an upstream motif or cis element characteristic of KTF.1-CS is set forth in FIG. 1 at residues 843–854. In accordance with the embodiments of the present invention, transcription of TIGR molecules can be effected by agents capable of altering the biochemical properties or concentration of KTF.1-CS or its homologues, including, but not limited to, the concentration of KTF.1-CS or its homologues bound to a KTF.1-CS upstream motif or cis element Such agents can be used in the study of glaucoma pathogenesis. In another embodiment, such agents can also be used in the study of glaucoma prognosis. In another embodiment such agents can be used in the treatment of glaucoma.

A progesterone responsive element (PRE) that maps to the far upstream steroid dependent DNase hypersensitive site of chicken lysozyme chromatin has been characterized (Hecht et al., *EMBO J.* 7: 2063–2073 (1988), herein incorporated by reference). The element confers hormonal regulation to a heterologous promoter and is composed of a cluster of progesterone receptor binding sites. A sequence corresponding to an upstream motif or cis element characteristic of PRE is set forth in FIG. 1 at residues 987–1026. In accordance with the embodiments of the present invention, transcription of TIGR molecules can be effected by agents capable of altering the biochemical properties or concentration of molecules capable of binding a progesterone responsive PRE upstream motif or cis element. Such agents may be useful in the study of glaucoma pathogenesis. In another embodiment, such agents can also be used in the study of glaucoma prognosis. In another embodiment such agents can be used in the treatment of glaucoma.

A sequence (ETF-EGFR) has been characterized which serves as a motif for a trans-active transcription factor that regulates expression of the epidermal growth factor receptor (Regec et al., *Blood* 85:2711–2719 (1995), herein incorporated by reference). A sequence corresponding to an ETF-EGFR upstream motif or cis element is set forth in FIG. 1 at residues 1373–1388. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an ETF-EGFR upstream motif or cis element. Such agents can be used in the study of glaucoma pathogenesis. In another embodiment, such agents can also be used in the study of glaucoma prognosis. In another embodiment such agents can be used in the treatment of glaucoma.

A common trans-acting factor (SRE-cFos) has been shown to regulate skeletal and cardiac alpha-Actin gene transcription in muscle (Muscat et al., *Molecular and Cellular Biology* 10: 4120–4133 (1988), herein incorporated by reference). A sequence corresponding to an SRE-cFos upstream motif or cis element is set forth in FIG. 1 at residues 1447–1456. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an SRE-cFos upstream motif or cis element. Such agents can be used in the study of glaucoma pathogenesis. In another embodiment, such agents can also be used in the study of glaucoma prognosis. In another embodiment such agents can be used in the treatment of glaucoma.

Alu repetitive elements are unique to primates and are interspersed within the human genome with an average spacing of 4Kb. While some Alu sequences are actively transcribed by polymerase III, normal transcripts may also contain Alu-derived sequences in 5' or 3' untranslated regions (jurka and Mikahanljaia, *J. Mol. Evolution* 32: 105–121 (1991), herein incorporated by reference, Claveria and Makalowski, *Nature* 371: 751–752 (1994), herein incorporated by reference). A sequence corresponding to an Alu upstream motif or cis element is set forth in FIG. 1 at residues 1331–1550. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an Alu upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for a vitellogenin gene-binding protein (VBP) upstream motif or cis element has been characterized (Iyer et al., *Molecular and Cellular Biology* 11: 4863–4875 (1991), herein incorporated by reference). Expression of the VBP gene commences early in liver ontogeny and is not subject to circadian control. A sequence corresponding to an upstream motif or cis element capable of binding VBP is set forth in FIG. 1 at residues 1786–1797. In accordance with the embodiments of the present invention, transcription of TIGR molecules can be effected by agents capable of altering the biochemical properties or concentration of VBP or its homologues, including, but not limited to, the concentration of VBP or its homologues bound to an VBP upstream motif or cis element Such agents can be used in the study of glaucoma pathogenesis. In another embodiment, such agents can also be used in the study of glaucoma prognosis. In another embodiment such agents can be used in the treatment of glaucoma.

A structural motif (Malt-CS) or cis element involved in the activation of all promoters of the maltose operons in Escherichia coli and Klebsiella pneumoniae has been characterized (Vidal-Ingigliardi et al., *J. Mol. Biol.* 218: 323–334 (1991), herein incorporated by reference). A sequence corresponding to a upstream Malt-CS motif or cis element is set forth in FIG. 1 at residues 1832–1841. In accordance with the embodiments of the present invention, transcription of TIGR molecules can be effected by agents capable of altering the biochemical properties or concentration of molecules capable of binding the upstream Malt-CS motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for an estrogen receptor upstream motif or cis element has been characterized (ERE) (Forman et al., *Mol. Endocrinology* 4: 1293–1301 (1990), herein incorporated by reference; de Verneuil et al., *Nucleic Acid Res.* 18: 4489–4497 (1990), herein incorporated by reference; Gaub et al., *Cell* 63: 1267–1276 (1990), herein incorporated by reference. A sequence corresponding to half an upstream motif or cis element capable of binding estrogen receptor is set forth in FIG. 1 at residues 2166–2195, 3413–3429, and 3892–3896, respectively. In accordance with the embodiments of the present invention, transcription of TIGR molecules can be effected by agents capable of altering the biochemical properties or concentration, of the estrogen receptor or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Certain protein-binding sites (NF-mutagen) in Ig gene enhancers which determine transcriptional activity and inducibility have been shown to interact with nuclear factors (Lenardo et al., *Science* 236: 1573–1577 (1987), herein incorporated by reference). A sequence corresponding to an NF-mutagen upstream motif or cis element is set forth in FIG. 1 at residues 2329–2338. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an NF-mutagen upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for a transcriptional repressor of c-myc (myc-PRF) upstream motif or cis element has been identified (Kakkis et al., *Nature* 339: 718–719 (1989), herein incorporated by reference). Myc-PRF interacts with another widely distributed protein, myc-CF1 (common factor 1), which binds nearby and this association may be important in myc-PRF repression. A sequence corresponding to an upstream motif or cis element capable of binding myc-PRF is set forth in FIG. 1 at residues 2403–2416. In accordance with the embodiments of the present invention, transcription of TIGR molecules can be effected by agents capable of altering the biochemical properties or concentration of myc-PRF or its homologues, including, but not limited to, the concentration of myc-PRF or its homologues bound to an myc-PRF upstream motif or cis element Such agents can be used in the study of glaucoma pathogenesis. In another embodiment, such agents can also be used in the study of glaucoma prognosis. In another embodiment such agents can be used in the treatment of glaucoma.

Human transcription factor activator protein 2 (AP2) is a transcription factor that has been shown to bind to Sp1, nuclear factor 1 (NF1) and simian virus 40 transplantation (SV40 T) antigen binding sites. It is developmentally regulated (Williams and Tijan, *Gene Dev.* 5: 670–682 (1991), herein incorporated by reference; Mitchell et al., *Genes Dev.* 5: 105–119 (1991), herein incorporated by reference; Coutois et al., *Nucleic Acid Research* 18: 57–64 (1990), herein incorporated by reference; Comb et al., *Nucleic Acid Research* 18: 3975–3982 (1990), herein incorporated by reference; Winings et al., *Nucleic Acid Research* 19: 3709–3714 (1991), herein incorporated by reference). Sequences corresponding to an upstream motif or cis element capable of binding AP2 are set forth in FIG. 1 at residues 2520–2535, and 5170–5187, respectively. In accordance with the embodiments of the present invention, transcription of TIGR molecules can be effected by agents capable of altering the biochemical properties or concentration of AP2 or its homologues, including, but not limited to, the concentration of AP2 or its homologues bound to an upstream motif or cis element. Such agents may be useful in the study of glaucoma pathogenesis. In another embodiment, such agents can also be used in the study of glaucoma prognosis. In another embodiment such agents can be used in the treatment of glaucoma.

Drosophila RNA polymerase II heat shock transcription factor (HSTF) is a transcription factor that has been shown to be required for active transcription of an hsp 70 gene (Parker and Topol, *Cell* 37: 273–283 (1984), herein incorporated by reference). Sequences corresponding to an upstream motif or cis element capable of binding HSTF are set forth in FIG. 1 at residues 2622–2635, and 5105–5132. In accordance with the embodiments of the present invention, transcription of TIGR molecules can be effected by agents capable of altering the biochemical properties or concentration of HSTF or its homologues, including, but not limited to, the concentration of HSTF or its homologues bound to an HSTF upstream motif or cis element. Such agents can be used in the study of glaucoma pathogenesis. In another embodiment, such agents can also be used in the study of glaucoma prognosis. In another embodiment such agents can be used in the treatment of glaucoma.

A sequence corresponding to an upstream motif or cis element characteristic of SBF is set forth in FIG. 1 at residues 2733–2743 (Shore et al., *EMBO J.* 6: 461–467 (1987), herein incorporated by reference). In accordance with the embodiments of the present invention, transcription of TIGR molecules can be effected by agents capable of altering the biochemical properties or concentration of molecules that bind the SBF upstream motif or cis element. Such agents can be used in the study of glaucoma pathogenesis. In another embodiment, such agents can also be used in the study of glaucoma prognosis. In another embodiment such agents can be used in the treatment of glaucoma.

An NF1 motif or cis element has been identified which recognizes a family of at least six proteins (Courtois, et al., *Nucleic Acid Res.* 18: 57–64 (1990), herein incorporated by reference; Mul et al., *J. Virol.* 64: 5510–5518 (1990), herein incorporated by reference; Rossi et al., *Cell* 52: 405–414 (1988), herein incorporated by reference; Gounari et al., *EMBO J.* 10: 559–566 (1990), herein incorporated by reference; Goyal et al., *Mol. Cell Biol.* 10: 1041–1048 (1990); herein incorporated by reference; Mermond et al., *Nature* 332: 557–561 (1988), herein incorporated by reference; Gronostajski et al., *Molecular and Cellular Biology* 5: 964–971 (1985), herein incorporated by reference; Hennighausen et al., *EMBO J.* 5: 1367–1371 (1986), herein incorporated by reference; Chodosh et al., *Cell* 53: 11–24 (1988), herein incorporated by reference). The NF1 protein will bind to an NF1 motif or cis element either as a dimer (if the motif is palindromic) or as an single molecule (if the motif is not palindromic). The NF1 protein is induced by TGFP (Faisst and Meyer, *Nucleic Acid Research* 20: 3–26 (1992), herein incorporated by reference). Sequences corresponding to an upstream motif or cis element capable of binding NF1 are set forth in FIG. 1 at residues 2923–2938, 4143–4167, and 4886–4900, respectively. In accordance with the embodiments of the present invention, transcription of TIGR molecules can be effected by agents capable of altering the biochemical properties or concentration of NF1 or its homologues, including, but not limited to, the concentration of NF1 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Conserved regulatory sequences (NF-MHCIIA/B) of a rabbit major histocompatability complex (MHC) class II gene are responsible for binding two distinct nuclear factors NF-MHCIIA and NF-MHCIIB and are believed to be involved in the regulation of coordinate expression of the class II genes—eg. MHC class II gene in B lymphocytes (Sittisombut *Molecular and Cellular Biology* 5: 2034–2041 (1988), herein incorporated by reference). A sequence corresponding to an NF-MHCIIA/B upstream motif or cis element is set forth in FIG. 1 at residues 2936–2944. In accordance with the embodiments of the present invention, transcription of TIGR molecules can be effected by agents capable of altering the biochemical properties or concentration of NF-MHCIIA or NF-MHCIIB or their homologues, including, but not limited to, the concentration of NF-MHCIIA or NF-MHCIIB or their homologues bound to an NF-MHCIIA/B upstream motif or cis element. Such agents can be used in the study of glaucoma pathogenesis. In another embodiment, such agents can also be used in the study of glaucoma prognosis. In another embodiment such agents can be used in the treatment of glaucoma.

PEA 1 binding motifs or cis elements have been identified (Piette and Yaniv, *EMBO J.* 5: 1331–1337 (1987), herein incorporated by reference). The PEAI protein is a transcription factor that is reported to bind to both the polyoma virus and c-fos enhancers A sequence corresponding to an upstream motif or cis element capable of binding PEA1 is set forth in FIG. 1 at residues 3285–3298. In accordance with the embodiments of the present invention, transcription of TIGR molecules can be effected by agents capable of altering the biochemical properties or concentration of PEA1 or its homologues, including, but not limited to, the concentration of PEA1 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

A conserved cis-acting regulatory element (ICS) has been shown to bind transacting constituitive nuclear factors present in lymphocytes and fibroblasts which are involved in the interferon (IFN)-mediated transcriptional enhancement of MHC class I and other genes (Shirayoshi et al., *Proc. Natl. Acad. Sci.* (*USA*) 85: 5884–5888 (1988), herein incorporated by reference). A sequence corresponding to an ICS upstream motif or cis element is set forth in FIG. 1 at residues 3688–3699. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an ICS upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for an ISGF2 upstream motif or cis element has been characterized (Iman et al., *Nucleic Acids Res.* 18: 6573–6580 (1990), herein incorporated by reference; Harada et al., *Cell* 63: 303–312 (1990), herein incorporated by reference; Yu-Lee et al., *Mol. Cell Biol.* 10: 3087–3094 (1990), herein incorporated by reference; Pine et al., *Mol. Cell Biol.* 10: 32448–2457 (1990), herein incorporated by reference). ISGF2 is induced by interferon α and γ, prolactin and virus infections. A sequence corresponding to an upstream motif or cis element capable of binding ISGF2 is set forth in FIG. 1 at residues 4170–4179. In accordance with the embodiments of the present invention, transcription of TIGR molecules can be effected by agents capable of altering the biochemical properties or concentration of ISGF2 or its homologues, including, but not limited to, the concentration of ISGF2 or its homologues bound to an upstream motif or cis element Such agents can be used in the study of glaucoma pathogenesis. In another embodiment, such agents can also be used in the study of glaucoma prognosis. In another embodiment such agents can be used in the treatment of glaucoma.

A sequence corresponding to an upstream motif or cis element capable of binding zinc is set forth in FIG. 1 at residues 4285–4292. In accordance with the embodiments of the present invention, transcription of TIGR molecules can be effected by agents capable of altering the biochemical properties or concentration of zinc. Such agents can be used in the study of glaucoma pathogenesis. In another embodiment, such agents can also be used in the study of glaucoma prognosis. In another embodiment such agents can be used in the treatment of glaucoma.

A sequence corresponding to an upstream motif or cis element characteristic of CAP/CRP-galO is set forth in FIG. 1 at residues 4379–4404 (Taniguchi et al., *Proc. Natl. Acad. Sci (USA)* 76: 5090–5094 (1979), herein incorporated by reference). In accordance with the embodiments of the present invention, transcription of TIGR molecules can be effected by agents capable of altering the biochemical properties or concentration of molecules that bind the CAP/CRP-galO upstream motif or cis element. Such agents can be used in the study of glaucoma pathogenesis. In another embodiment, such agents can also be used in the study of glaucoma prognosis. In another embodiment such agents can be used in the treatment of glaucoma.

Human transcription factor activator protein 1 (AP1) is a transcription factor that has been shown to regulate genes which are highly expressed in transformed cells such as stromelysin, c-fos, $\alpha_1$-anti-trypsin and collagenase (Gutman and Wasylyk, *EMBO J.* 9.7: 2241–2246 (1990), herein incorporated by reference; Martin et al., *Proc. Natl. Acad. Sci. USA* 85: 5839–5843 (1988), herein incorporated by reference; Jones et al., *Genes and Development* 2: 267–281 (1988), herein incorporated by reference; Faisst and Meyer, *Nucleic Acid Research* 20: 3–26 (1992), herein incorporated by reference; Kim et al., *Molecular and Cellular Biology* 10: 1492–1497 (1990), herein incorporated by reference: Baumhueter et al., *EMBO J.* 7: 2485–2493 (1988), herein incorporated by reference). The AP1 transcription factor has been associated with genes that are activated by 12-O-tetradecanolyphorbol-13-acetate (TPA) (Gutman and Wasylyk, *EMBO J.* 7: 2241–2246 (1990)). Sequences corresponding to an upstream motif or cis element capable of binding AP1 are set forth in FIG. 1 at residues 4428–4434 and 4627–4639, respectively. In accordance with the embodiments of the present invention, transcription of TIGR molecules can be effected by agents capable of altering the biochemical properties or concentration of AP1 or its homologues, including, but not limited to, the concentration of AP1 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

The sex-determining region of the Y chromosome gene, sry, is expressed in the fetal mouse for a brief period, just prior to testis differentiation. SRY is a DNA binding protein known to bind to a CACA-rich region in the sry gene (Vriz et al., *Biochemistry and Molecular Biology International* 37: 1137–1146 (1995), herein incorporated by reference). A sequence corresponding to an upstream motif or cis element capable of binding SRY is set forth in FIG. 1 at residues 4625–4634. In accordance with the embodiments of the present invention, transcription of TIGR molecules can be effected by agents capable of altering the biochemical properties or concentration of SRY or its homologues, including, but not limited to, the concentration of SRY or its homologues bound to an upstream motif or cis element. Such agents may be useful in the study of glaucoma pathogenesis. In another embodiment, such agents can also be used in the study of glaucoma prognosis. In another embodiment such agents can be used in the treatment of glaucoma.

A sequence corresponding to an upstream motif or cis element characteristic of GC2-GH is set forth in FIG. 1 at residues 4689–4711 (West et al., *Molecular and Cellular Biology* 7: 1193–1197 (1987), herein incorporated by reference). In accordance with the embodiments of the present invention, transcription of TIGR molecules can be effected by agents capable of altering the biochemical properties or concentration of GC2-GH or its homologues, including, but not limited to, the concentration of GC2-GH or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

PEA 3 binding motifs or cis elements have been identified (Martin et al., *Proc. Natl. Acad. Sci.* (*USA*) 85: 5839–5843 (1988), herein incorporated by reference; Gutman and Wasylyk, *EMBO J.* 7: 2241–2246 (1990), herein incorporated by reference). The PEA3 protein is a transcription factor that is reported to interact with AP1 like proteins (Martin et al., *Proc. Natl. Acad. Sci.* (*USA*) 85: 5839–5843 (1988), herein incorporated by reference). Sequences corresponding to an upstream motif or cis element capable of binding PEA3 is set forth in FIG. 1 at residues 4765–4769. In accordance with the embodiments of the present invention, transcription of TIGR molecules can be effected by agents capable of altering the biochemical properties or concentration of PEA3 or its homologues, including, but not limited to, the concentration of PEA3 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Mammalian interspersed repetitive (MIR) is an element involved in the coding and processing sequences of mammalian genes. The MIR element is at least 260 bp in length and numbers about 105 copies within the mammalian genome (Murnane et al., *Nucleic Acids Research* 15: 2837–2839 (1995), herein incorporated by reference). A sequence corresponding to an MIR upstream motif or cis element is set forth in FIG. 1 at residues 4759–4954. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an MIR upstream motif or cis element. Such agents can be used in the study of glaucoma pathogenesis. In another embodiment, such agents can also be used in the study of glaucoma prognosis. In another embodiment such agents can be used in the treatment of glaucoma.

Normal liver and differentiated hepatoma cell lines contain a hepatocyte-specific nuclear factor (HNF-1) which binds cis-acting element sequences within the promoters of the alpha and beta chains of fibrinogen and alpha 1-antitrypsin (Baumhueter et al., *EMBO J.* 8: 2485–2493, herein incorporated by reference). A sequence corresponding to an HNF-1 upstream motif or cis element is set forth in FIG. 1 at residues 4923–4941. In accordance with the embodiments of the present invention, transcription of TIGR molecules can be effected by agents capable of altering the biochemical properties or concentration of HNF-1 or its homologues, including, but not limited to, the concentration of HNF-1 or its homologues bound to an HNF-1 upstream motif or cis element. Such agents can be used in the study of glaucoma pathogenesis. In another embodiment, such agents can also be used in the study of glaucoma prognosis. In another embodiment such agents can be used in the treatment of glaucoma.

A number of cis elements or upstream motifs have been associated with gene regulation by steroid and thyroid hormones (e.g. glucocorticoid and estrogen)(Beato, *Cell* 56: 335–344 (1989), herein incorporated by reference; Brent et al., *Molecular Endocrinology* 89:1996–2000 (1989), herein incorporated by reference; Glass et al., *Cell* 54: 313–323 (1988), herein incorporated by reference; Evans, *Science* 240: 889–895 (1988), herein incorporated by reference).

A consensus sequence for a thyroid receptor upstream motif or cis element (TRE) has been characterized (Beato, *Cell* 56: 335–344 (1989), herein incorporated by reference). A sequence corresponding to a thyroid receptor upstream motif or cis element is set forth in FIG. 1 at residues 5151–5156. Thyroid hormones are capable of regulating genes containing a thyroid receptor upstream motif or cis element (Glass et al., *Cell* 54: 313–323 (1988), herein incorporated by reference). Thyroid hormones can negatively regulate TIGR. In accordance with the embodiments of the present invention, transcription of TIGR molecules can be effected by agents capable of altering the biochemical properties or concentration of molecules capable of binding a thyroid receptor upstream motif or cis element. Such agents can be used in the study of glaucoma pathogenesis. In another embodiment, such agents can also be used in the study of glaucoma prognosis. In another embodiment such agents can be used in the treatment of glaucoma.

NFκB is a transcription factor that is reportedly associated with a number of biological processes including T-cell activation and cytokine regulation (Lenardo et al., *Cell* 58: 227–229 (1989), herein incorporated by reference). A consensus upstream motif or cis element capable of binding NFκB has been reported (Lenardo et al., *Cell* 58: 227–229 (1989)). Sequences corresponding to an upstream motif or cis element capable of binding NFκKB are set forth in FIG. 1 at residues 5166–5175. In accordance with the embodiments of the present invention, transcription of TIGR molecules can be effected by agents capable of altering the biochemical properties or concentration of NFκB or its homologues, including, but not limited to, the concentration of NFκB or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Where one or more of the agents is a nucleic acid molecule, such nucleic acid molecule may be sense, antisense or triplex oligonucleotides corresponding to any part of the TIGR promoter, TIGR cDNA, TIGR intron, TIGR exon or TIGR gene.

The TIGR promoter, or fragment thereof, of the present invention may be cloned into a suitable vector and utilized to promote the expression of a marker gene (e.g. firefly luciferase (de Wet, *Mol. Cell Biol.* 7: 725–737 (1987), herein incorporated by reference) or GUS Jefferson et al., *EMBO J.* 6: 3901–3907 (1987), herein incorporated by reference)). In another embodiment of the present invention, a TIGR promoter may be cloned into a suitable vector and utilized to promote the expression of a TIGR gene in a suitable eukaryotic or prokaryotic host cell (e.g. human trabecular cell, chinese hamster cell, *E. coli*). In another embodiment of the present invention, a TIGR promoter may be cloned into a suitable vector and utilized to promote the expression of a homologous or heterologous gene in a suitable eukaryotic or prokaryotic host cells (e.g. human trabecular cell lines, chinese hamster cells, *E. coli*).

Practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., In *Molecular Cloning: A Laboratory Manual,* Cold Spring Harbor Press (1989), herein incorporated by reference in its entirety; Old and Primrose, In Principles of Gene Manipulation: An Introduction To Genetic Engineering, Blackwell (1994), herein incorporated by reference).

The TIGR promoter or any portion thereof of the present invention may be used in a gel-retardation or band shift assay (Old and Primrose, In Principles of Gene Manipulation: An Introduction To Genetic Engineering, Blackwell (1994)). Any of the cis elements identified in the present invention may be used in a gel-retardation or band shift assay to isolate proteins capable of binding the cis element. Suitable DNA fragments or molecules comprise or consist of one or more of the following: sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEA1 as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175.

A preferred class of agents of the present invention comprises nucleic acid molecules will encode all or a fragment of “TIGR promoter” or flanking gene sequences. As used herein, the terms “TIGR promoter” or “promoter” is used in an expansive sense to refer to the regulatory sequence(s) that control mRNA production. Such sequences include RNA polymerase binding sites, glucocorticoid response elements, enhancers, etc. All such TIGR molecules may be used to diagnose the presence of glaucoma and severity of glaucoma. Such molecules may be either DNA or RNA.

Fragment nucleic acid molecules may encode significant portion(s) of, or indeed most of, SEQ ID NO: 1 or SEQ ID NO: 3 or SEQ ID NO: 4 or SEQ ID NO: 5. Alternatively, the fragments may comprise smaller oligonucleotides (having from about 15 to about 250 nucleotide residues, and more preferably, about 15 to about 30 nucleotide residues.). Such oligonucleotides include SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25.

Alternatively such oligonucleotides may derive from either the TIGR promoter, TIGR introns, TIGR exons, TIGR cDNA and TIGR downstream sequences comprise or consist of one or more of the following: sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAL as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175. For such purpose, the oligonucleotides must be capable of specifically hybridizing to a nucleic acid molecule genetically or physically linked to the TIGR gene. As used herein, the term "linked" refers to genetically, physically or operably linked.

As used herein, two nucleic acid molecules are said to be capable of specifically hybridizing to one another if the two molecules are capable of forming an anti-parallel, double-stranded nucleic acid structure, whereas they are unable to form a double-stranded structure when incubated with a non-TIGR nucleic acid molecule. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, J., et al., (In: *Molecular Cloning, a Laboratory Manual, 2nd Edition, Cold Spring Harbor Press,* Cold Spring Harbor, N.Y. (1989)), and by Haymes, B. D., et al. (In: *Nucleic Acid Hybridization, A Practical Approach,* IRL Press, Washington, DC (1985)), both herein incorporated by reference). Departures from complete complementarity are therefore permissible, as long as such departures do not completely preclude the capacity of the molecules to form a double-stranded structure. Thus, in order for an oligonucleotide to serve as a primer it need only be sufficiently complementary in sequence to be able to form a stable double-stranded structure under the particular solvent and salt concentrations employed.

Apart from their diagnostic or prognostic uses, such oligonucleotides may be employed to obtain other TIGR nucleic acid molecules. Such molecules include the TIGR-encoding nucleic acid molecule of non-human animals (particularly, cats, monkeys, rodents and dogs), fragments thereof, as well as their promoters and flanking sequences. Such molecules can be readily obtained by using the above-described primers to screen cDNA or genomic libraries obtained from non-human species. Methods for forming such libraries are well known in the art. Such analogs may differ in their nucleotide sequences from that of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or from molecules consisting of sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAL as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 because complete complementarity is not needed for stable hybridization. The TIGR nucleic acid molecules of the present invention therefore also include molecules that, although capable of specifically hybridizing with TIGR nucleic acid molecules may lack "complete complementarity."

Any of a variety of methods may be used to obtain the above-described nucleic acid molecules (Elles, Methods in Molecular Medicine: Molecular Diagnosis of Genetic Diseases, Humana Press (1996), herein incorporated by reference). SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAL as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 may be used to synthesize all or any portion of the TIGR promoter or any of the TIGR upstream motifs or portions the TIGR cDNA (Zamechik et al., *Proc. Natl. Acad. Sci.* (*U.S.A.*) 83:4143 (1986); Goodchild et al., *Proc. Natl. Acad. Sci.* (*U.S.A.*) 85:5507 (1988); Wickstrom et al., *Proc. Natl. Acad. Sci.* (*U.S.A.*) 85:1028; Holt, J. T. et al., *Molec. Cell. Biol.* 8:963 (1988); Gerwirtz, A. M. et al., *Science* 242:1303 (1988); Anfossi, G., et al., *Proc. Natl. Acad. Sci.* (*U.S.A.*) 86:3379

(1989); Becker, D., et al., *EMBO* 1. 8:3679 (1989); all of which references are incorporated herein by reference).

Automated nucleic acid synthesizers may be employed for this purpose. In lieu of such synthesis, the disclosed SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAI as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 may be used to define a pair of primers that can be used with the polymerase chain reaction (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)) to amplify and obtain any desired TIGR gene DNA molecule or fragment.

The TIGR promoter sequence(s) and TIGR flanking sequences can also be obtained by incubating oligonucleotide probes of TIGR oligonucleotides with members of genomic human libraries and recovering clones that hybridize to the probes. In a second embodiment, methods of "chromosome walking," or 3' or 5' RACE may be used (Frohman, M. A. et al., *Proc. Natl. Acad. Sci.* (*U.S.A.*) 85:8998–9002 (1988), herein incorporated by reference); Ohara, O. et al., *Proc. Natl. Acad. Sci.* (*U.S.A.*) 86:5673–5677 (1989), herein incorporated by reference) to obtain such sequences.

II. Uses of the Molecules of the Invention in the Diagnosis and Prognosis of Glaucoma and Related Diseases A particularly desired use of the present invention relates to the diagnosis of glaucoma, POAG, pigmentary glaucoma, high tension glaucoma and low tension glaucoma and their related diseases. Another particularly desired use of the present invention relates to the prognosis of glaucoma, POAG, pigmentary glaucoma, high tension glaucoma and low tension glaucoma and their related diseases. As used herein the term "glaucoma" includes both primary glaucomas, secondary glaucomas, juvenile glaucomas, congenital glaucomas, and familial glaucomas, including, without limitation, pigmentary glaucoma, high tension glaucoma and low tension glaucoma and their related diseases. As indicated above, methods for diagnosing or prognosing glaucoma suffer from inaccuracy, or require multiple examinations. The molecules of the present invention may be used to define superior assays for glaucoma. Quite apart from such usage, the molecules of the present invention may be used to diagnosis or predict an individual's sensitivity to elevated intraocular pressure upon administration of steroids such as glucocorticoids or corticosteroids, or anti-inflammatory steroids). Dexamethasone, cortisol and prednisolone are preferred steroids for this purpose. Medical conditions such as inflammatory and allergic disorders, as well as organ transplantation recipients, benefit from treatment with glucocorticoids. Certain individuals exhibit an increased sensitivity to such steroids (i.e., "steroid sensitivity"), which is manifested by an undesired increase in intraocular pressure. The present invention may be employed to diagnosis or predict such sensitivity, as well as glaucoma and related diseases.

In a first embodiment, the TIGR molecules of the present invention are used to determine whether an individual has a mutation affecting the level (i.e., the concentration of TIGR mRNA or protein in a sample, etc.) or pattern (i.e., the kinetics of expression, rate of decomposition, stability profile, etc.) of the TIGR expression (collectively, the "TIGR response" of a cell or bodily fluid) (for example, a mutation in the TIGR gene, or in a regulatory region(s) or other gene(s) that control or affect the expression of TIGR), and being predictive of individuals who would be predisposed to glaucoma (prognosis), related diseases, or steroid sensitivity. As used herein, the TIGR response manifested by a cell or bodily fluid is said to be "altered" if it differs from the TIGR response of cells or of bodily fluids of normal individuals. Such alteration may be manifested by either abnormally increased or abnormally diminished TIGR response. To determine whether a TIGR response is altered, the TIGR response manifested by the cell or bodily fluid of the patient is compared with that of a similar cell sample (or bodily fluid sample) of normal individuals. As will be appreciated, it is not necessary to re-determine the TIGR response of the cell sample (or bodily fluid sample) of normal individuals each time such a comparison is made; rather, the TIGR response of a particular individual may be compared with previously obtained values of normal individuals.

In one sub-embodiment, such an analysis is conducted by determining the presence and/or identity of polymorphism(s) in the TIGR gene or its flanking regions which are associated with glaucoma, or a predisposition (prognosis) to glaucoma, related diseases, or steroid sensitivity. As used herein, the term "TIGR flanking regions" refers to those regions which are located either upstream or downstream of the TIGR coding region.

Any of a variety of molecules can be used to identify such polymorphism(s). In one embodiment, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAL as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFICB as set forth in FIG. 1 at residues 5166–5175 (or a subsequence thereof) may be employed as a marker nucleic acid molecule to identify such polymorphism(s).

Alternatively, such polymorphisms can be detected through the use of a marker nucleic acid molecule or a marker protein that is genetically linked to (i.e., a polynucleotide that co-segregates with) such polymorphism(s). As stated above, the TIGR gene and/or a sequence or sequences that specifically hybridize to the TIGR gene have been mapped to chromosome 1 q, 21–32, and more preferably to the TIGR gene located at chromosome 1, q21–27, and more preferably to the TIGR gene located at chromosome 1, q22–26, and most preferably to the TIGR gene located at chromosome 1, q24. In a preferred aspect of this embodiment, such marker nucleic acid molecules will have the nucleotide sequence of a polynucleotide that is closely genetically linked to such polymorphism(s) (e.g., markers located at chromosome 1, q19–25 (and more preferably chromosome 1, q23–25, and most preferably chromosome 1, q24.

Localization studies using a Stanford G3 radiation hybrid panel mapped the TIGR gene with the D1S2536 marker nucleic acid molecules at the D1S2536 locus with a LOD score of 6.0. Other marker nucleic acid molecules in this region include: D1S210; D1S1552; D1S2536; D1S2790; SHGC-12820; and D1S2558. Other polynucleotide markers that map to such locations are known and can be employed to identify such polymorphism(s).

The genomes of animals and plants naturally undergo spontaneous mutation in the course of their continuing evolution (Gusella, J. F., *Ann. Rev. Biochem.* 55:831–854 (1986)). A "polymorphism" in the TIGR gene or its flanking regions is a variation or difference in the sequence of the TIGR gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e. the original "allele") whereas other members may have the variant sequence (i.e. the variant "allele"). In the simplest case, only one variant sequence may exist, and the polymorphism is thus said to be di-allelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity and paternity analysis (Weber, J. L., U.S. Pat. No. 5,075,217; Armour, J. A. L. et al., *FEBS Lett.* 307:113–115 (1992); Jones, L. et al., *Eur. J. Haematol.* 39:144–147 (1987); Horn, G. T. et al., PCT Application W091/14003; Jeffreys, A. J., European Patent Application 370,719; Jeffreys, A. J., U.S. Pat. No. 5,175,082); Jeffreys. A. J. et al., *Amer. J. Hum. Genet.* 39:11–24 (1986); Jeffreys. A. J. et al., *Nature* 316:76–79 (1985); Gray, I. C. et al., *Proc. R. Acad. Soc. Lond.* 243:241–253 (1991); Moore, S. S. et al., *Genomics* 10:654–660 (1991); Jeffreys, A. J. et al., *Anim. Genet.* 18:1–15 (1987); Hillel, J. et al., *Anim. Genet.* 20:145–155 (1989); Hillel, J. et al., *Genet.* 124:783–789 (1990)).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s), and more preferably within 100 kb of the polymorphism(s), and most preferably within 10 kb of the polymorphism(s) can be employed. Examples of such marker nucleic acids are set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25.

In another embodiment a marker nucleic acid will be used that is capable of specifically detecting TIGRmt1, TIGRmt2, TIGRmt3, TIGRmt4, TIGRmt5, TIGRsvl, or a combination of these mutations. Methods to detect base(s) substitutions, base(s) deletions and base(s) additions are known in the art (i.e. methods to genotype an individual). For example, "Genetic Bit Analysis ("GBA") method is disclosed by Goelet, P. et al., WO 92/15712, herein incorporated by reference, may be used for detecting the single nucleotide polymorphisms of the present invention. GBA is a method of polymorphic site interrogation in which the nucleotide sequence information surrounding the site of variation in a target DNA sequence is used to design an oligonucleotide primer that is complementary to the region immediately adjacent to, but not including, the variable nucleotide in the target DNA. The target DNA template is selected from the biological sample and hybridized to the interrogating primer. This primer is extended by a single labeled dideoxynucleotide using DNA polymerase in the presence of two, and preferably all four chain terminating nucleoside triphosphate precursors. Cohen, D. et al., (PCT Application WO91/02087) describes a related method of genotyping.

Other primer-guided nucleotide incorporation procedures for assaying polymorphic sites in DNA have been described (Komher, J. S. et al., *Nucl. Acids. Res.* 17:7779–7784 (1989), herein incorporated by reference; Sokolov, B. P., *Nucl. Acids Res.* 18:3671 (1990), herein incorporated by reference; Syvainen, A. -C., et al., *Genomics* 8:684–692 (1990), herein incorporated by reference; Kuppuswamy, M. N. et al., *Proc. Natl. Acad. Sci.* (*U.S.A.*) 88:1143–1147 (1991), herein incorporated by reference; Prezant, T. R. et al., *Hum. Mutat.* 1:159–164 (1992), herein incorporated by reference; Ugozzoli, L. et al., *GATA* 9:107–112 (1992), herein incorporated by reference; Nyren, P. et al., *Anal. Biochem.* 208:171–175 (1993), herein incorporated by reference).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

Another preferred method of achieving such amplification employs the polymerase chain reaction ("PCR") (Mullis, K. et al., *Cold Spring Harbor Symp. Quant. Biol.* 51:263–273 (1986); Erlich H. et al., European Patent Appln. 50,424; European Patent Appln. 84,796, European Patent Application 258,017, European Patent Appln. 237,362; Mullis, K., European Patent Appln. 201,184; Mullis K. et al., U.S. Pat. No. 4,683,202; Erlich, H., U.S. Pat. No. 4,582,788; and Saiki, R. et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, F., *Proc. Natl. Acad. Sci.* (*U.S.A.*) 88:189–193 (1991). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, D., PCT Application WO 90/01069).

The "Oligonucleotide Ligation Assay" ("OLA") may alternatively be employed (Landegren, U. et al., *Science* 241:1077–1080 (1988)). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, D. A. et al., have described a nucleic acid detection assay that combines attributes of PCR and OLA (Nickerson, D. A. et al., *Proc. Natl. Acad. Sci.* (*U.S.A.*) 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu, D. Y. et al., *Genomics* 4:560 (1989)), and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek, L. T. et al., U.S. Pat. No. 5,130,238; Davey, C. et al., European Patent Application 329,822; Schuster et al., U.S. Pat. No. 5,169,766; Miller, H. I. et al., PCT appln. WO 89/06700; Kwoh, D. et al., *Proc. Natl. Acad. Sci.* (*U.S.A.*) 86:1173 (1989); Gingeras, T. R. et al., PCT application WO 88/10315; Walker, G. T. et al., *Proc. Natl. Acad. Sci.* (*U.S.A.*) 89:392–396 (1992)). All the foregoing nucleic acid amplification methods could be used to predict or diagnose glaucoma.

The identification of a polymorphism in the TIGR gene can be determined in a variety of ways. By correlating the presence or absence of glaucoma in an individual with the presence or absence of a polymorphism in the TIGR gene or its flanking regions, it is possible to diagnose the predisposition (prognosis) of an asymptomatic patient to glaucoma, related diseases, or steroid sensitivity. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and animal genetic analyses (Glassberg, J., UK patent Application 2135774; Skolnick, M. H. et al., Cytogen. Cell Genet. 32:58–67 (1982); Botstein, D. et al., Ann. J. Hum. Genet. 32:314–331 (1980); Fischer, S. G et al. (PCT Application WO90/13668); Uhlen, M., PCT Application WO90/11369)). The role of TIGR in glaucoma pathogenesis indicates that the presence of genetic alterations (e.g., DNA polymorphisms) that affect the TIGR response can be employed to predict glaucoma.

A preferred method of achieving such identification employs the single-strand conformational polymorphism (SSCP) approach. The SSCP technique is a method capable of identifying most sequence variations in a single strand of DNA, typically between 150 and 250 nucleotides in length (Elles, Methods in Molecular Medicine: Molecular Diagnosis of Genetic Diseases, Humana Press (1996), herein incorporated by reference); Orita et al., *Genomics* 5: 874–879 (1989), herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to Lee et al., *Anal. Biochem.* 205: 289–293 (1992), herein incorporated by reference; Suzuki et al., *Anal. Biochem.* 192: 82–84 (1991), herein incorporated by reference; Lo et al., *Nucleic Acids Research* 20: 1005–1009 (1992), herein incorporated by reference; Sarkar et al., *Genomics* 13: 441–443 (1992), herein incorporated by reference).

In accordance with this embodiment of the invention, a sample DNA is obtained from a patient's cells. In a preferred embodiment, the DNA sample is obtained from the patient's blood. However, any source of DNA may be used. The DNA is subjected to restriction endonuclease digestion. TIGR is used as a probe in accordance with the above-described RFLP methods. By comparing the RFLP pattern of the TIGR gene obtained from normal and glaucomatous patients, one can determine a patient's predisposition (prognosis) to glaucoma. The polymorphism obtained in this approach can then be cloned to identify the mutation at the coding region which alters the protein's structure or regulatory region of the gene which affects its expression level. Changes involving promoter interactions with other regulatory proteins can be identified by, for example, gel shift assays using HTM cell extracts, fluid from the anterior chamber of the eye, serum, etc. Interactions of TIGR protein in glaucomatous cell extracts, fluid from the anterior chamber of the eye, serum, etc. can be compared to control samples to thereby identify changes in those properties of TIGR that relate to the pathogenesis of glaucoma. Similarly such extracts and fluids as well as others (blood, etc.) can be used to diagnosis or predict steroid sensitivity.

Several different classes of polymorphisms may be identified through such methods. Examples of such classes include: (1) polymorphisms present in the TIGR cDNA of different individuals; (2) polymorphisms in non-translated TIGR gene sequences, including the promoter or other regulatory regions of the TIGR gene; (3) polymorphisms in genes whose products interact with TIGR regulatory sequences; (4) polymorphisms in gene sequences whose products interact with the TIGR protein, or to which the TIGR protein binds.

In an alternate sub-embodiment, the evaluation is conducted using oligonucleotide "probes" whose sequence is complementary to that of a portion of SEQ ID NO: 1, SEQ ID NO: 2 SEQ ID NO: 3, SEQ ID NO: 4, or SEQ ID NO: 5. Such molecules are then incubated with cell extracts of a patient under conditions sufficient to permit nucleic acid hybridization.

In one sub-embodiment of this aspect of the present invention, one can diagnose or predict glaucoma, related diseases and steroid sensitivity by ascertaining the TIGR response in a biopsy (or a macrophage or other blood cell sample), or other cell sample, or more preferably, in a sample of bodily fluid (especially, blood, serum, plasma, tears, buccal cavity, etc.). Since the TIGR gene is induced in response to the presence of glucocorticoids, a highly preferred embodiment of this method comprises ascertaining such TIGR response prior to, during and/or subsequent to, the administration of a glucocorticoid. Thus, by way of illustration, glaucoma could be diagnosed or predicted by determining whether the administration of a glucocorticoid (administered topically, intraocularly, intramuscularly, systemically, or otherwise) alters the TIGR response of a particular individual, relative to that of normal individuals. Most preferably, for this purpose, at least a "TIGR gene-inducing amount" of the glucocorticoid will be provided. As used herein, a TIGR gene-inducing amount of a glucocorticoid is an amount of glucocorticoid sufficient to cause a detectable induction of TIGR expression in cells of glaucomatous or non-glaucomatous individuals.

III. Methods of Administration

The agents of the present invention can be formulated according to known methods to prepare pharmacologically acceptable compositions, whereby these materials, or their functional derivatives, having the desired degree of purity are combined in admixture with a physiologically acceptable carrier, excipient, or stabilizer. Such materials are non-toxic to recipients at the dosages and concentrations employed. The active component of such compositions may be agents analogs or mimetics of such molecules. Where nucleic acid molecules are employed, such molecules may be sense, antisense or triplex oligonucleotides of the TIGR promoter, TIGR cDNA, TIGR intron, TIGR exon or TIGR gene.

A composition is said to be "pharmacologically acceptable" if its administration can be tolerated by a recipient patient. An agent is physiologically significant if its presence results in a detectable change in the physiology of a recipient patient.

Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the TIGR molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable articles. For preparing sustained-release compositions, the TIGR molecule(s) of the composition is preferably incorporated into a biodegradable matrix or microcapsule. A suitable material for this purpose is a polylactide, although other polymers of poly-(a-hydroxycarboxylic acids), such as poly-D-(−)-3-hydroxybutyric acid (EP 133,988A), can be used. Other biodegradable polymers include poly(lactones), poly (orthoesters), polyamino acids, hydrogels, or poly (orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al., *Chem. Tech.* 12:98 (1982).

Alternatively, instead of incorporating the TIGR molecule (s) of the composition into polymeric particles, it is possible to entrap these materials in microcapsules prepared, for example, by coacervation techniques or by interfacial polymerization, for example, hydroxymethylcellulose or gelatine-microcapsules and poly-(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art, see, for example, Chicz, R. M. et al. (PCT Application WO 94/04557), Jaysena, S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

Having now generally described the invention, the same will be more readily understood through reference to the following examples which are provided by way of illustration, and are not intended to be limiting of the present invention, unless specified.

EXAMPLE 1

Single Strand Conformational Polymorphism

Single strand conformational polymorphism (SSCP) screening is carried out according to the procedure of Hue et al., *The Journal of Investigative Ophthalmology* 105.4: 529–632 (1995), herein incorporated by reference. SSCP primers are constructed corresponding to sequences found within the TIGR promoter and two of exons of TIGR. The following primers are constructed: forward primer "Sk−1a": 5'-TGA GGC TTC CTC TGG AAA C-3' (SEQ ID NO: 6); reverse primer "ca2": 5'-TGA AAT CAG CAC ACC AGT AG-3' (SEQ ID NO: 7); forward primer "CA2": 5'-GCA CCC ATA CCC CAA TAA TAG-3' (SEQ ID NO: 8); reverse primer "Pr+1": 5'-AGA GTT CCC CAG ATT TCA CC-3' (SEQ ID NO: 9); forward primer "Pr−1": 5'-ATC TGG GGA ACT CTT CTC AG-3' (SEQ ID NO: 10); reverse primer "Pr+2(4A2)": 5'-TAC AGT TGT TGC AGA TAC G-3' (SEQ ID NO: 11); forward primer "Pr−2(4A)": 5'-ACA ACG TAT CTG CAA CAA CTG-3' (SEQ ID NO: 12); reverse primer "Pr+3(4A)": 5'-TCA GGC TTA ACT GCA GAA CC-3' (SEQ ID NO: 13); forward primer "Pr−3(4A)": 5'-TTG GTT CTG CAG TTA AGC C-3' (SEQ ID NO: 14); reverse primer "Pr+2(4A1)": 5'-AGC AGC ACA AGG GCA ATC C-3' (SEQ ID NO: 15); reverse primer "Pr+1(4A)": 5'-ACA GGG CTA TAT TGT GGG-3' (SEQ ID NO: 16); forward primer "KS1X": 5'-CCT GAG ATG CCA GCT GTC C-3' (SEQ ID NO: 17); reverse primer "SK1XX": 5'-CTG AAG CAT TAG AAG CCA AC-3' (SEQ ID NO: 18); forward primer "KS2a1": 5'-ACC TTG GAC CAG GCT GCC AG-3' (SEQ ID NO: 19); reverse primer "SK3"5'-AGG TTT GTT CGA GTT CCA G-3' (SEQ ID NO: 20); forward primer "KS4": 5'-ACA ATT ACT GGC AAG TAT GG-3' (SEQ ID NO: 21); reverse primer "SK6A": 5'-CCT TCT CAG CCT TGC TAC C-3' (SEQ ID NO: 22); forward primer "KS5": 5'-ACA CCT CAG CAG ATG CTA CC-3' (SEQ ID NO: 23); reverse primer "SK8": 5'-ATG GAT GAC TGA CAT GGC C-3' (SEQ ID NO: 24); forward primer "KS6": 5'-AAG GAT GAA CAT GGT CAC C-3' (SEQ ID NO: 25).

The locations of primers: Sk−1a, ca2, CA2, Pr+1, Pr−1, Pr+2(4A2), Pr−2(4A), Pr+3(4A), Pr−3 (4A), Pr−3(4A), Pr+2(4A1), and Pr+1(4A) are diagramatically set forth in FIG. 4. The location of primers: KS1X, SK1XX, Ks2a1, SK3, KS4, SK6A, KS5, SK8, and KS6 are diagramatically set forth in FIG. 5.

Families with a history of POAG in Klamath Falls, Oreg., are screened by SSCP according to the method of Hue et al., *The Journal of Investigative Ophthalmology* 105.4: 529–632 (1995), herein incorporated by reference). SSCP primers SK−1a, ca2, CA2, Pr+1, Pr−2(4A), Pr+3(4A), SK1XX, and KS6 detect single strand conformational polymorphisms in this population. An SSCP is detected using SSCP primers Pr+3(4A) and Pr−2(4A). 70 family members of the Klamath Fall, Oreg. are screened with these primers and the results are set forth in Table 1.

TABLE 1

| | Total | SSCP+ | SSCP− |
|---|---|---|---|
| Glaucoma positive individuals[1] | 12 | 12 | 0 |
| Glaucoma negative individuals | 13 | 0 | 13 |
| Spouses (glaucoma negative) | 16 | 2 | 14 |
| Others[2] | 29 | 6 | 23 |

[1]= glaucoma positive individuals as determined by IOP of greater than 25 mmHg
[2]= unidentified glaucoma due to the age of the individual.

A second SSCP is detected using SSCP primers Pr+1 and CA2. 14 family members of the Klamath Fall, Oreg. are screened with these primers. A characteristic polymorphism is found in the 6 affected family members but absent in the 8 unaffected members. A third SSCP is detected using SSCP primers ca2 and sk-la. The same 14 family members of the Klamath Fall, Oreg. that are screened with Pr+1 and CA2 are screened with ca2 and sk−1a primers. A characteristic polymorphism is found in the 6 affected family members but absent in the 8 unaffected members. A fourth SSCP is detected using SSCP primers KS6 and SKLXX. 22 family members of the Klamath Fall, Oreg. and 10 members of a Portland, Oregon pedigree are screened with these primers. A polymorphism is found in exon 3. The results are as set forth in Table 2.

TABLE 2

| | Total | SSCP+ | SSCP− |
|---|---|---|---|
| Klamath Fall, Oregon | | | |
| Glaucoma positive individuals[1] | 3 | 3 | 0 |
| Glaucoma negative individuals | 6 | 0 | 6 |
| Others[2] | 13 | 6 | 7 |
| Portland, Oregon | | | |
| Glaucoma positive individuals[1] | 6 | 6 | 0 |
| Glaucoma negative individuals | 4 | 0 | 4 |
| Others[2] | 0 | 0 | 0 |

[1]= glaucoma positive individuals as determined by IOP of greater than 25 mmHg
[2]= unidentified glaucoma due to the age of the individual.

EXAMPLE 2

TIGR Homologies

A novel myosin-like acidic protein termed myocilin is expressed predominantly in the photoreceptor cells of retina and is localized particularly in the rootlet and basal body of connecting cilium (Kubota et al., *Genomics* 41: 360–369 (1997), herein incorporated by reference). The myocilin gene is mapped to human chromosome Iq23-q24. The coding region of myocilin is 100 percent homologous with TIGR.

Homology searches are performed by GCG (Genetics Computer Group, Madison, Wis.) and include the GenBank, EMBL, Swiss-Prot databases and EST analysis. Using the Blast search, the best fits are found with a stretch of 177 amino acids in the carboxy terminals for an extracellular mucus protein of the olfactory, olfactomedin and three olfactomedin-like species. The alignment presented in FIG. 6 shows the TIGR homology (SEQ ID NO. 27) to an expressed sequence tag (EST) sequence from human brain (ym08h12.r1)(SEQ ID NO. 28)(The WashU-Merck EST Project, 1995); the Z domain of olfactomedin-related glycoprotein from rat brain (IB426bAMZ)(SEQ ID NO. 29) (Danielson et al., *Journal of Neuroscience Research* 38: 468–478 (1994), herein incorporated by reference) and the olfactomedin from olfactory tissue of bullfrogs (ranofm) (SEQ ID NO. 30)(Yokoe and Anholt, *Proc. Natl. Acad. Sci.* 90: 4655–4659 (1993), herein incorporated by reference; Snyder and Anholt, *Biochemistry* 30: 9143–9153 (1991), herein incorporated by reference). These domains share very similar amino acid positions as depicted in the consensus homology of FIG. 6 (SEQ ID NO. 31), with the exception being the truncated human clone in which the position with respect to its full length sequence has not been established. No significant homology is found for the amino termini of these molecules.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

What is claimed is:

1. A method for diagnosing glaucoma in a sample obtained from a cell or a bodily fluid by detecting mutants in the promoter region of the TIGR gene, comprising the steps of:

(A) incubating under conditions permitting nucleic acid hybridization, a marker nucleic acid molecule, said marker nucleic acid molecule having a nucleic acid sequence that specifically hybridizes to a sequence selected from the group consisting of SEQ ID NO: 1, SEQ ID NO: 2, SEQ ID NO: 3, SEQ ID NO: 4, SEQ ID NO:5, and the complements thereof, and a complementary nucleic acid molecule obtained from a sample, wherein nucleic acid hybridization between said marker nucleic acid molecule and said complementary nucleic acid molecule permits the detection of a polymorphism;

(B) permitting hybridization between said marker nucleic acid molecule and said complementary nucleic acid molecule; and (C) detecting the presence of said polymorphism, wherein the detection of said polymorphism is diagnostic of glaucoma.

2. The method for diagnosing glaucoma of claim 1, wherein said marker nucleic acid is capable of specifically detecting TIGRmt1.

3. The method for diagnosing glaucoma of claim 1, wherein said marker nucleic acid molecule is selected from the group consisting of a nucleic acid molecule that comprises the sequence of SEQ ID NO: 8 and a nucleic acid molecule that comprises the sequence of SEQ ID NO: 12.

4. Thc method for diagnosing glaucoma of claim 1, wherein said marker nucleic acid molecule comprises a sequence selected from the group consisting of SEQ ID NO: 6 through SEQ ID NO: 25.

5. The method for diagnosing glaucoma of claim 1, wherein said polymorphism is TIGRmt1.

6. The method for diagnosing glaucoma of claim 1, wherein said polymorphism is TIGRmt2.

7. The method for diagnosing glaucoma of claim 1, wherein said polymorphism is TIGRmt3.

8. The method for diagnosing glaucoma of claim 1, wherein said polymorphism is TIGRmt4.

9. The method for diagnosing glaucoma of claim 1, wherein said polymorphism is TIGRmt5.

10. The method for diagnosing glaucoma of claim 1, wherein said polymorphism is TIGRsv1.

11. The method for diagnosing glaucoma of claim 1, further comprising a second marker nucleic acid molecule.

12. A method for prognosing glaucoma in a sample obtained from a cell or a bodily fluid by detecting mutants in the promoter region of the TIGR gene, comprising the steps of:

(A) incubating under conditions permitting nucleic acid hybridization, a marker nucleic acid molecule, said marker nucleic acid molecule having a nucleic acid sequence that specifically hybridizes to a sequence selected from the group consisting of SEQ ID NO: 1, SEQ ID NO: 2, SEQ ID NO: 3, SEQ ID NO: 4, SEQ ID NO: 5, and the complements thereof, and a complementary nucleic acid molecule obtained from a sample, wherein nucleic acid hybridization between said marker nucleic acid molecule and said complementary nucleic acid molecule permits the detection of a polymorphism;

(B) permitting hybridization between said marker nucleic acid molecule and said complementary nucleic acid molecule; and (C) detecting the presence of said polymorphism, wherein the detection of said polymorphism is prognostic of glaucoma.

13. The method for prognosing glaucoma of claim 12, wherein said marker nucleic acid is capable of specifically detecting TIGRmt1.

14. The method for prognosing glaucoma of claim 12, wherein said marker nucleic acid molecule is selected from the group consisting of a nucleic acid molecule that comprises the sequence of SEQ ID NO: 8 and a nucleic acid molecule that comprises the sequence of SEQ ID NO: 12.

15. The method for prognosing glaucoma of claim 12, wherein said marker nucleic acid molecule comprises a sequence selected from the group consisting of SEQ ID NO: 6 through SEQ ID NO: 25.

16. The method for prognosing glaucoma of claim 12, wherein said polymorphism is TIGRmt1.

17. The-method for prognosing glaucoma of claim 12, wherein said polymorphism is selected from the group consisting of TIGRmt2, TIGRmt3, TIGRmt4, TIGRmt5, and TIGRsv1.

18. The method for prognosing glaucoma of claim 12, further comprising a second marker nucleic acid molecule.

19. A method for diagnosing steroid sensitivity in a sample obtained from a cell or a bodily fluid by detecting mutants in the promoter region of the TIGR gene, comprising the steps of:

(A) incubating under conditions permitting nucleic acid hybridization, a marker nucleic acid molecule, said marker nucleic acid molecule having a nucleic acid sequence that specifically hybridizes to a sequence selected from the group consisting of SEQ ID NO: 1, SEQ ID NO: 2, SEQ ID NO: 3, SEQ ID NO: 4, SEQ ID NO: 5, and the complements thereof, and a complementary nucleic acid molecule obtained from a sample, wherein nucleic acid hybridization between said marker nucleic acid molecule and said complementary nucleic acid molecule permits the detection of a polymorphism;

(B) permitting hybridization between said marker nucleic acid molecule and said complementary nucleic acid molecule; and (C) detecting the presence of said polymorphism, wherein the detection of said polymorphism is diagnostic of steroid sensitivity.

20. The method for diagnosing steroid sensitivity of claim 19, wherein said marker nucleic acid is capable of specifically detecting TIGRmt1.

21. The method for diagnosing steroid sensitivity of claim 19, wherein said marker nucleic acid molecule is selected from the group consisting of a nucleic acid molecule that comprises the sequence of SEQ ID NO: 8 and a nucleic acid molecule that comprises the sequence of SEQ ID NO: 12.

22. The method for diagnosing steroid sensitivity of claim 19, wherein said marker nucleic acid molecule comprises a sequence selected from the group consisting of SEQ ID NO: 6 through SEQ ID NO: 25.

23. The method for diagnosing steroid sensitivity of claim 19, wherein said polymorphism is TIGRmt1.

24. The method for diagnosing steroid sensitivity of claim 19, wherein said polymoiphism is selected from the group consisting of TIGRmt2, TIGRmt3, TIGRmt4, TIGRmt5, and TIGRsv1.

25. The method for diagnosing steroid sensitivity of claim 19, further comprising a second marker nucleic acid molecule.

26. A method for diagnosing or prognosing glaucoma in a sample obtained from a cell or a bodily fluid by detecting mutants in the promoter region of the TIGR gene, comprising the steps of:

(A) incubating under conditions permitting nucleic acid hybridization, a marker nucleic acid molecule, said marker nucleic acid molecule having a nucleic acid sequence that specifically hybridizes to a TIGR promoter sequence, or its complement, and a complementary nucleic acid molecule obtained from a sample, wherein nucleic acid hybridization between said marker nucleic acid molecule and said complementary nucleic acid molecule permits the detection of a polymorphism;

(B) permitting hybridization between said marker nucleic acid molecule and said complementary nucleic acid molecule; and (C) detecting the presence of said polymorphism, wherein the detection of said polymorphism is diagnostic or prognostic of glaucoma.

27. The method for diagnosing or prognosing glaucoma of claim 26, wherein said TIGR promoter sequence comprises SEQ ID NO: 1 or a fragment thereof.

28. The method for diagnosing or prognosing glaucoma of claim 26, wherein said TIGR promoter sequence comprises SEQ ID NO: 2 or a fragment thereof.

29. The method for diagnosing or prognosing glaucoma of claim 26, wherein said TIGR promoter sequence comprises SEQ ID NO: 3 or a fragment thereof.

30. The method for diagnosing or prognosing glaucoma of claim 26, wherein said TIGR promoter sequence comprises SEQ ID NO: 4 or a fragment thereof.

31. The method for diagnosing or prognosing glaucoma of claim 26, wherein said TIGR promoter sequence comprises SEQ ID NO: 5 or a fragment thereof.

32. The method for diagnosing or prognosing glaucoma of claim 26, wherein said marker nucleic acid is capable of specifically detecting TIGRmt1.

33. The method for diagnosing or prognosing glaucoma of claim 26, wherein said marker-nucleic acid molecule is selected from the group consisting of a nucleic acid molecule that comprises the sequence of SEQ ID NO: 8 and a nucleic acid molecule that comprises the sequence of SEQ ID NO: 12.

34. The method for diagnosing or prognosing glaucoma of claim 26, wherein said marker nucleic acid molecule comprises a sequence selected from the group consisting of SEQ ID NO: 6 through SEQ ID NO: 25.

35. The method for diagnosing or prognosing glaucoma of claim 26, wherein said polymorphism is selected from the group consisting of TIGRmt1, TIGRmt2, TIGRmt3, TIGRmt4, TIGRmt5, and TIGRsv1.

36. The method for diagnosing or prognosing glaucoma of claim 26, further comprising a second marker nucleic acid molecule.

37. A method for diagnosing steroid sensitivity in a sample obtained from a cell or a bodily fluid by detecting mutants in the promoter region of the TIGR gene, comprising the steps of:

(A) incubating under conditions permitting nucleic acid hybridization, a marker nucleic acid molecule, said marker nucleic acid molecule having a nucleic acid sequence that specifically hybridizes to a TIGR promoter sequence, or its complement, and a complementary nucleic acid molecule obtained from a sample, wherein nucleic acid hybridization between said marker nucleic acid molecule and said complementary nucleic acid molecule permits the detection of a polymorphism;

(B) permitting hybridization between said marker nucleic acid molecule and said complementary nucleic acid molecule; and (C) detecting the presence of said polymorphism, wherein the detection of said polymorphism is diagnostic of steroid sensitivity.

38. The method for diagnosing steroid sensitivity of claim 37, wherein said marker nucleic acid is capable of specifically detecting TIGRmt1.

39. The method for diagnosing steroid sensitivity of claim 37, wherein said marker nucleic acid molecule is selected from the group consisting of a nucleic acid molecule that comprises the sequence of SEQ ID NO: 8 and a nucleic acid molecule that comprises the sequence of SEQ ID NO: 12.

40. The method for diagnosing steroid sensitivity of claim 37, wherein said marker nucleic acid molecule comprises a sequence selected from the group consisting of SEQ ID NO: 6 through SEQ ID NO: 25.

41. The method for diagnosing steroid sensitivity of claim 37, wherein said polymorphism is selected from the group consisting of TIGRmt1, TIGRmt2, TIGRmt3, TIGRmt4, TIGRmt5, and TIGRsv1.

42. The method for diagnosing steroid sensitivity of claim 37, further comprising a second marker nucleic acid molecule.

43. A nucleic acid molecule that comprises the sequence of SEQ ID NO: 1.

44. A recombinant DNA molecule containing a polynucleotide that specifically hybridizes to a nucleic acid containing the nucleotide sequence of SEQ ID NO: 1, wherein said polynucleotide is complementary to SEO ID NO: 1.

45. A nucleic acid molecule that comprises the sequence of SEQ ID NO: 3.

46. A nucleic acid molecule that comprises the sequence of SEQ ID NO: 4.

47. A recombinant DNA molecule containing a polynucleotide that specifically hybridizes to a nucleic acid containing the nucleotide sequence of SEQ ID NO:4, wherein said polynucleotide is complementary to SEQ ID NO:4.

48. A nucleic acid molecule that comprises the sequence of SEQ ID NO: 5.

49. A nucleic acid molecule that comprises the sequence of SEQ ID NO: 26.

* * * * *